United States Patent
Pulé et al.

(10) Patent No.: US 11,365,262 B2
(45) Date of Patent: Jun. 21, 2022

(54) CELL

(71) Applicant: AUTOLUS LIMITED, London (GB)

(72) Inventors: Martin Pulé, London (GB); Shaun Cordoba, London (GB); Matteo Righi, London (GB); James Sillibourne, London (GB)

(73) Assignee: AUTOLUS LIMITED, London (GB)

( * ) Notice: Subject to any disclaimer, the term of this patent is extended or adjusted under 35 U.S.C. 154(b) by 1087 days.

(21) Appl. No.: 15/753,505

(22) PCT Filed: Aug. 19, 2016

(86) PCT No.: PCT/GB2016/052563
§ 371 (c)(1),
(2) Date: Feb. 19, 2018

(87) PCT Pub. No.: WO2017/029511
PCT Pub. Date: Feb. 23, 2017

(65) Prior Publication Data
US 2018/0346595 A1 Dec. 6, 2018

(30) Foreign Application Priority Data

Aug. 20, 2015 (GB) .................................... 1514874

(51) Int. Cl.
C07K 16/30 (2006.01)
A61K 35/17 (2015.01)
C07K 16/18 (2006.01)
C12N 5/0783 (2010.01)
A61K 39/00 (2006.01)
A61K 38/00 (2006.01)

(52) U.S. Cl.
CPC .......... *C07K 16/3069* (2013.01); *A61K 35/17* (2013.01); *A61K 39/001102* (2018.08); *A61K 39/001194* (2018.08); *A61K 39/001195* (2018.08); *C07K 16/18* (2013.01); *C07K 16/3061* (2013.01); *C12N 5/0636* (2013.01); *A61K 38/00* (2013.01); *A61K 2039/5156* (2013.01); *A61K 2039/5158* (2013.01); *A61K 2039/55522* (2013.01); *C07K 2317/622* (2013.01); *C07K 2319/03* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| 2012/0134970 A1* | 5/2012 | Yang | ...................... | C07K 16/18 424/93.21 |
|---|---|---|---|---|
| 2016/0289293 A1 | 10/2016 | Pule et al. | | |
| 2016/0289294 A1 | 10/2016 | Pule et al. | | |

FOREIGN PATENT DOCUMENTS

| WO | WO-2013/123061 A1 | 8/2013 |
|---|---|---|
| WO | WO-2014/145252 A2 | 9/2014 |
| WO | WO-2015/075469 A1 | 5/2015 |
| WO | WO-2015/142675 A2 | 9/2015 |

OTHER PUBLICATIONS

Whilding, L. et al, 2015, Mol. Oncology, V. 9: pp. 1994-2018.*
Bayat et al., "Production and Characterization of Monoclonal Antibodies against Human Prostate Specific Antigen," Avicenna J Med Biotechnol, 7(1):2-7 (2015).
Donnelly et al., "The 'cleavage' activities of foot-and-mouth disease virus 2A site-directed mutants and naturally occurring '2A-like' sequences," J Gen Virol, 82(5):1027-1041 (2001).
Firor et al., "From humble beginnings to success in the clinic: Chimeric antigen receptor-modified T-cells and implications for immunotherapy," Experimental Biology and Medicine, 240(8):1087-1098 (2015).
Ghorashian et al., "CD19 chimeric antigen receptor T cell therapy for haematological malignancies," British Journal of Haematology, 169(4):463-478 (2015).
International Preliminary Reporton Patentability for Application No. PCT/GB2016/052563, dated Feb. 20, 2018.
International Search Report and Written Opinion for Application No. PCT/GB2016/052563, dated Oct. 25, 2016.
Leinonen et al., "Characterization of monoclonal antibodies against prostate specific antigen produced by genetic immunization," J Immunol Methods, 289(1-2):157-167 (2004).
Liu et al., "A seven-helix coiled coil," PNAS, 103(42):15457-15462 (2006).
Lupas et al., "The Structure of a-Helical Coiled Coils," Advances in Protein Chemistry, 70:37-38 (2005).
Mahrenholz et al., "Complex Networks Govern Coiled-Coil Oligomerization—Predicting and Profiling by Means of a Machine Learning Approach," Mol Cell Proteomics, 10:M110.004994-1-M110.004994-9 (2011).
Staub et al., "Systematic identification of immunoreceptor tyrosine-based inhibitory motifs in the human proteome," Cell Signal, 16(4):435-456 (2004).
Stura et al., "Crystal Structure of Human Prostate-Specific Antigen in a Sandwich Antibody Complex," J Mol Biol, 414(4):530-544 (2011).
Zaccai et al., "A de novo peptide hexamer with a mutable channel," Nature Chem Biol, 7(12):935-941 (2011).
Hudecek et al., "Engineered T cells modified with a high-affinity ROR1-CAR confer superior antitumor reactivity in vitro and in a mouse lymphoma model," Onkologie 35(suppl 6), Abstract V639, p. 191 (2012).
Hudecek et al., "The anti-tumor reactivity of ROR1-CAR modified T cells depends on the targeted epitope, CAR-affinity and design of the CAR extracellular domain," Clinical Lymphoma, Myeloma and Leukemia, vol. 11(2):S280-S281, Abstract (2011).

(Continued)

Primary Examiner — Michael D Burkhart
(74) Attorney, Agent, or Firm — Marshall, Gerstein & Borun LLP

(57) ABSTRACT

The present invention provides a cell which comprises a first chimeric antigen receptor (CAR) and a second CAR, wherein the first and second CARs bind different epitopes on the same ligand. The cell may be used in a method for treating a disease, such as cancer.

19 Claims, 18 Drawing Sheets

Specification includes a Sequence Listing.

(56) References Cited

OTHER PUBLICATIONS

Kloss et al., "Combinatorial antigen recognition with balanced signaling promotes selective tumor eradication by engineered T cells," Nat Biotechnol. 31(1):71-75 (2013).
Shi et al., "Chimeric antigen receptor for adoptive immunotherapy of cancer: latest research and future prospects," Molecular Cancer 13:219, 8 pages (2014).
Cordoba et al., "Chimeric Antigen Receptor Logical AND gate based on CD45/CD148 Phosphates," Molecular Therapy 22(Suppl 1) Abstract #157, S59 (2014).
Jensen et al., "Design and implementation of adoptive therapy with chimeric antigen receptor mediated T cells," Immunology Reviews 257(1):127-144 (2014).
U.S. Appl. No. 15/037,414 (US-2016/0289294-A1), filed May 18, 2016.
U.S. Appl. No. 15/037,405 (US-2016/0289293-A1), filed May 18, 2016.

\* cited by examiner

CELL

FIELD OF THE INVENTION

The present invention relates to a chimeric-antigen receptor (CAR) expressing cell which is capable of recognising a ligand, for example a soluble ligand.

BACKGROUND TO THE INVENTION

Chimeric Antigen Receptors (CARs)

A number of immunotherapeutic agents have been described for use in cancer treatment, including therapeutic monoclonal antibodies (mAbs), bi-specific T-cell engagers and chimeric antigen receptors (CARs).

Chimeric antigen receptors are proteins which graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals.

The most common form of these molecules are fusions of single-chain variable fragments (scFv) derived from monoclonal antibodies which recognize a target antigen, fused via a spacer and a trans-membrane domain to a signalling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

Various CARs have been tested in vitro and in vivo trials, as summarised in Table 1 below.

TABLE 1

| Target antigen | Associated malignancy |
| --- | --- |
| α-Folate receptor | Ovarian cancer |
| CAIX | Renal cell carcinoma |
| CD19 | B-cell malignancies |
| CD20 | Lymphomas and B-cell malignancies |
| CD22 | B-cell malignancies |
| CD30 | Lymphomas |
| CD33 | AML |
| CD44v7/8 | Cervical carcinoma |
| CEA | Breast and colorectal cancer |
| EGP-2 | Multiple malignancies |
| EGP-40 | Colorectal cancer |
| erb-B2 | Colorectal, breast and prostate cancer |
| erb-B 2,3,4 | Breast and others |
| FBP | Ovarian cancer |
| Fetal acetylcholine receptor | Rhabdomyosarcoma |
| GD2 | Neuroblastoma |
| GD3 | Melanoma |
| Her2/neu | Medulloblastoma, osteosarcoma, Glioblastoma, lung malignancy |
| IL-13R-a2 | Glioma, glioblastoma, medullablastoma |
| KDR | Tumor neovasculature |
| k-light chain | B-cell malignancies |
| LeY | Carcinomas, epithelial-derived tumours |
| L1 cell adhesion molecule | Neuroblastoma |
| MAGE-A1 | Melanoma |
| Mesothelin | Various tumors |
| Murine CMV infected cells | Murine CMV |
| MUC1 | Breast, Ovary |
| NKG2D ligands | Various tumors |
| Oncofetal antigen (h5T4) | Various tumors |
| PSCA | Prostate carcinoma |
| PSMA | Prostate/tumor vasculature |

TABLE 1-continued

| Target antigen | Associated malignancy |
| --- | --- |
| TAA targeted by mAb IgE | Various tumors |
| TAG-72 | Adenocarcinomas |
| VEGF-R2 | Tumor neovasculature |

T-Cell Activation Via Segregation

T cell activation occurs because of size-based exclusion of inhibitory molecules from the synapse site, by a process known as kinetic segregation. T-cell receptor (TCR) and CARs cause T-cell signalling by stimulating tyrosine phosphorylation. In the resting T-cell, the molecules involved in this process are repeatedly colliding by means of diffusion. The TCR/CD3 complex is constantly being phosphorylated by Lck (membrane associated tyrosine kinase) and in turn continuously dephosphorylated by CD45 (tyrosine phosphatase). The continuous phosphorylation/dephosphorylation happens in a random manner and as a result the overall phosphorylation of TCR is low such that T-cell activation does not proceed.

The TCR/peptide-MHC complex or CAR-target cell ligand complex spans a short length. This forms small zones of close contact, from which the inhibitory CD45 and CD148 phosphatase molecules with ectodomains too large to fit in are excluded.

CD45 steric exclusion extends the phosphorylation half-lives of TCR/peptide-MHC complexes or CAR-target cell ligand complexes, which are trapped within the close-contact zone. Such prolonged phosphorylation of ITAMs by Lck kinase allows time for ZAP-70 recruitment, its activation by phosphorylation and subsequent phosphorylation of adaptor proteins LAT and SLP-76, leading to T-cell activation.

Central to the segregation mechanism of CAR-T-cell activation is the fact that the CAR binds an antigen on the surface of a target cell, creating the close-contact zone from which inhibitory phosphatases are excluded.

To date, CAR T-cells have therefore only been developed which recognise membrane-bound antigens on the target (e.g. tumour cell).

Soluble Tumour Antigens

Cancer development has been defined as a multistep process in which somatic cells first undergo an initiating event (i.e., environmental insult) and then a second or promoting event. The tumour microenvironment is an indispensable participant in the second part of this neoplastic process.

The tumour microenvironment is the product of a developing crosstalk between different cells types. For instance, in epithelial tumours, these cells include the invasive carcinoma and its stromal elements. Critical stromal elements include cancer-associated fibroblasts, which provide an essential communication network via secretion of growth factors and chemokines, inducing an altered ECM thus providing additional oncogenic signals enhancing cancer-cell proliferation and invasion. Active contribution of tumor-associated stromal cells to cancer progression has been recognized. Stromal elements consists of the extracellular matrix (ECM) as well as fibroblasts of various phenotypes, and a scaffold composed of immune and inflammatory cells, blood and lymph vessels, and nerves.

For tumours to progress and develop into life threatening entities, they must develop four critical abilities. First, the ability to move, second the capacity to degrade tissue matrix (ECM), third the aptitude to survive in blood and finally the physical quality of being able to establish itself in a new tissue environment. The microenvironment is of critical importance for success in this processes.

The microenvironment of cancer cells provide the necessary signals that turn on transcription factors. Thus, it is the stromal or non-malignant cells that induce the requisite transcription programs allowing the necessary mesenchymal phenotypes to invade distant tissues and establish a new environment. The cancer cells must then shut down the transcription factor programs and reconvert from mesenchymal to epithelial cells, thus recreating themselves from the core of primary tumour cells.

Tumour cells directly secrete a variety of proteins that include growth factors and ECM-degrading proteinases or induce the host to elaborate biomolecules that are able to degrade the matrix and its component adhesion molecules. The matrix degradation takes place in a region close to the tumour cell surface, where the amount of the active degradative enzymes outbalances the natural proteinase inhibitors present in the matrix or that secreted by normal cells. Proteins secreted by tumour cell into the ECM microenvironment are therefore involved in cell adhesion, motility, intercellular communication and invasion.

A cancer may therefore be characterised by the presence of numerous soluble ligands in the tumour microenvironment, including proteins secreted by the tumour cells or surrounding non-cancerous (e.g. stromal cells) and molecule produced as a result of cancer activities such as matrix degradation.

Agents, such as monoclonal antibodies targeting such soluble ligands are currently in clinical development, but to date no cellular immunotherapy approaches have been able to access this valuable antigen source.

On-Target Off-Tumour Toxicity

It is relatively rare for the presence of a single antigen effectively to describe a cancer, which can lead to a lack of specificity.

Most cancers cannot be differentiated from normal tissues on the basis of a single antigen. Hence, considerable "on-target off-tumour" toxicity occurs whereby normal tissues are damaged by the therapy. For instance, whilst targeting CD20 to treat B-cell lymphomas with Rituximab, the entire normal B-cell compartment is depleted, whilst targeting CD52 to treat chronic lymphocytic leukaemia, the entire lymphoid compartment is depleted, whilst targeting CD33 to treat acute myeloid leukaemia, the entire myeloid compartment is damaged etc.

The predicted problem of "on-target off-tumour" toxicity has been borne out by clinical trials. For example, an approach targeting ERBB2 caused death to a patient with colon cancer metastatic to the lungs and liver. ERBB2 is over-expressed in colon cancer in some patients, but it is also expressed on several normal tissues, including heart and normal vasculature.

For some cancers, targeting the presence of two cancer antigens may be more selective and therefore effective than targeting one. For example, B-chronic lymphocytic leukaemia (B-CLL) is a common leukaemia which is currently treated by targeting CD19. This treats the lymphoma but also depletes the entire B-cell compartment such that the treatment has a considerable toxic effect. B-CLL has an unusual phenotype in that CD5 and CD19 are co-expressed. By targeting only cells which express CD5 and CD19, it would be possible to considerably reduce on-target off-tumour toxicity.

If it were possible to target soluble ligands using immunotherapy approaches, then it would be possible to target a cell based on the presence of a membrane antigen in combination with the presence of a soluble ligand, such as a chemokine, cytokine or metabolite which is characteristic of tumour or non-tumour tissue. This would also be expected to considerably reduce on-target off-tumour toxicity.

SUMMARY OF ASPECTS OF THE INVENTION

Figure 1:
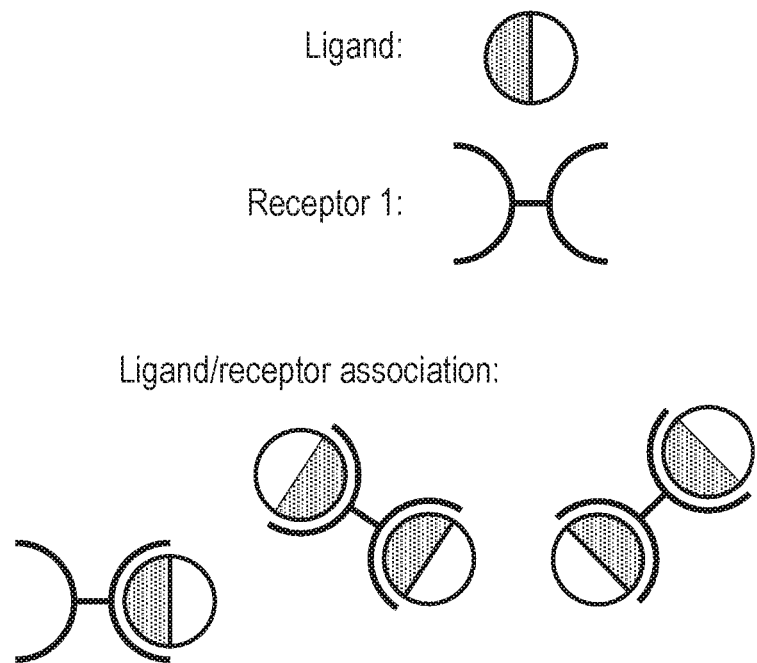
FIG. 1: A schematic diagram illustrating that a soluble ligand causes no aggregation with a single CAR T-cell.

The present inventors have found that it is possible to target a soluble ligand using a CAR approach by using a cell which comprises two CARs each recognising an epitope on the same soluble ligand.

Because the CARs recognise distinct epitopes on the same ligand, the presence of ligand causes aggregation of ligand-associated CARs on the surface of the cell. The present invention therefore, in effect, turns T-cell signalling from a segregation- to an aggregation-based process.

Thus, in a first aspect, the present invention provides a cell which comprises a first chimeric antigen receptor (CAR) and a second CAR, wherein the first and second CARs bind different epitopes on the same ligand.

The ligand may be a soluble ligand, such as a cytokine, chemokine or metabolite. The soluble ligand may, for example be selected from the following group: transforming growth factor beta (TGF-β), prostate-specific antigen (PSA), carcinoembryonic antigen (CEA) and vascular endothelial growth factor (VEGF).

Each CAR may comprise:
(i) an antigen-binding domain;
(ii) a spacer; and
(iii) a trans-membrane domain.

The spacers of the first and second CARs may be different.

The spacers of the first and/or second CAR(s) may be trimeric or multi-valent.

The cell may comprise a third CAR which binds a cell surface antigen.

The first aspect of the invention also provides five separate embodiments, each of which relate to particular arrangements of signalling in the present (or absence) of a call-surface antigen and a ligand such as a soluble ligand.

In the first embodiment, the first and/or second and third CARs each comprise:
(i) an antigen-binding domain;
(ii) a trans-membrane domain; and
(iii) an endodomain
and the endodomains of the third CAR and the first and/or second CAR(s) are complementary, such that cell activation occurs when the ligand is bound by the first and second CARs and the cell surface antigen is bound by the third CAR.

In this embodiment, the third CAR may comprise a CD3 zeta endodomain, and the first and/or second CAR(s) may comprise a CD28 endodomain and a OX40 or 41BB endodomain.

In this embodiment, the third CAR may bind prostate-specific membrane antigen (PSMA) and the first and second CARs may bind prostate-specific antigen (PSA).

In the second embodiment, the first and/or second CAR(s) comprise(s) an inhibitory endodomain, such that when the first and second CARs bind the ligand, cell activation caused by the third CAR binding the cell surface antigen is inhibited.

In the third embodiment the first CAR comprises two antigen binding domains: one which binds the soluble ligand; and one which binds a cell-surface antigen.

In this embodiment the second CAR comprises an inhibitory endodomain, such that when the first and second CARs bind the soluble ligand, cell activation caused by the first CAR binding the cell surface antigen is inhibited.

The inhibitory endodomain for the second or third embodiment may be or comprise the catalytic domain of PTPN6 or an Immunoreceptor Tyrosine-based Inhibition motif (ITIM).

For the second or third embodiment, the first and second CARs may bind IL-6.

In a fourth embodiment the first and/or second CAR(s) comprise(s) an inhibitory endodomain, such that:
in the absence of the ligand, cell activation caused by the third CAR binding the cell surface antigen is inhibited; and
in the presence of ligand, the first and second CARs aggregate and segregate from the third CAR, so that signalling can occur when the third CAR binds the cell surface antigen.

In the fourth embodiment the inhibitory endodomain may be or comprise the endodomain of CD45 or CD148.

In the fifth embodiment the first CAR lacks a functional endodomain and the second CAR is monomeric and comprises a functional endodomain, such that binding of the soluble ligand causes co-localisation of the first and second CARs and enables T-cell signalling to occur when the first CAR binds the cell surface antigen.

The second CAR may comprise a monomeric spacer, which may, for example, comprise one or more Ig domains from CD22.

In the fifth embodiment the functional endodomain on the second CAR may comprise the CD3-zeta endodomain.

In a second aspect, the present invention provides a nucleic acid construct which comprises a first nucleic acid sequence encoding a first CAR as defined above; and a second nucleic acid sequence encoding a second CAR as defined above.

The nucleic acid construct may have the following structure:

AgB1-spacer1-TM1-endo1-coexpr-AbB2-spacer2-TM2-endo2 in which

AgB1 is a nucleic acid sequence encoding the antigen-binding domain of the first CAR;

spacer 1 is a nucleic acid sequence encoding the spacer of the first CAR;

TM1 is a nucleic acid sequence encoding the transmembrane domain of the first CAR;

endo 1 is a nucleic acid sequence encoding the endodomain of the first CAR;

coexpr is a nucleic acid sequence enabling co-expression of both CARs

AgB2 is a nucleic acid sequence encoding the antigen-binding domain of the second CAR;

spacer 2 is a nucleic acid sequence encoding the spacer of the second CAR;

TM2 is a nucleic acid sequence encoding the transmembrane domain of the second CAR;

endo 2 is a nucleic acid sequence encoding the endodomain of the second CAR;

which nucleic acid construct, when expressed in a T cell, encodes a polypeptide which is cleaved at the cleavage site such that the first and second CARs are co-expressed at the T cell surface.

"coexpr" may encode a sequence comprising a self-cleaving peptide.

Alternative codons may be used in regions of sequence encoding the same or similar amino acid sequences, in order to avoid homologous recombination.

The nucleic acid construct may also comprise a nucleic acid sequence encoding a third CAR as defined above.

In a third aspect the present invention provides a vector comprising a nucleic acid construct according to the second aspect of the invention.

The vector may, for example, be a retroviral vector or a lentiviral vector or a transposon.

In a fourth aspect the present invention provides a kit which comprises:
  i) a vector comprising a nucleic acid sequence encoding a first CAR as defined above; and
  ii) a vector comprising a nucleic acid sequence encoding a second CAR as defined above.

The kit may also comprise a vector comprising a nucleic acid sequence encoding a third CAR as defined above.

In a fifth aspect, the present invention provides a method for making a cell according to the first aspect of the invention, which comprises the step of introducing: a nucleic acid construct according to the second aspect of the invention; a vector according to the third aspect of the invention; or a kit of vectors according to the fourth aspect of the invention, into a cell.

In the method of the fifth aspect of the invention, the cell may be from a sample isolated from a subject.

In a sixth aspect, the present invention provides a pharmaceutical composition comprising a plurality of cells according to the first aspect of the invention.

In a seventh aspect, the present invention provides a method for treating and/or preventing a disease, which comprises the step of administering a pharmaceutical composition according to the sixth aspect of the invention to a subject.

The method may comprise the following steps:
  (i) isolation of a cell-containing sample from a subject;
  (ii) transduction or transfection of the cells with: a nucleic acid construct according to the second aspect of the invention; a vector according to the third aspect of the invention; or a kit of vectors according to the fourth aspect of the invention; and
  (iii) administering the cells from (ii) to a subject.

The sample may be a T-cell containing sample.

The disease may be a cancer.

In an eighth aspect, the present invention provides a pharmaceutical composition according to the sixth aspect of the invention for use in treating and/or preventing a disease.

In a ninth aspect, the present invention provides the use of a cell according to the first aspect of the invention in the manufacture of a medicament for treating and/or preventing a disease.

The disease may be a cancer.

DETAILED DESCRIPTION

Chimeric Antigen Receptors (CARs)

Classical CARs are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like or ligand-based antigen binding site. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus the CAR directs the specificity and cytotoxicity of the T cell towards cells expressing the targeted antigen.

The cell of the present invention comprises a first chimeric antigen receptor (CAR) and a second CAR. The cell may also comprise third and optionally subsequent CARs.

The CARs may comprise an antigen-binding domain, a spacer domain, a transmembrane domain and an endodomain. The endodomain may comprise or associate with a domain which transmit T-cell activation signals.

Antigen Binding Domain

The antigen-binding domain is the portion of a CAR which recognizes antigen.

Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain binder such as a camelid; an artificial binder single as a Darpin; or a single-chain derived from a T-cell receptor.

The antigen-binding domain may bind an epitope on a soluble or a membrane-bound ligand, as defined below.

The term "ligand" is used synonymously with "antigen" to mean an entity which is specifically recognised and bound by the antigen-binding domain of a CAR.

Soluble Ligand

The term "soluble ligand" is used to indicate a ligand or antigen which is not part of or attached to a cell but which moves freely in the extracellular space, for example in a bodily fluid of the tissue of interest. The soluble ligand may exist in a cell-free state in the serum, plasma or other bodily fluid of an individual.

The soluble ligand may, for example, be a cytokine, chemokine or metabolite.

Cytokines are small proteins (~5-20 kDa) that are important in cell signalling. They are released by cells and affect the behaviour of other cells. Cytokines include chemokines, interferons, interleukins, lymphokines and tumour necrosis factor. Cytokines are produced by a broad range of cells, including immune cells like macrophages, B lymphocytes, T lymphocytes and mast cells, as well as endothelial cells, fibroblasts, and various stromal cells.

Cytokines act through receptors, and are important in health and disease, specifically in host responses to infection, immune responses, inflammation, trauma, sepsis, cancer, and reproduction. Chemokines mediate chemoattraction (chemotaxis) between cells.

Cytokines are thought to play key roles both in the immune response to cancer and the pathology of cancer. Cytokines directly stimulate immune effector cells and stromal cells at the tumour site and enhance tumour cell recognition by cytotoxic effector cells. Numerous animal tumour model studies have demonstrated that cytokines have broad anti-tumor activity and this has been translated into a number of cytokine-based approaches for cancer therapy. Recent years have seen a number of cytokines, including GM-CSF, IL-7, IL-12, IL-15, IL-18 and IL-21, enter clinical trials for patients with advanced cancer.

There is ongoing pre-clinical work supporting the neutralization of suppressive cytokines, such as IL-10 and TGF-β in promoting anti-tumour immunity. An advantage of targeting an immune-suppressive cytokine with a CAR cell of the present invention is that the CAR is effective in two ways: firstly by being activated by a cytokine which is characteristic of the disease and secondly by sequestering at least a protein of the circulating cytokine, thereby lessening its immune-suppressive effect.

The soluble ligand may be associated with the presence or pathology of a particular disease, such as cancer.

The soluble ligand may be part of the cancer secretome, i.e. the collection of factors secreted by a tumour, be it from cancer stem cells, non-stem cells or the surrounding stroma. The soluble ligand may be secreted by tumour cells. The soluble ligand may, for example, be selected from the following group: TGFβ, PSA, CEA and VEGF.

The soluble ligand may be characteristic of a disease or of diseased tissue. It may be found exclusively, or at a higher level in a subject having the disease vs a healthy subject; or in diseased tissue vs healthy tissue. The soluble ligand may be expressed at at least a 2-fold, 5-fold, 10-fold, 100-fold, 1000-fold, 10,000-fold or 100,000 fold higher level a subject having the disease vs a healthy subject; or in diseased tissue vs healthy tissue.

TGF Beta

The soluble ligand may be TGFβ.

Transforming growth factor beta (TGF-β) is a secreted protein that controls proliferation, cellular differentiation, and other functions in cells. It is a cytokine which plays a role in immunity and various diseases including cancer, bronchial asthma, lung fibrosis, heart disease, diabetes, Multiple Sclerosis and AIDS.

TGF-β is secreted by many cell types, including macrophages, in a latent form in which it is complexed with two other polypeptides, latent TGF-beta binding protein (LTBP) and latency-associated peptide (LAP). Serum proteinases such as plasmin catalyze the release of active TGF-β from the complex. This often occurs on the surface of macrophages where the latent TGF-β complex is bound to CD36 via its ligand, thrombospondin-1 (TSP-1). Inflammatory stimuli that activate macrophages enhance the release of active TGF-β by promoting the activation of plasmin. Macrophages can also endocytose IgG-bound latent TGF-β complexes that are secreted by plasma cells and then release active TGF-β into the extracellular fluid.

TGF-β exists in at least three isoforms: TGF-β1, TGF-β2 and TGF-β3. Information on the sequence and characteristics of TGF-β1, TGF-β2 and TGF-β3 are available from omim.org, entries 190180, 190220 and 190230 respectively.

TGF-β acts as an antiproliferative factor in normal epithelial cells and at early stages of oncogenesis. Cancerous cells increase their production of TGF-β, which also acts on surrounding cells.

In normal cells, TGF-β, acting through its signaling pathway, stops the cell cycle at the G1 stage to stop proliferation, induce differentiation, or promote apoptosis. When a cell is transformed into a cancer cell, parts of the TGF-β signaling pathway are mutated, and TGF-β no longer controls the cell. These cancer cells proliferate. The surrounding stromal cells (fibroblasts) also proliferate. Both cells increase their production of TGF-β. This TGF-β acts on the surrounding stromal cells, immune cells, endothelial and smooth-muscle cells. It causes immunosuppression and angiogenesis, which makes the cancer more invasive. TGF-β also converts effector T-cells, which normally attack cancer with an inflammatory (immune) reaction, into regulatory (suppressor) T-cells, which turn off the inflammatory reaction.

TGF-β is therefore an attractive target for the soluble ligand-recognising CAR of the present invention because a) upregulated expression of TGF-β is characteristic of a number of cancers; and b) sequestering free TGF-β by a CAR-expressing cell may reduce the amount of TGF-β in circulation and its associated immunosuppressive, angiogenic and anti-inflammatory effects.

The first or second CAR of the cell of the invention may comprise a binding domain based on fresolimumab.

Fresolimumab (GC1008) is a human monoclonal antibody which binds to and inhibits all isoforms of the TGF-β. Fresolimumab has been used in the treatment of idiopathic pulmonary fibrosis (IPF), focal segmental glomerulosclerosis, and cancer e.g. kidney cancer and melanoma.

The antigen-binding domain of first or second CAR may, for example, comprise the 6 CDRs or the VH and/or VL domain(s) from Fresolimumab.

Prostate-Specific Antigen (PSA)

The soluble ligand may be prostate-specific antigen (PSA).

Prostate-specific antigen (PSA), also known as gamma-seminoprotein or kallikrein-3 (KLK3), is a glycoprotein enzyme encoded in humans by the KLK3 gene. PSA is a member of the kallikrein-related peptidase family and is secreted by the epithelial cells of the prostate gland.

PSA is present in small quantities in the serum of men with healthy prostates, but is elevated in individuals with prostate cancer and other prostate disorders.

PSA is a 237-residue glycoprotein and is activated by KLK2. Its physiological role is the liquefaction of the coagulum components of the semen leading to liberation of spermatozoa. In cancer, PSA may participate in the processes of neoplastic growth and metastasis.

PSA is a chymotrypsin-like serine protease with a typical His-Asp-Ser triad and a catalytic domain similar to those of other kallikrein-related peptidases. The crystal structure of PSA has been obtained i) in complex with the monoclonal antibody (mAb) 8G8F5 and ii) in a sandwich complex with two mAbs 5D5A5 and 5D3D11 (Stura et al (J. Mol. Biol. (2011) 414:530-544).

Various monoclonal antibodies are known, including clones 2G2-B2, 2D8-E8, IgG1/K described in Bavat et al Avicenna J. Med. Biotechnol. 2015, 7:2-7; and . . . Leinonen (2004) 289:157-67

The antigen-binding domain of first or second CAR may, for example, comprise the 6 CDRs or the VH and/or VL domain(s) from a PSA-binding mAb such as 8G8F5, 5D5A5 or 5D3D11

The amino acid sequences for 5D3D11 and 5D5A5 VH and VL are given below. The complementarity determining regions (CDRs) are highlighted in bold.

5D3D11 VH
(SEQ ID No. 1)
QVQLQQSGPELVKPGASVKISCKVSGYAISSSWMNWVKQRPGQGLEWIGR

IYPGDGDTKYNGKFKDKATLTVDKSSSTAYMQLSSLTSVDSAVYFCARDG

YRYYFDYWGQGTSVTVSS

5D3D11 VL
(SEQ ID No. 2)
DIVMTQTAPSVFVTPGESVSISCRSSKSLLHSNGNTYLYWFLQRPGQSPQ

LLIYRMSNLASGVPDRFSGSGSGTDFTLRISRVEAEDVGVYYCMQHLEYP

VTFGAGTKVEIK

5D5A5 VH
(SEQ ID No. 3)
QVQLQQSGAELAKPGASVKMSCKTSGYSFSSYWMHWVKQRPGQGLEWIGY

INPSTGYTENNQKFKDKVTLTADKSSNTAYMQLNSLTSEDSAVYYCARSG

RLYFDVWGAGTTVTVSS

5D5A5 VL
(SEQ ID No. 4)
DIVLTQSPPSLAVSLGQRATISCRASESIDLYGFTFMHWYQQKPGQPPKI

LIYRASNLESGIPARFSGSGSRTDFTLTINPVEADDVATYYCQQTHEDPY

TFGGGTKLEIK

The antigen-binding domain of the first CAR may comprise the 6 CDRs from 5D5A5 and the antigen-binding domain of the second CAR may comprise the 6 CDRs from 5D3D11.

The antigen-binding domain of the first CAR may comprise the VH and/or VL domain(s) from 5D5A5 or a variant thereof; and the antigen-binding domain of the second CAR may comprise the VH and/or VL domain(s) from 5D3D11 or a variant thereof. Variant VH and VL domains may have at least 80, 90, 95 or 99% identity to the sequences given above, provided that they retain PSA-binding activity.

Carcinoembryonic Antigen (CEA)

The soluble ligand may be CEA.

Carcinoembryonic antigen (CEA) describes a set of highly related glycoproteins involved in cell adhesion. CEA is normally produced in gastrointestinal tissue during fetal development, but the production stops before birth. Therefore CEA is usually present only at very low levels in the blood of healthy adults. However, the serum levels are raised in some types of cancer, which means that it can be used as a tumor marker in clinical tests.

CEA are glycosyl phosphatidyl inositol (GPI) cell surface anchored glycoproteins whose specialized sialofucosylated glycoforms serve as functional colon carcinoma L-selectin and E-selectin ligands, which may be critical to the metastatic dissemination of colon carcinoma cells. Immunologically they are characterized as members of the CD66 cluster of differentiation.

CEA and related genes make up the CEA family belonging to the immunoglobulin superfamily. In humans, the carcinoembryonic antigen family consists of 29 genes, 18 of which are normally expressed. The following is a list of human genes which encode carcinoembryonic antigen-related cell adhesion proteins: CEACAM1, CEACAM3, CEACAM4, CEACAM5, CEACAM6, CEACAM7, CEACAM8, CEACAM16, CEACAM18, CEACAM19, CEACAM20, CEACAM21

Various antibodies which target CEA are described in WO 2011/034660.

Vascular Endothelial Growth Factor (VEGF)

The soluble ligand may be VEGF.

Vascular endothelial growth factor (VEGF) is a signal protein produced by cells that stimulates vasculogenesis and angiogenesis. It is part of the system that restores the oxygen supply to tissues when blood circulation is inadequate. Serum concentration of VEGF is high in bronchial asthma and diabetes mellitus. VEGF's normal function is to create new blood vessels during embryonic development, new blood vessels after injury, muscle following exercise, and new vessels (collateral circulation) to bypass blocked vessels.

When VEGF is overexpressed, it can contribute to disease. Solid cancers cannot grow beyond a limited size without an adequate blood supply; cancers that can express VEGF are able to grow and metastasize.

VEGF is a sub-family of the platelet-derived growth factor family of cystine-knot growth factors. They are important signaling proteins involved in both vasculogenesis (the de novo formation of the embryonic circulatory system) and angiogenesis (the growth of blood vessels from pre-existing vasculature).

The VEGF family comprises in mammals five members: VEGF-A, placenta growth factor (PGF), VEGF-B, VEGF-C and VEGF-D.

Various antibodies to VEGF are known, such as bevacizumab (Avastin) and Ranibizumab (Lucentis).

Membrane Bound Ligands

The term "membrane-bound ligand" is used to indicate a ligand or antigen which is part of or attached to a cell. The ligand may be expressed at the surface of a target cell. The ligand may, for example be a transmembrane protein.

The antigen binding domain may bind a TAA which is expressed on a cell, for example a cancer cell, at a low density. A TAA expressed at low density may refer, for example, to a TAA expressed at a level of 10s to 1000s molecules per cell.

Examples of TAAs which are known to be expressed at low densities in certain cancers include, but are not limited to, ROR1 in CLL, Typr-1 in melanoma and BCMA in myeloma.

Antigen-binding domains (such as scFvs or mAbs) which bind these TAAs have previously been described, for example as shown in the following Table 1.

TABLE 1

| Tumour-associated antigen | Antigen-binding domain | Reference |
| --- | --- | --- |
| ROR-1 | 2A2, 2D11 | S. Baskar et al., Landes Bioscience, vol. 4, (3) 349-361), R12, R11, Y31 (J. Yang et al., PLOSone, vol. 6, (6), e21018, 2011 |
| Tyrp-1 | TA99 | P. Boross et al., Immunology Letters, vol. 160, (2), 151-157, 2014 |
| BCMA | C12A3.2 and C11D5.3 | R. Carpenter et al., Clin Cancer Res., vol. 19, (8) 2048-2060, 2013), J6M0 (Y. Tai et al., Blood, vol 123, (20), 3128-3138, 2014 |

Spacer

The CARs of the present invention may comprise a spacer sequence to connect the antigen-binding domain with the transmembrane domain and spatially separate the antigen-binding domain from the endodomain. A flexible spacer allows to the antigen-binding domain to orient in different directions to enable antigen binding.

The spacer of the first CAR may be different from the spacer of the second CAR.

The spacer sequence may, for example, comprise an IgG1 Fc region, an IgG1 hinge or a CD8 stalk. The linker may alternatively comprise an alternative linker sequence which has similar length and/or domain spacing properties as an IgG1 Fc region, an IgG1 hinge or a CD8 stalk.

A human IgG1 spacer may be altered to remove Fc binding motifs.

Examples of amino acid sequences for these spacers are given below:

SEQ ID No. 5 (hinge-CH2CH3 of human IgG1):
AEPKSPDKTHTCPPCPAPPVAGPSVFLFPPKPKDTLMIARTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKKD

SEQ ID No. 6 (human CD8 stalk):
TTTPAPRPPTPAPTIASQPLSLRPEACRPAAGGAVHTRGLDFACDI

SEQ ID No. 7 (human IgG1 hinge):
AEPKSPDKTHTCPPCPKDPK

Coiled Coil Domain

The first and/or second CAR of cell of the present invention may comprise a coiled coil spacer domain.

Figure 6:
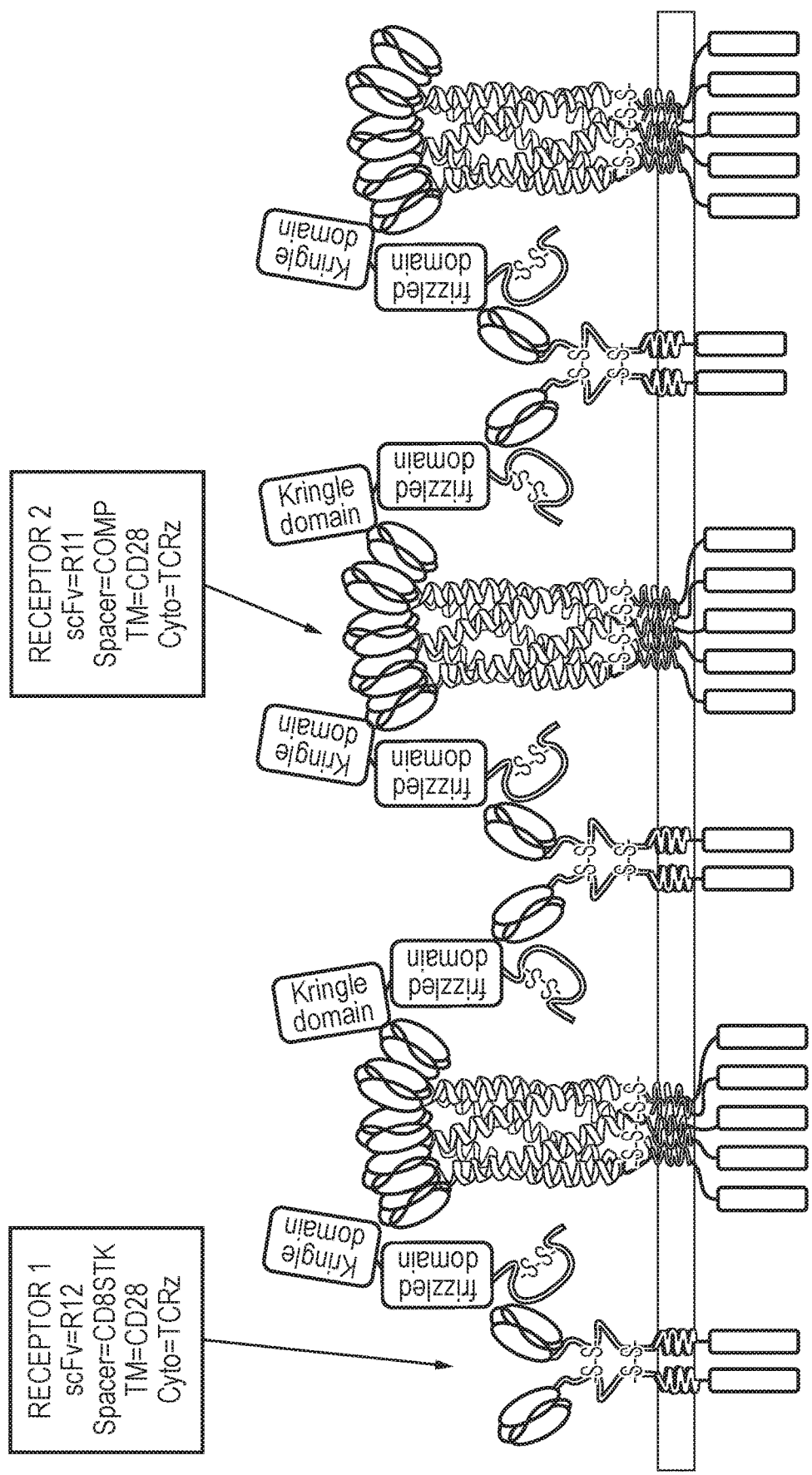
FIG. 6: A schematic diagram illustrating the predicted aggregation with ROR-1 using the model system tested in the Examples where one CAR is multivalent.

A coiled coil is a structural motif in which two to seven alpha-helices are wrapped together like the strands of a rope (FIG. 6). Many endogenous proteins incorporate coiled coil domains. The coiled coil domain may be involved in protein folding (e.g. it interacts with several alpha helical motifs within the same protein chain) or responsible for protein-protein interaction. In the latter case, the coiled coil can initiate homo or hetero oligomer structures.

As used herein, the terms 'multimer' and 'multimerization' are synonymous and interchangeable with 'oligomer' and 'oligomerization'.

The structure of coiled coil domains is well known in the art. For example as described by Lupas & Gruber (Advances in Protein Chemistry; 2007; 70; 37-38).

Coiled coils usually contain a repeated pattern, hxxhcxc, of hydrophobic (h) and charged (c) amino-acid residues, referred to as a heptad repeat. The positions in the heptad repeat are usually labeled abcdefg, where a and d are the hydrophobic positions, often being occupied by isoleucine, leucine, or valine. Folding a sequence with this repeating pattern into an alpha-helical secondary structure causes the hydrophobic residues to be presented as a 'stripe' that coils gently around the helix in left-handed fashion, forming an amphipathic structure. The most favourable way for two such helices to arrange themselves in the cytoplasm is to wrap the hydrophobic strands against each other sandwiched between the hydrophilic amino acids. Thus, it is the burial of hydrophobic surfaces that provides the thermodynamic driving force for the oligomerization. The packing in a coiled-coil interface is exceptionally tight, with almost complete van der Waals contact between the side-chains of the a and d residues.

The α-helices may be parallel or anti-parallel, and usually adopt a left-handed super-coil. Although disfavored, a few right-handed coiled coils have also been observed in nature and in designed proteins The coiled coil domain may be any coiled coil domain which is capable of forming a coiled coil multimer such that a complex of CARs comprising the coiled coil domain is formed.

The relationship between the sequence and the final folded structure of a coiled coil domain are well understood in the art (Mahrenholz et al; Molecular & Cellular Proteomics; 2011; 10(5):M110.004994). As such the coiled coil domain may be a synthetically generated coiled coil domain.

Examples of proteins which contain a coiled coil domain include, but are not limited to, kinesin motor protein, hepatitis D delta antigen, archaeal box C/D sRNP core protein, cartilage-oligomeric matrix protein (COMP), mannose-binding protein A, coiled-coil serine-rich protein 1, polypeptide release factor 2, SNAP-25, SNARE, Lac repressor or apolipoprotein E.

The sequence of various coiled coil domains is shown below:

```
Kinesin motor protein: parallel homodimer
                                       (SEQ ID No. 8)
MHAALSTEVVHLRQRTEELLRCNEQQAAELETCKEQLFQSNMERKELHNT

VMDLRGN

Hepatitis D delta antigen: parallel homodimer
                                       (SEQ ID No. 9)
GREDILEQWVSGRKKLEELERDLRKLKKKIKKLEEDNPWLGNIKGIIGKY Archaeal box C/D sRNP core protein: anti-parallel
heterodimer
                                      (SEQ ID No. 10)
RYVVALVKALEEIDESINMLNEKLEDIRAVKESEITEKFEKKIRELRELR

RDVEREIEEVM

Mannose-binding protein A: parallel homotrimer
                                      (SEQ ID No. 11)
AIEVKLANMEAEINTLKSKLELTNKLHAFSM Coiled-coil serine-rich protein 1: parallel
homotrimer
                                      (SEQ ID No. 12)
EWEALEKKLAALESKLQALEKKLEALEHG Polypeptide release factor 2: anti-parallel
heterotrimer
Chain A:
                                      (SEQ ID No. 13)
INPVNNRIQDLTERSDVLRGYLDY Chain B:
                                      (SEQ ID No. 14)
VVDTLDQMKQGLEDVSGLLELAVEADDEETFNEAVAELDALEEKLAQLEF

R

SNAP-25 and SNARE: parallel heterotetramer
Chain A:
                                      (SEQ ID No. 15)
IETRHSEIIKLENSIRELHDMFMDMAMLVESQGEMIDRIEYNVEHAVDYV

E

Chain B:
                                      (SEQ ID No. 16)
ALSEIETRHSEIIKLENSIRELHDMFMDMAMLVESQGEMIDRIEYNVEHA

VDYVERAVSDTKKAVKY

Chain C:
                                      (SEQ ID No. 17)
ELEEMQRRADQLADESLESTRRMLQLVEESKDAGIRTLVMLDEQGEQLER

IEEGMDQINKDMKEAEKNL

Chain D:
                                      (SEQ ID No. 18)
IETRHSEIIKLENSIRELHDMFMDMAMLVESQGEMIDRIEYNVEHAVDYV

E

Lac repressor: parallel homotetramer
                                      (SEQ ID No. 19)
SPRALADSLMQLARQVSRLE Apolipoprotein E: anti-parallel heterotetramer
                                      (SEQ ID No. 20)
SGQRWELALGRFWDYLRWVQTLSEQVQEELLSSQVTQELRALMDETMKEL

KAYKSELEEQLTARLSKELQAAQARLGADMEDVCGRLVQYRGEVQAMLGQ

STEELRVRLASHLRKLRKRLLRDADDLQKRLAVYQA
```

A coiled coil domain is capable of oligomerization. The coiled coil domain may be capable of forming a dimer, a trimer, a tetramer, a pentamer, a hexamer or a heptamer.

Examples of coiled coil domains which are capable of forming multimers comprising more than two coiled coil domains include, but are not limited to, those from cartilage-oligomeric matrix protein (COMP), mannose-binding protein A, coiled-coil serine-rich protein 1, polypeptide release factor 2, SNAP-25, SNARE, Lac repressor or apolipoprotein E (see SEQ ID Nos. 11-20 above).

The coiled coil domain may be the COMP coiled coil domain.

COMP is one of the most stable protein complexes in nature (stable from 0° C.-100° C. and a wide range of pH) and can only be denatured with 4-6M guanidine hydrochloride. The COMP coiled coil domain is capable of forming a pentamer. COMP is also an endogenously expressed protein that is naturally expressed in the extracellular space. This reduces the risk of immunogenicity compared to synthetic spacers. Furthermore, the crystal structure of the COMP coiled coil motif has been solved which gives an accurate estimation on the spacer length. The COMP structure is ~5.6 nm in length (compared to the hinge and CH2CH3 domains from human IgG which is ~8.1 nm).

The coiled coil domain may consist of or comprise the sequence shown as SEQ ID No. 21 or a fragment thereof.

```
                                      SEQ ID No. 21
DLGPQMLRELQETNAALQDVRELLRQQVREITFLKNTVMECDACG
```

It is possible to truncate the COMP coiled-coil domain at the N-terminus and retain surface expression. The coiled-coil domain may therefore comprise or consist of a truncated version of SEQ ID No. 21, which is truncated at the N-terminus. The truncated COMP may comprise the 5 C-terminal amino acids of SEQ ID No. 21, i.e. the sequence CDACG. The truncated COMP may comprise 5 to 44 amino acids, for example, at least 5, 10, 15, 20, 25, 30, 35 or 40 amino acids. The truncated COMP may correspond to the C-terminus of SEQ ID No. 21. For example a truncated COMP comprising 20 amino acids may comprise the sequences QQVREITFLKNTVMECDACG. Truncated COMP may retain the cysteine residue(s) involved in multimerisation. Truncated COMP may retain the capacity to form multimers.

Various coiled coil domains are known which form hexamers such as gp41 derived from HIV, and an artificial protein designed hexamer coiled coil described by N. Zaccai et al. (2011) Nature Chem. Bio., (7) 935-941). A mutant form of the GCN4-p1 leucine zipper forms a heptameric coiled-coil structure (J. Liu. et al., (2006) PNAS (103) 15457-15462).

The coiled coil domain may comprise a variant of one of the coiled coil domains described above, providing that the variant sequence retains the capacity to form a coiled coil oligomer. For example, the coiled coil domain may comprise a variant of the sequence shown as SEQ ID No. 8 to 21 having at least 80, 85, 90, 95, 98 or 99% sequence identity, providing that the variant sequence retains the capacity to form a coiled coil oligomer.

The percentage identity between two polypeptide sequences may be readily determined by programs such as BLAST which is freely available at http://blast.ncbi.nlm.nih.gov.

Transmembrane Domain

The transmembrane domain is the sequence of a CAR that spans the membrane. It may comprise a hydrophobic alpha helix. The transmembrane domain may be derived from CD28, which gives good receptor stability.

Signal Peptide

The CARs of the present invention may comprise a signal peptide so that when they are expressed in a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the sequence shown as SEQ ID No. 22, 23 or 24 or a variant thereof having 5, 4, 3, 2 or 1 amino acid mutations (insertions, substitutions or additions) provided that the signal peptide still functions to cause cell surface expression of the CAR.

```
SEQ ID No. 22:
MGTSLLCWMALCLLGADHADG
```

The signal peptide of SEQ ID No. 22 is compact and highly efficient and is derived from TCR beta chain. It is predicted to give about 95% cleavage after the terminal glycine, giving efficient removal by signal peptidase.

```
SEQ ID No. 23:
MSLPVTALLLPLALLLHAARP
```

The signal peptide of SEQ ID No. 23 is derived from IgG1.

```
SEQ ID No. 24:
MAVPTQVLGLLLLWLTDARC
```

The signal peptide of SEQ ID No. 24 is derived from CD8a.

Endodomain

The endodomain is the portion of a classical CAR which is located on the intracellular side of the membrane.

The endodomain is the signal-transmission portion of a classical CAR. After antigen recognition by the antigen binding domain, individual CAR molecules cluster, native CD45 and CD148 are excluded from the synapse and a signal is transmitted to the cell.

The endodomain of the first, second or third CAR as defined herein may be or comprise an intracellular signalling domain. In an alternative embodiment, the endodomain of the present CAR may be capable of interacting with an intracellular signalling molecule which is present in the cytoplasm, leading to signalling.

The intracellular signalling domain or separate intracellular signalling molecule may be or comprise a T cell signalling domain.

The most commonly used signalling domain component is that of CD3-zeta endodomain, which contains 3 ITAMs. This transmits an activation signal to the T cell after antigen is bound. CD3-zeta may not provide a fully competent activation signal and additional co-stimulatory signalling may be needed. For example, chimeric CD28 and OX40 can be used with CD3-Zeta to transmit a proliferative/survival signal, or all three can be used together.

The present CAR may comprise the CD3-Zeta endodomain alone, the CD3-Zeta endodomain with that of either CD28 or OX40 or the CD28 endodomain and OX40 and CD3-Zeta endodomain.

The endodomain may comprise one or more of the following: an ICOS endodomain, a CD27 endodomain, a BTLA endodomain, a CD30 endodomain, a GITR endodomain and an HVEM endodomain.

The endomain may comprise the sequence shown as SEQ ID No. 25 to 33 or a variant thereof having at least 80% sequence identity.

```
- CD3 Z endodomain
                                   SEQ ID No. 25
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

- CD28 and CD3 Zeta endodomains
                                   SEQ ID No. 26
SKRSRLLHSDYMNMTPRRPGPTRKHYQPYAPPRDFAAYRSRVKFSRSADA

PAYQQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALP

PR

- CD28, OX40 and CD3 Zeta endodomains
                                   SEQ ID No. 27
SKRSRLLHSDYMNMTPRRPGPTRKHYQPYAPPRDFAAYRSRDQRLPPDAH

KPPGGGSFRTPIQEEQADAHSTLAKIRVKFSRSADAPAYQQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR

- ICOS endodomain
                                   SEQ ID No. 28
CWLTKKKYSSSVHDPNGEYMFMRAVNTAKKSRLTDVTL

- CD27 endodomain
                                   SEQ ID No. 29
QRRKYRSNKGESPVEPAEPCHYSCPREEEGSTIPIQEDYRKPEPACSP

- BTLA endodomain
                                   SEQ ID No. 30
RRHQGKQNELSDTAGREINLVDAHLKSEQTEASTRQNSQVLLSETGIYDN

DPDLCFRMQEGSEVYSNPCLEENKPGIVYASLNHSVIGPNSRLARNVKEA

PTEYASICVRS

- CD30 endodomain
                                   SEQ ID No. 31
HRRACRKRIRQKLHLCYPVQTSQPKLELVDSRPRRSSTQLRSGASVTEPV

AEERGLMSQPLMETCHSVGAAYLESLPLQDASPAGGPSSPRDLPEPRVST

EHTNNKIEKIYIMKADTVIVGTVKAELPEGRGLAGPAEPELEEELEADHT

PHYPEQETEPPLGSCSDVMLSVEEEGKEDPLPTAASGK

- GITR endodomain
                                   SEQ ID No. 32
QLGLHIWQLRSQCMWPRETQLLLEVPPSTEDARSCQFPEEERGERSAEEK

GRLGDLWV
```

-continued

- HVEM endodomain

SEQ ID No. 33
CVKRRKPRGDVVKVIVSVQRKRQEAEGEATVIEALQAPPDVTTVAVEETI
PSFTGRSPNH

A variant sequence may have at least 80%, 85%, 90%, 95%, 98% or 99% sequence identity to SEQ ID No. 25 to 33, provided that the sequence provides an effective intracellular signalling domain.

Subsequent CAR(s)

In addition to the first and second CARs defined above, the cell of the invention may comprise third and optionally subsequent CARs (fourth, fifth, sixth etc).

A third CAR may, for example, bind a cell surface antigen, such as a tumour associated antigen.

Various tumour associated antigens (TAA) are known, as shown in the following Table 2. The antigen-binding domain of the third or subsequent CAR may be a domain which is capable of binding one of these TAAs.

TABLE 2

| Cancer type | TAA |
| --- | --- |
| Diffuse Large B-cell Lymphoma | CD19, CD20, CD22 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSMA |
| Bowel cancer | A33 |

Nucleic Acid

The present invention further provides a nucleic acid construct which comprises a first nucleic acid sequence encoding a first CAR as defined in connection with the first aspect of the invention; and a second nucleic acid sequence encoding a second CAR as defined in connection with the first aspect of the invention.

The nucleic acid construct may have the following structure:

AgB1-spacer1-TM1-endo1-coexpr-AbB2-spacer2-TM2-endo2 in which

AgB1 is a nucleic acid sequence encoding the antigen-binding domain of the first CAR;

spacer 1 is a nucleic acid sequence encoding the spacer of the first CAR;

TM1 is a nucleic acid sequence encoding the transmembrane domain of the first CAR;

endo 1 is a nucleic acid sequence encoding the endodomain of the first CAR;

coexpr is a nucleic acid sequence enabling co-expression of both CARs

AgB2 is a nucleic acid sequence encoding the antigen-binding domain of the second CAR;

spacer 2 is a nucleic acid sequence encoding the spacer of the second CAR;

TM2 is a nucleic acid sequence encoding the transmembrane domain of the second CAR;

endo 2 is a nucleic acid sequence encoding the endodomain of the second CAR.

When the nucleic acid construct is expressed in a cell, such as a T-cell, it encodes a polypeptide which is cleaved at the cleavage site such that the first and second CARs are co-expressed at the cell surface.

Where the nucleic acid construct encodes three CARs, it may have the structure:

AgB1-spacer1-TM1-endo1-coexpr1-AbB2-spacer2-TM2-endo2-coexpr2-AbB3-spacer3-TM3-endo3

The endodomain may be an intracellular cell signalling domain or may associate intracellularly with a separate cell signalling domain.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

In the structure above, "coexpr" is a nucleic acid sequence enabling co-expression of both first and second CARs. It may be a sequence encoding a cleavage site, such that the nucleic acid construct produces comprises two or more CARs joined by a cleavage site(s). The cleavage site may be self-cleaving, such that when the polypeptide is produced, it is immediately cleaved into individual peptides without the need for any external cleavage activity.

The cleavage site may be any sequence which enables the first and second CARs to become separated.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode proteins, causes the proteins to be expressed as separate entities.

The cleavage site may be a furin cleavage site.

Furin is an enzyme which belongs to the subtilisin-like proprotein convertase family. The members of this family are proprotein convertases that process latent precursor proteins into their biologically active products. Furin is a calcium-dependent serine endoprotease that can efficiently cleave precursor proteins at their paired basic amino acid processing sites. Examples of furin substrates include proparathyroid hormone, transforming growth factor beta 1 precursor, proalbumin, pro-beta-secretase, membrane type-1 matrix metalloproteinase, beta subunit of pro-nerve growth factor and von Willebrand factor. Furin cleaves proteins just downstream of a basic amino acid target sequence (canonically, Arg-X-(Arg/Lys)-Arg') and is enriched in the Golgi apparatus.

The cleavage site may be a Tobacco Etch Virus (TEV) cleavage site.

TEV protease is a highly sequence-specific cysteine protease which is chymotrypsin-like proteases. It is very specific for its target cleavage site and is therefore frequently used for the controlled cleavage of fusion proteins both in vitro and in vivo. The consensus TEV cleavage site is ENLYFQ\S (where '\' denotes the cleaved peptide bond). Mammalian cells, such as human cells, do not express TEV protease. Thus in embodiments in which the present nucleic acid construct comprises a TEV cleavage site and is expressed in a mammalian cell—exogenous TEV protease must also expressed in the mammalian cell.

The cleavage site may encode a self-cleaving peptide.

A 'self-cleaving peptide' refers to a peptide which functions such that when the polypeptide comprising the proteins and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus (Donelly et al (2001) as above).

"2A-like" sequences have been found in picornaviruses other than aptho- or cardioviruses, 'picornavirus-like' insect viruses, type C rotaviruses and repeated sequences within *Trypanosoma* spp and a bacterial sequence (Donnelly et al (2001) as above). The cleavage site may comprise one of these 2A-like sequences, such as:

```
YHADYYKQRLIHDVEMNPGP      (SEQ ID No. 34)

HYAGYFADLLIHDIETNPGP      (SEQ ID No. 35)

QCTNYALLKLAGDVESNPGP      (SEQ ID No. 36)

ATNFSLLKQAGDVEENPGP       (SEQ ID No. 37)

AARQMLLLLSGDVETNPGP       (SEQ ID No. 38)

RAEGRGSLLTCGDVEENPGP      (SEQ ID No. 39)

TRAEIEDELIRAGIESNPGP      (SEQ ID No. 40)

TRAEIEDELIRADIESNPGP      (SEQ ID No. 41)

AKFQIDKILISGDVELNPGP      (SEQ ID No. 42)

SSIIRTKMLVSGDVEENPGP      (SEQ ID No. 43)
```

```
-continued
CDAQRQKLLLSGDIEQNPGP      (SEQ ID No. 44)

YPIDFGGFLVKADSEFNPGP      (SEQ ID No. 45)
```

The cleavage site may comprise the 2A-like sequence shown as SEQ ID No. 39 (RAEGRGSLLTCGDVEENPGP).

The present invention also provides a kit comprising one or more nucleic acid sequence(s) encoding first and second CARs according to the first aspect of the present invention.

Split CAR Systems

Figure 9:
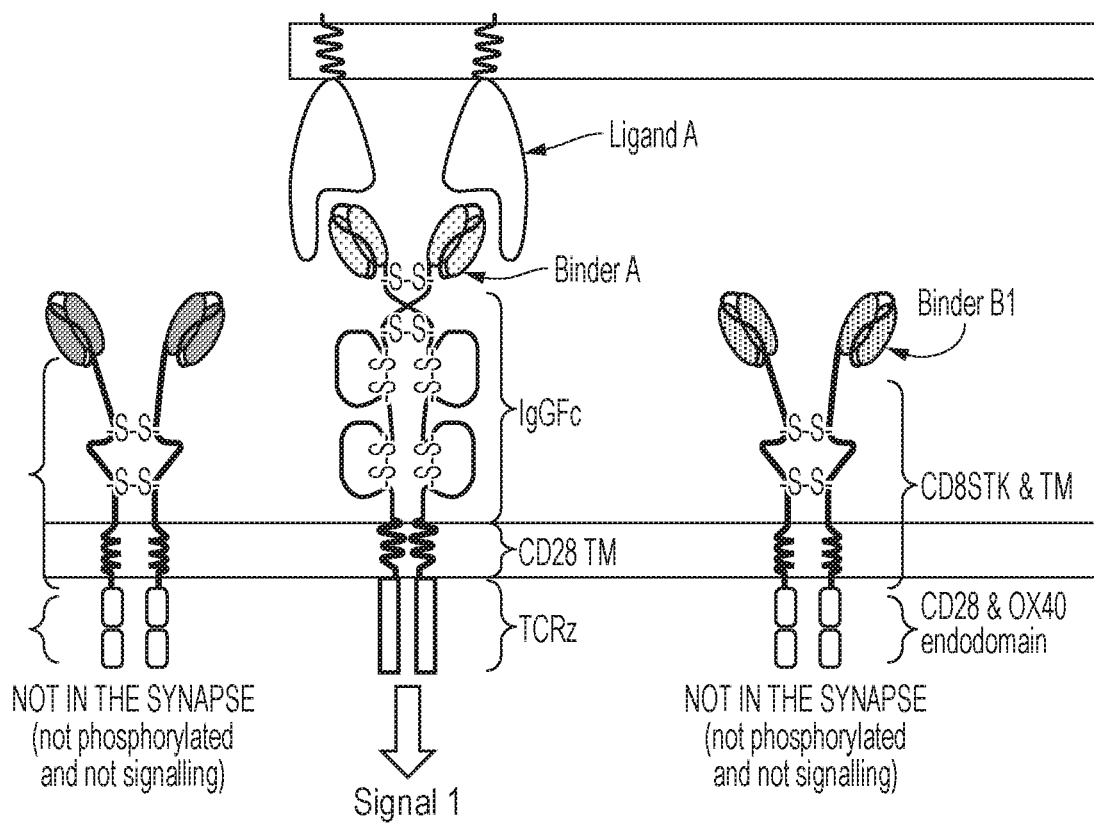
FIG. 9: A schematic diagram showing an example of a "split" CAR system. Binding of a cell surface antigen, such as PSMA, by the third CAR provides T-cell activatory signal 1 via the TCR zeta endodomain. Binding of a soluble ligand, such as PSA, by the first and second CARs provides T cell activatory signals 2 and 3 via CD28 and OX40 endodomains. The presence of both the cell surface antigen (eg PSMA) and the soluble ligand (e.g. PSA) provides all three signals and leads to T-cell activation.
Figure 9:
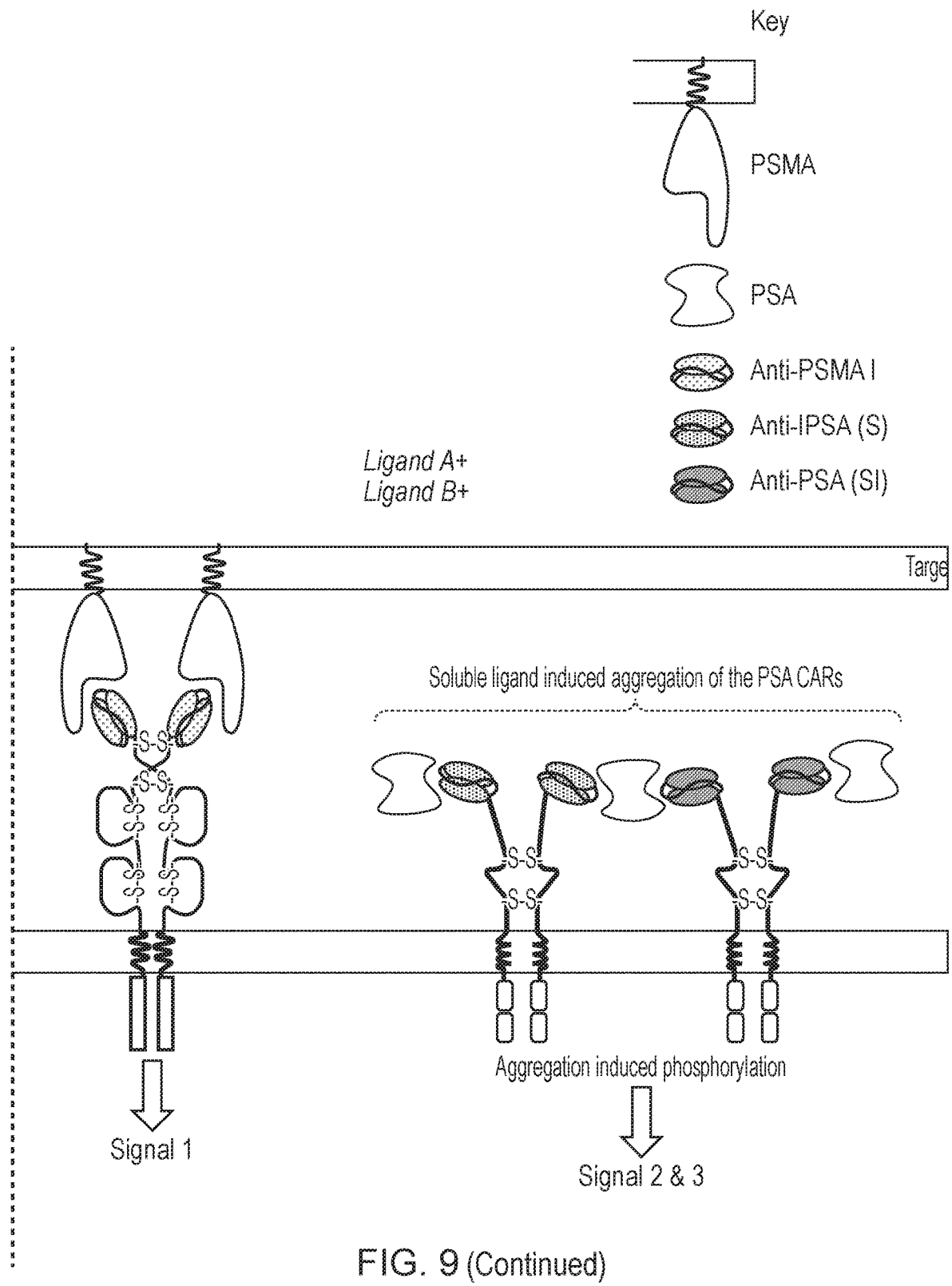

In one embodiment of the invention, the T-cell stimulating endodomains are "split" between the first and second CARs recognising a soluble ligand, and the third CAR recognising a cell-surface antigen (see FIG. 9).

An advantage of such a split-CAR system is that it avoids the possibility of the T-cell "shadow-boxing" i.e. trying to kill something that isn't there. This may occur if, for example, the soluble ligand is present in the vicinity of the T cell, but the tumour cell which secreted the soluble ligand is too far away to be killed by an activated T cell.

In this system, the endodomains may, for example, be split between the first and/or second CAR which bind the soluble ligand; and the third CAR which binds with cell-surface antigen, as shown in the following Table:

| Endodomain(s) on first and/or second CAR | Endodomain(s) on third CAR |
| --- | --- |
| CD28-OX40 or CD28-41BB | CD3 zeta |
| OX40 or 41BB | CD28-CD3 zeta |

In this embodiment of the invention the endodomains of the third CAR and the first and/or second CAR(s) are "complementary" in the sense that together, they provide signals 1 and 2 or 1, 2 and 3, leading to cell activation. Optimal T cell activation therefore occurs when the soluble ligand is bound by the first and second CARs and the cell surface antigen is bound by the third CAR.

In this embodiment, the third CAR may bind prostate-specific membrane antigen (PSMA) and the first and second CARs may bind prostate-specific antigen (PSA).

Aggregation-Based Inhibitory CAR System

Figure 10:
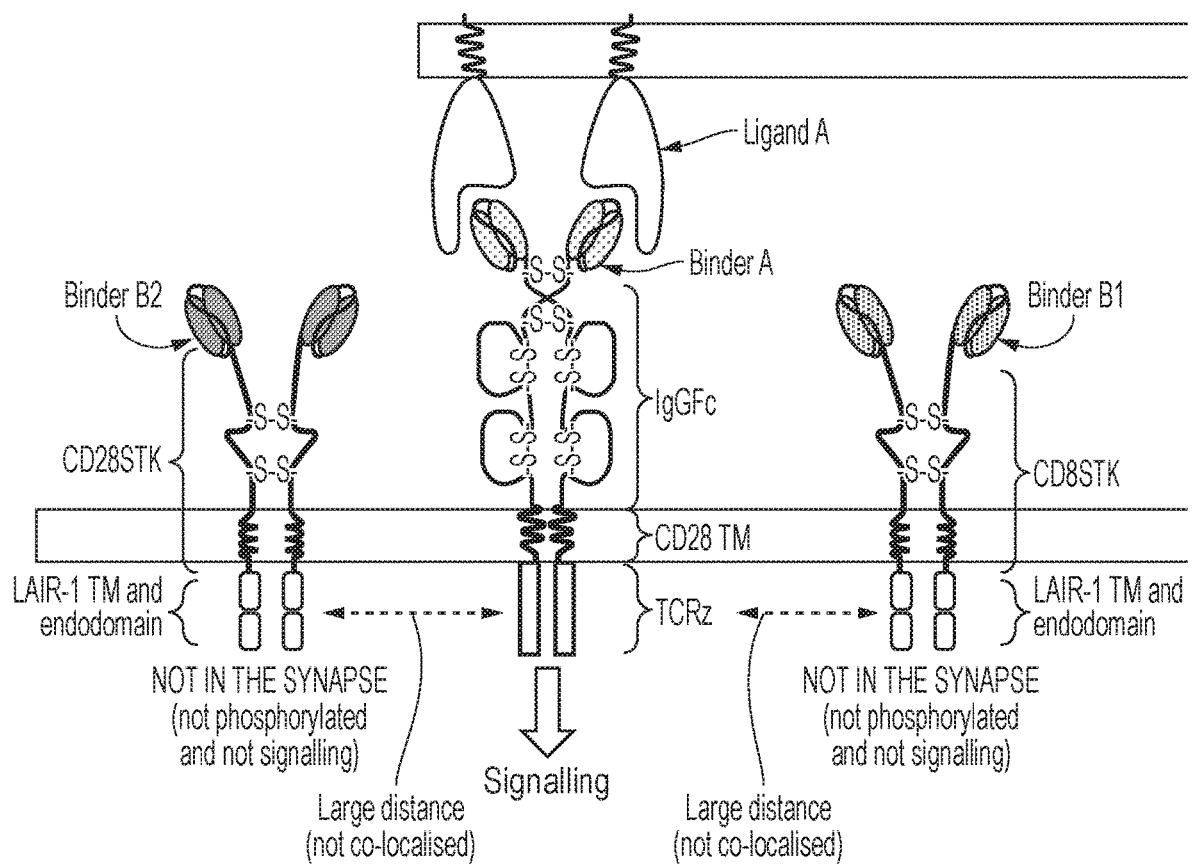
FIG. 10: A schematic diagram showing a CAR system, where the first and/or second CARs inhibit(s) signalling from the third CAR. Binding of a cell surface antigen ("Ligand A" e.g. PSMA) by the third CAR leads to T cell signalling. However, binding of a soluble ligand (e.g. IL6) by the first and second CARs leads to aggregation-induced phosphorylation and inhibition of signalling.
Figure 10:
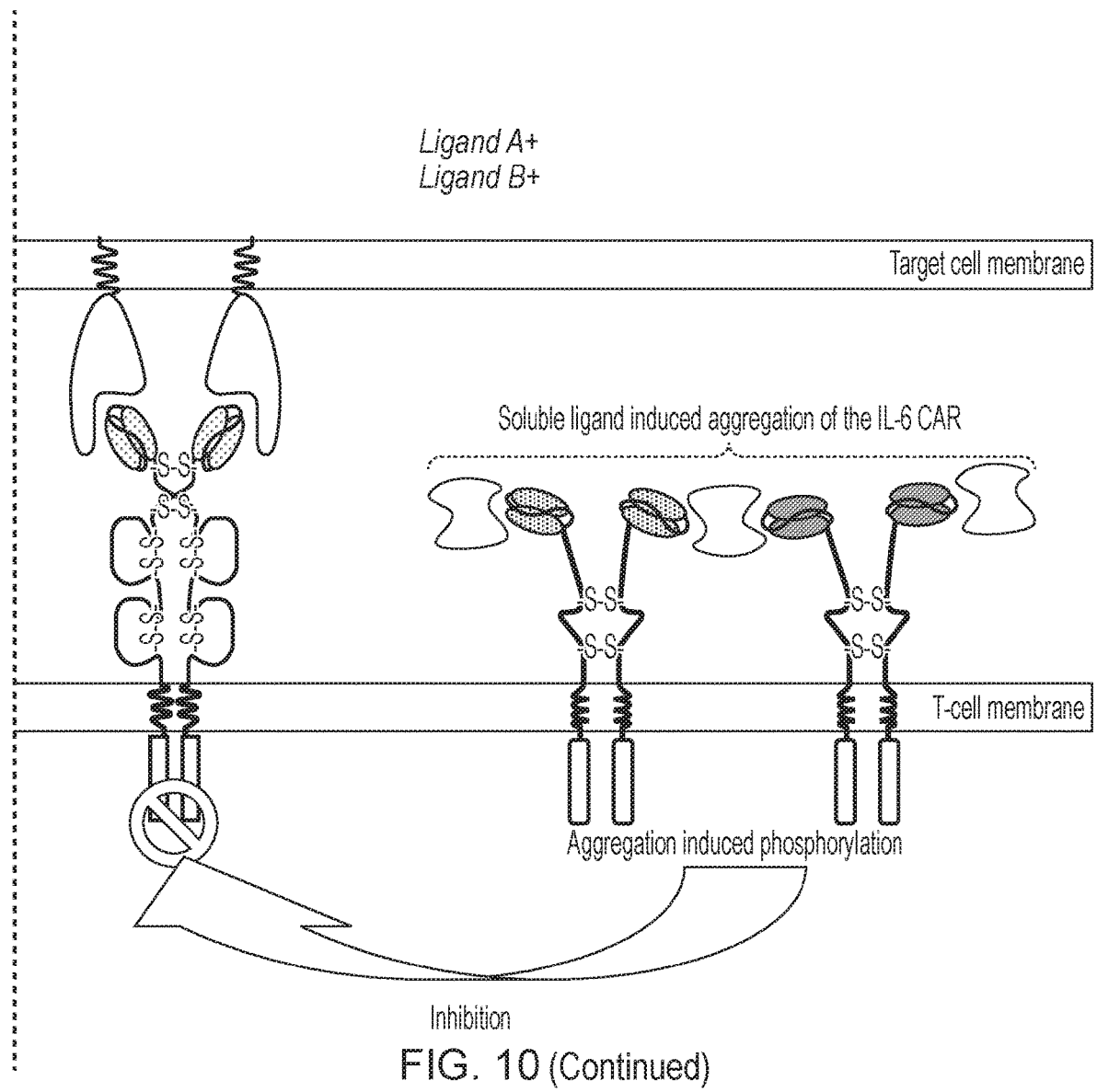

In a second embodiment of the invention, ligation of the ligand by the first and second CAR causes inhibition of the third CAR. Binding the cell surface antigen by the third CAR in the absence of ligand (eg soluble ligand) leads to cell activation. By contrast, binding the cell surface antigen by the third CAR in the presence of ligand (eg soluble ligand) does not lead to cell activation, or leads to reduced cell activation (See FIG. 10).

In this embodiment the soluble ligand may be an entity, such as a cytokine, which is released by normal tissue but not by cancerous tissue. The ligand may, for example, be IL-6. In this way, the inhibitory signal provided by the soluble CAR could be used to provide a negative feedback loop for CAR-associated problems such as cytokine release syndrome or mass-activation syndrome.

The first and/or second CAR comprise(s) a "ligation-on" inhibitory endodomain, such that when the first and second CARs bind the ligand, cell activation caused by the third CAR binding the cell surface antigen is inhibited.

The "ligation-on" inhibitory endodomain does not significantly inhibit T-cell activation by the third CAR in the absence of the soluble ligand, but inhibits T-cell activation by the third CAR when the first and second CARs bind the soluble ligand.

The "ligation-on" inhibitory endodomain may be or comprise a tyrosine phosphatase with a sufficiently slow catalytic rate for phosphorylated ITAMs that does not inhibit TCR signalling when only the third CAR binds its (cell surface) antigen. but it is capable of inhibiting the TCR signalling response when aggregation of the first and second CARs cause the inhibitory endodomains to be concentrated at the synapse.

The inhibitory endodomain may comprise all or part of a protein-tyrosine phosphatase such as PTPN6.

Protein tyrosine phosphatases (PTPs) are signaling molecules that regulate a variety of cellular processes including cell growth, differentiation, mitotic cycle, and oncogenic transformation. The N-terminal part of this PTP contains two tandem Src homolog (SH2) domains, which act as protein phospho-tyrosine binding domains, and mediate the interaction of this PTP with its substrates. This PTP is expressed primarily in hematopoietic cells, and functions as an important regulator of multiple signaling pathways in hematopoietic cells.

The inhibitor domain may comprise all of PTPN6 (SEQ ID No. 46) or just the phosphatase domain (SEQ ID No. 47).

- sequence of PTPN6
SEQ ID 46
MVRWFHRDLSGLDAETLLKGRGVHGSFLARPSRKNQGDFSLSVRVGDQVT

HIRIQNSGDFYDLYGGEKFATLTELVEYYTQQQGVLQDRDGTIIHLKYPL

NCSDPTSERWYHGHMSGGQAETLLQAKGEPWTFLVRESLSQPGDFVLSVL

SDQPKAGPGSPLRVTHIKVMCEGGRYTVGGLETFDSLTDLVEHFKKTGIE

EASGAFVYLRQPYYATRVNAADIENRVLELNKKQESEDTAKAGFWEEFES

LQKQEVKNLHQRLEGQRPENKGKNRYKNILPFDHSRVILQGRDSNIPGSD

YINANYIKNQLLGPDENAKTYIASQGCLEATVNDFWQMAWQENSRVIVMT

TREVEKGRNKCVPYWPEVGMQRAYGPYSVTNCGEHDTTEYKLRTLQVSPL

DNGDLIREIWHYQYLSWPDHGVPSEPGGVLSFLDQINQRQESLPHAGPII

VHCSAGIGRTGTIIVIDMLMENISTKGLDCDIDIQKTIQMVRAQRSGMVQ

TEAQYKFIYVAIAQFIETTKKKLEVLQSQKGQESEYGNITYPPAMKNAHA

KASRTSSKHKEDVYENLHTKNKREEKVKKQRSADKEKSKGSLKRK

- sequence of phosphatase domain of PTPN6
SEQ ID 47
FWEEFESLQKQEVKNLHQRLEGQRPENKGKNRYKNILPFDHSRVILQGRD

SNIPGSDYINANYIKNQLLGPDENAKTYIASQGCLEATVNDFWQMAWQEN

SRVIVMTTREVEKGRNKCVPYWPEVGMQRAYGPYSVTNCGEHDTTEYKLR

TLQVSPLDNGDLIREIWHYQYLSWPDHGVPSEPGGVLSFLDQINQRQESL

PHAGPIIVHCSAGIGRTGTIIVIDMLMENISTKGLDCDIDIQKTIQMVRA

QRSGMVQTEAQYKFIYVAIAQF

Alternatively the inhibitory endodomain may be an ITIM (Immunoreceptor Tyrosine-based Inhibition motif) containing endodomain such as that from CD22, LAIR-1, the Killer inhibitory receptor family (KIR), LILRB1, CTLA4, PD-1, BTLA etc. When phosphorylated, ITIMs recruits endogenous PTPN6 through its SH2 domain. If co-localised with an ITAM containing endodomain, dephosphorylation occurs and the activating CAR is inhibited.

An ITIM is a conserved sequence of amino acids (S/I/V/LxYxxl/V/L) that is found in the cytoplasmic tails of many inhibitory receptors of the immune system. One skilled in the art can easily find protein domains containing an ITIM. A list of human candidate ITIM-containing proteins has been generated by proteome-wide scans (Staub, et al (2004) Cell. Signal. 16, 435-456). Further, since the consensus sequence is well known and little secondary structure appears to be required, one skilled in the art could generate an artificial ITIM.

ITIM endodomains from PDCD1, BTLA4, LILRB1, LAIR1, CTLA4, KIR2DL1, KIR2DL4, KIR2DL5, KIR3DL1 and KIR3DL3 are shown in SEQ ID 48 to 57 respectively

- PDCD1 endodomain
SEQ ID No. 48
CSRAARGTIGARRTGQPLKEDPSAVPVFSVDYGELDFQWREKTPEPPVPC

VPEQTEYATI

VFPSGMGTSSPARRGSADGPRSAQPLRPEDGHCSWPL

- BTLA4
SEQ ID No. 49
KLQRRWKRTQSQQGLQENSSGQSFFVRNKKVRRAPLSEGPHSLGCYNPMM

EDGISYTTLRFPEMNIPRTGDAESSEMQRPPPDCDDTVTYSALHKRQVGD

YENVIPDFPEDEGIHYSELI

QFGVGERPQAQENVDYVILKH

- LILRB1
SEQ ID No. 50
LRHRRQGKHWTSTQRKADFQHPAGAVGPEPTDRGLQWRSSPAADAQEENL

YAAVKHTQPEDGVEMDTRSPHDEDPQAVTYAEVKHSRPRREMASPPSPLS

GEFLDTKDRQAEEDRQMDTEAAASEAPQDVTYAQLHSLTLRREATEPPPS

QEGPSPAVPSIYATLAIH

- LAIR1
SEQ ID No. 51
HRQNQIKQGPPRSKDEEQKPQQRPDLAVDVLERTADKATVNGLPEKDRET

DTSALAAGSS

QEVTYAQLDHWALTQRTARAVSPQSTKPMAESITYAAVARH

CTLA4
SEQ ID No. 52
FLLWILAAVSSGLFFYSFLLTAVSLSKMLKKRSPLTTGVYVKMPPTEPEC

EKQFQPYFIPIN

KIR2DL1
SEQ ID No. 53
GNSRHLHVLIGTSVVIIPFAILLFFLLHRWCANKKNAVVMDQEPAGNRTV

NREDSDEQDP

QEVTYTQLNHCVFTQRKITRPSQRPKTPPTDIIVYTELPNAESRSKVVSC

P

KIR2DL4
SEQ ID No. 54
GIARHLHAVIRYSVAIILFTILPFFLLHRWCSKKKENAAVMNQEPAGHRT

VNREDSDEQDPQEVTYAQLDHCIFTQRKITGPSQRSKRPSTDTSVCIELP

NAEPRALSPAHEHHSQALMGSSRETTALSQTQLASSNVPAAGI

KIR2DL5
SEQ ID No. 55
TGIRRHLHILIGTSVAIILFIILFFFLLHCCCSNKKNAAVMDQEPAGDRT

VNREDSDDQDPQEVTYAQLDHCVFTQTKITSPSQRPKTPPTDTTMYMELP

```
NAKPRSLSPAHKHHSQALRGSSRETTALSQNRVASSHVPAAGI
```

KIR3DL1
SEQ ID No. 56
```
KDPRHLHILIGTSVVIILFILLLFFLLHLWCSNKKNAAVMDQEPAGNRTA

NSEDSDEQDPEEVTYAQLDHCVFTQRKITRPSQRPKTPPTDTILYTELPN

AKPRSKVVSCP
```

KIR3DL3
SEQ ID No. 57
```
KDPGNSRHLHVLIGTSVVIIPFAILLFFLLHRWCANKKNAVVMDQEPAGN

RTVNREDSDEQDPQEVTYAQLNHCVFTQRKITRPSQRPKTPPTDTSV
```

Alternatively the inhibitory endodomain may be an ITIM containing endodomain co-expressed with a fusion protein. The fusion protein may comprise at least part of a protein-tyrosine phosphatase and at least part of a receptor-like tyrosine phosphatase. The fusion may comprise one or more SH2 domains from the protein-tyrosine phosphatase. For example, the fusion may be between a PTPN6 SH2 domain and CD45 endodomain or between a PTPN6 SH2 domain and CD148 endodomain. When phosphorylated, the ITIM domains recruit the fusion protein bring the highly potent CD45 or CD148 phosphatase to proximity to the activating endodomain blocking activation. The sequences of illustrative fusion proteins are given as SEQ ID No. 58 and 59.

- PTPN6-CD45 fusion protein
SEQ ID No. 58
```
WYHGHMSGGQAETLLQAKGEPWTFLVRESLSQPGDFVLSVLSDQPKAGPG

SPLRVTHIKVMCEGGRYTVGGLETFDSLTDLVEHFKKTGIEEASGAFVYL

RQPYKIYDLHKKRSCNLDEQQELVERDDEKQLMNVEPIHADILLETYKRK

IADEGRLFLAEFQSIPRVFSKFPIKEARKPFNQNKNRYVDILPYDYNRVE

LSEINGDAGSNYINASYIDGFKEPRKYIAAQGPRDETVDDFWRMIWEQKA

TVIVMVTRCEEGNRNKCAEYWPSMEEGTRAFGDVVVKINQHKRCPDYIIQ

KLNIVNKKEKATGREVTHIQFTSWPDHGVPEDPHLLLKLRRRVNAFSNFF

SGPIVVHCSAGVGRTGTYIGIDAMLEGLEAENKVDVYGYVVKLRRQRCLM

VQVEAQYILIHQALVEYNQFGETEVNLSELHPYLHNMKKRDPPSEPSPLE

AEFQRLPSYRSWRTQHIGNQEENKSKNRNSNVIPYDYNRVLKHELEMSKE

SEHDSDESSDDDSDSEEPSKYINASFIMSYWKPEVMIAAQGPLKETIGDF

MIQRKVKVIVMLTELKHGDQEICAQYWGEGKQTYGDIEVDLKDTDKSSTY

TLRVFELRHSKRKDSRTVYQYQYTNWSVEQLPAEPKELISMIQVVKQKLP

QKNSSEGNKHHKSTPLLIHCRDGSQQTGIFCALLNLLESAETEEVVDIFQ

VVKALRKARPGMVSTFEQYQFLYDVIASTYPAQNGQVKKNNHQEDKIEFD

NEVDKVKQDANCVNPLGAPEKLPEAKEQAEGSEPTSGTEGPEHSVNGPAS

PALNQGS
```

- PTPN6-CD148 fusion
SEQ ID No. 59
```
ETLLQAKGEPWTFLVRESLSQPGDFVLSVLSDQPKAGPGSPLRVTHIKVM

CEGGRYTVGGLETFDSLTDLVEHFKKTGIEEASGAFVYLRQPYRKKRKDA

KNNEVSFSQIKPKKSKLIRVENFEAYFKKQQADSNCGFAEEYEDLKLVGI

SQPKYAAELAENRGKNRYNNVLPYDISRVKLSVQTHSTDDYINANYMPGY

HSKKDFIATQGPLPNTLKDFWRMVWEKNVYAIIMLTKCVEQGRTKCEEYW

PSKQAQDYGDITVAMTSEIVLPEWTIRDFTVKNIQTSESHPLRQFHFTSW

PDHGVPDTTDLLINFRYLVRDYMKQSPPESPILVHCSAGVGRTGTFIAID

RLIYQIENENTVDVYGIVYDLRMHRPLMVQTEDQYVFLNQCVLDIVRSQK

DSKVDLIYQNTTAMTIYENLAPVTTFGKTNGYIA
```

The inhibitory endodomain may comprise all or part of SEQ ID No 46 or 47. It may comprise all or part of SEQ ID 48 to 57. It may comprise all or part of SEQ ID 48 to 57 co-expressed with either SEQ ID 58 or 59. It may comprise a variant of the sequence or part thereof having at least 80% sequence identity, as long as the variant retains the capacity to inhibit T cell signaling by the third CAR upon ligation of the first and second CARs.

Colocalisation-Based Inhibitory CAR System

Figure 11:
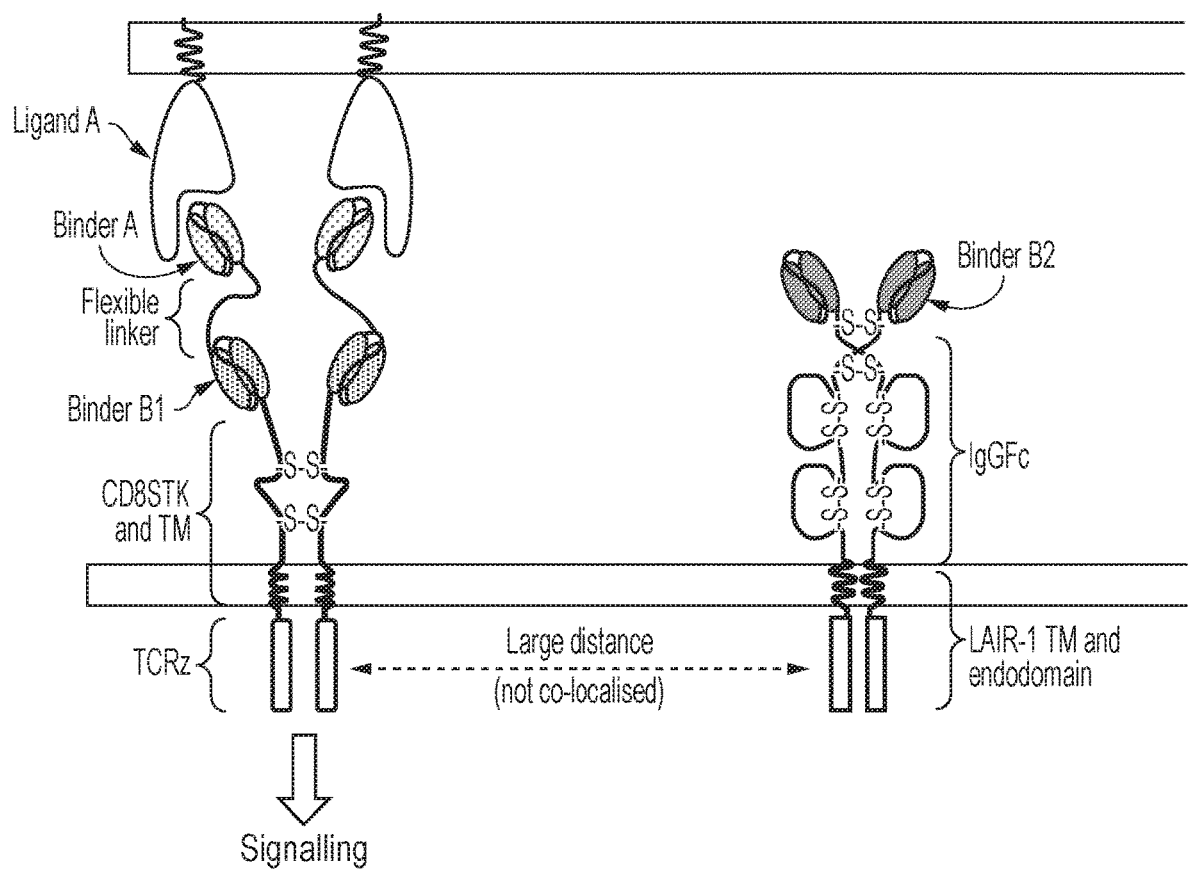
FIG. 11: A schematic diagram showing a "TanCAR" system in which the first CAR comprises two antigen binding domains, one ("Binder A") which binds a cell surface antigen ("Ligand A", e.g. PSMA) and one ("Binder B1") which binds a soluble ligand ("Ligand B", e.g. IL-6). The second CAR binds the soluble ligand ("Ligand B", e.g. IL-6) through its antigen-binding domain ("Binder B2"). The second CAR has an endodomain which inhibits T cell signalling. Binding of a cell surface antigen ("Ligand A" e.g. PSMA) by the first CAR leads to T cell signalling. However, binding of a soluble ligand (e.g. IL6) by the first and second CARs causes the inhibitory endodomain on the second CAR to colocalose with the activating endodomain on the first CAR, leading to inhibition of signalling.
Figure 11:
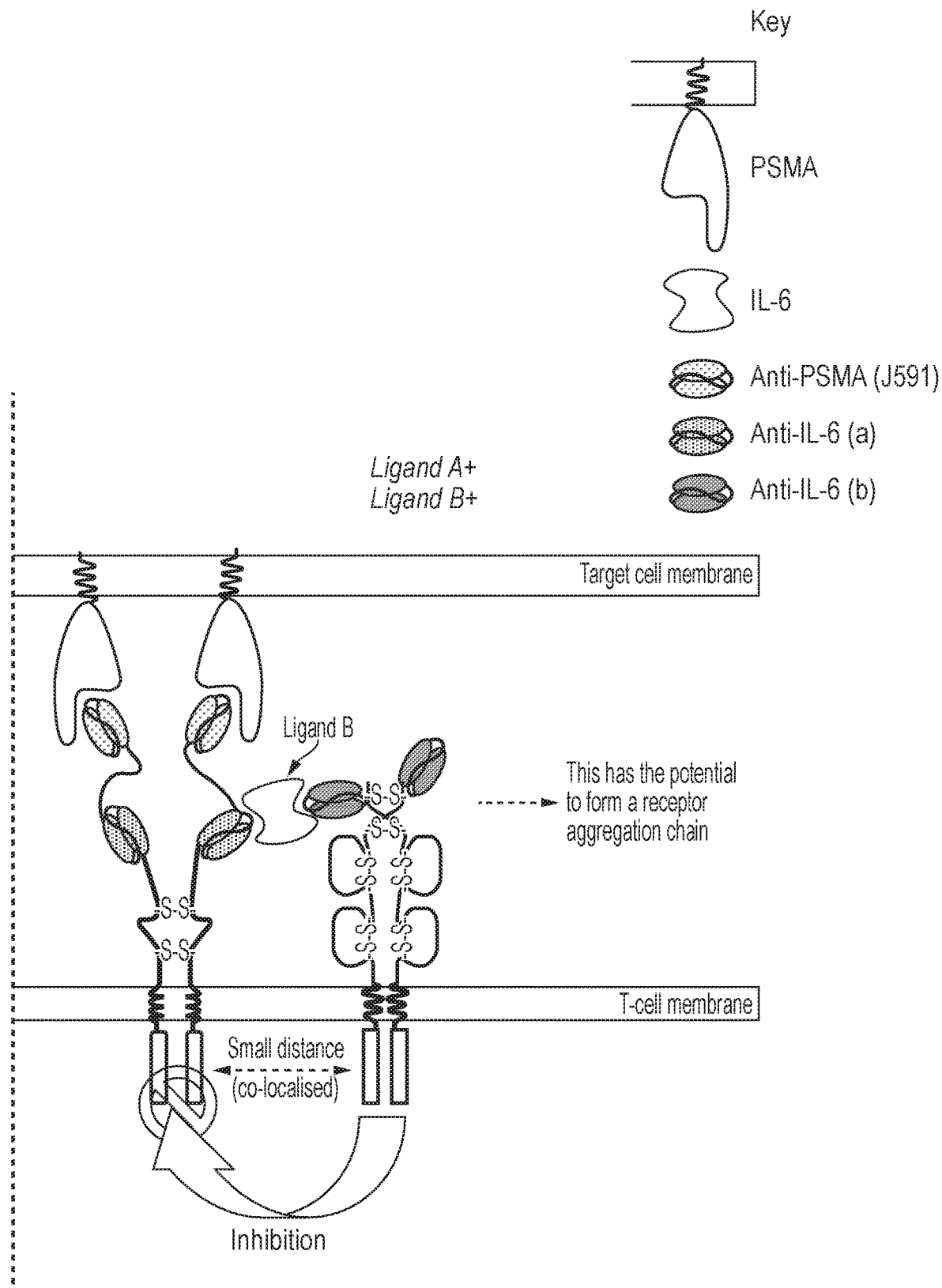

In a third embodiment of the invention the first CAR comprises two antigen binding domains: one which binds the soluble ligand; and one which binds a cell-surface antigen. This tandem arrangement of binding domains (Tan-CAR system) is illustrated schematically in FIG. 11.

When the first CAR is expressed at the surface of a cell, such as a T-cell, the antigen binding-domain which binds the cell-surface antigen may be distal to the cell membrane and the antigen binding-domain which binds the soluble ligand may be proximal to the cell membrane In this system, the second CAR may comprise an inhibitory endodomain, such that when the first and second CARs bind the soluble ligand, cell activation caused by the first CAR binding the cell surface antigen is inhibited.

The inhibitory endodomain is a "ligation-on" inhibitory endodomain, such that the second CAR does not significantly inhibit T-cell activation by the first CAR in the absence of soluble ligand, but inhibits T-cell activation by the first CAR when the first and second CAR bind the soluble ligand.

The inhibitory endodomain may be or comprise a phosphatase with slow kinetics, such as one comprising of the catalytic domain of PTPN6 or an ITIM as defined in the previous section.

In this embodiment of the invention, the first and second CAR may bind IL-6.

Aggregation-Based and Gate

Figure 12:
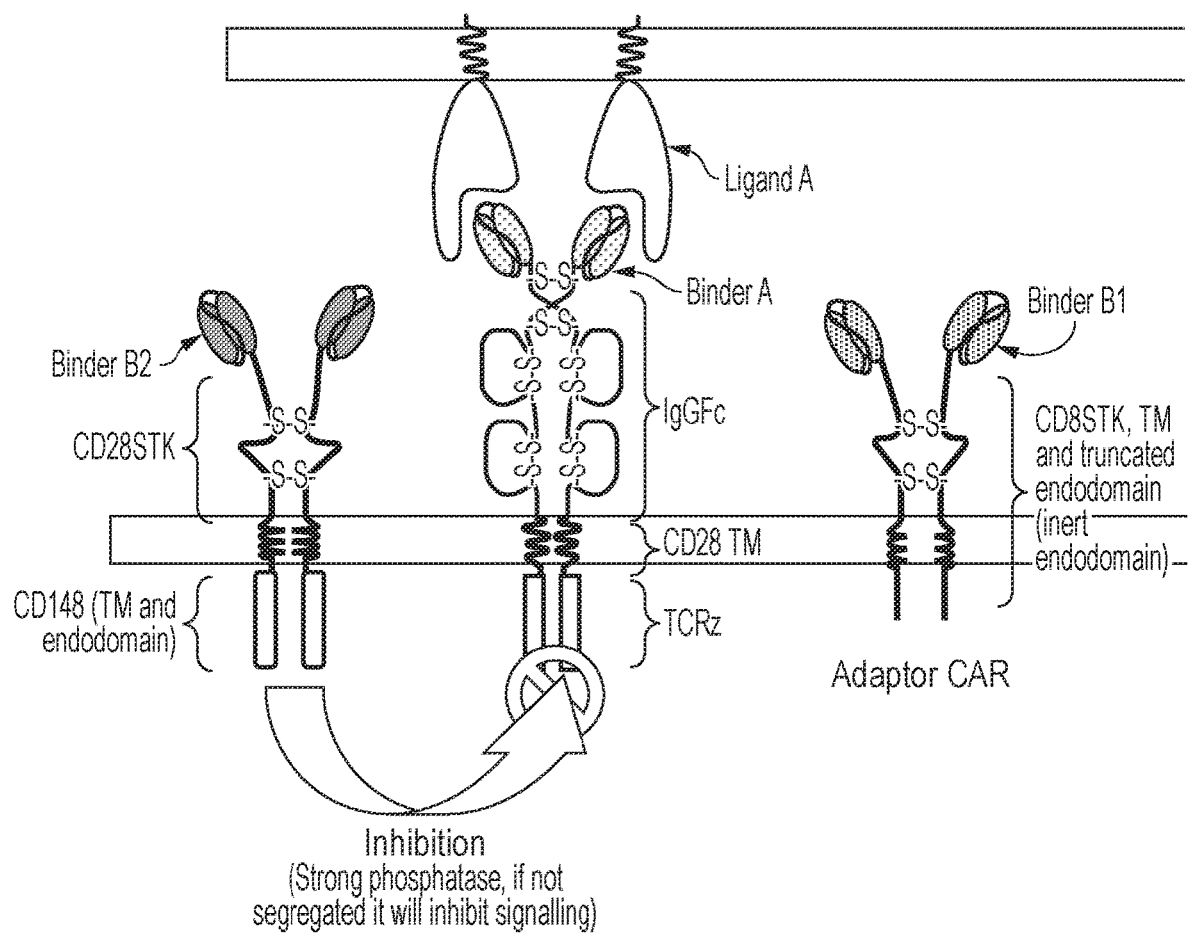
FIG. 12: A schematic diagram showing an "AND gate" system, in which the first and/or second CAR comprises an inhibitory endodomain with fast kinetics (eg CD148 endodomain. In the absence of the soluble ligand, the inhibitory endodomain constitutively inhibits the activating endodomain on the third CAR. In the presence of soluble ligand, the first and second CARs aggregate and segregate from the third CAR, allowing T-cell signalling to occur.
Figure 12:
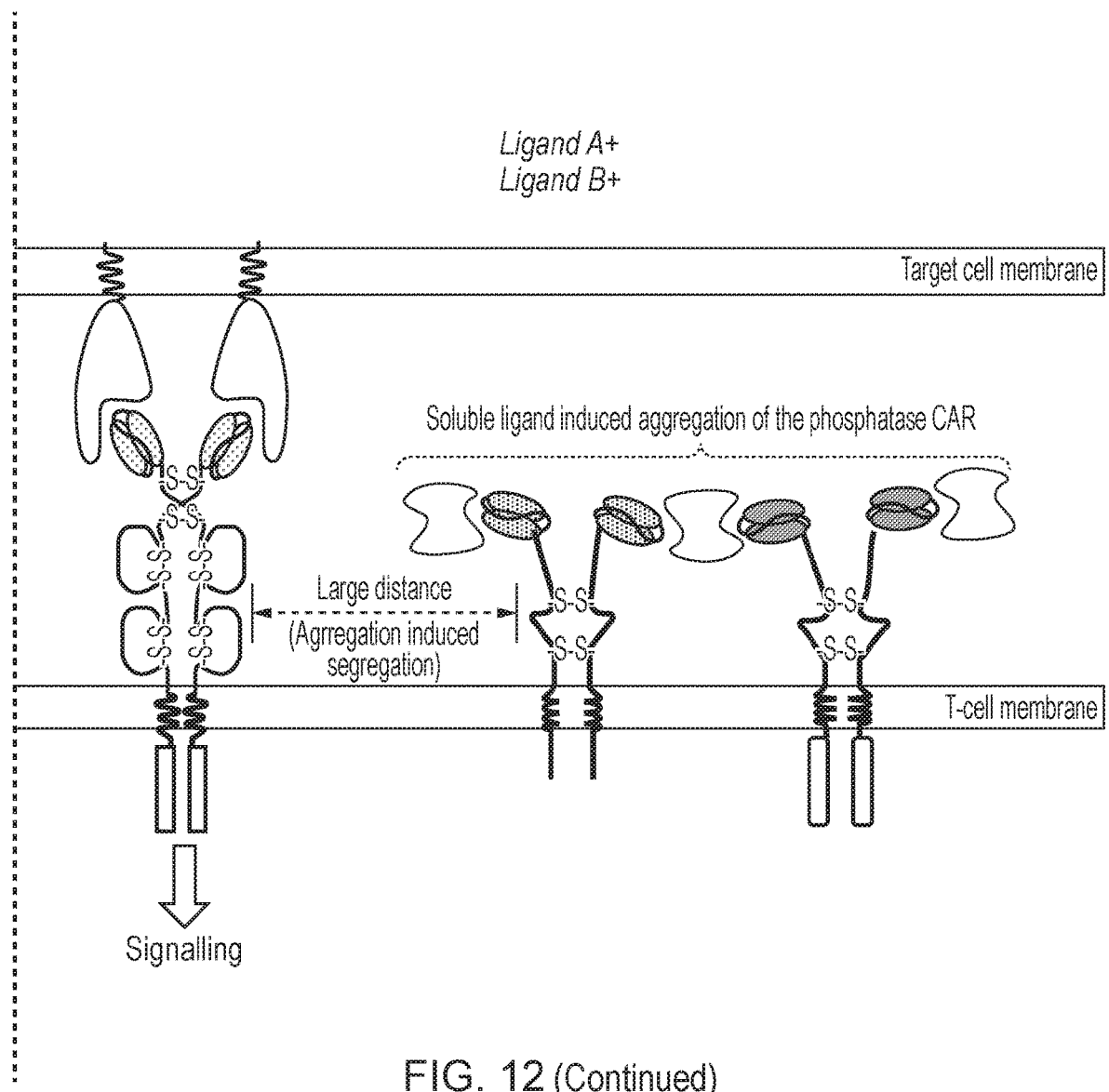
Figure 13:
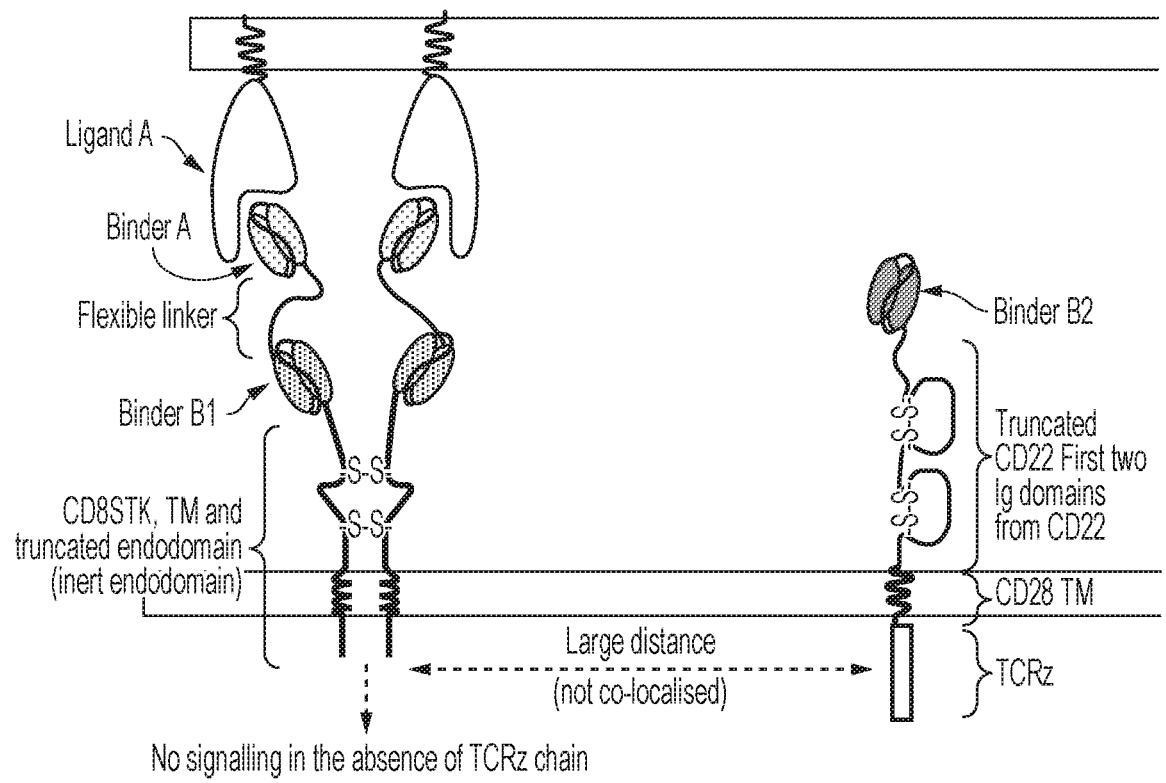
FIG. 13: A schematic diagram showing and alternative "AND gate" system, in which the first CAR comprises two antigen binding domains, one ("Binder A") which binds a cell surface antigen ("Ligand A", e.g. PSMA) and one ("Binder B1") which binds a soluble ligand ("Ligand B", e.g. PSA). The second CAR binds the soluble ligand ("Ligand B", e.g. PSA) through its antigen-binding domain ("Binder B2"). The first CAR does not comprise a functional T-cell activating endodomain, whereas the second CAR does comprise a functional T-cell activating endodomain. In the absence of the soluble ligand, binding of the cell surface antigen does not lead to cell signalling due to the absence of a TCR zeta chain. In the presence of the soluble ligand, the first and second CARs co-localise and binding of the cell surface antigen by the first CAR does lead to cell signalling. In order to prevent signalling in the absence of the cell-surface ligand, the second CAR may be monomeric, which may be achieved using a monomeric spacer such as one based on CD22.
Figure 13:
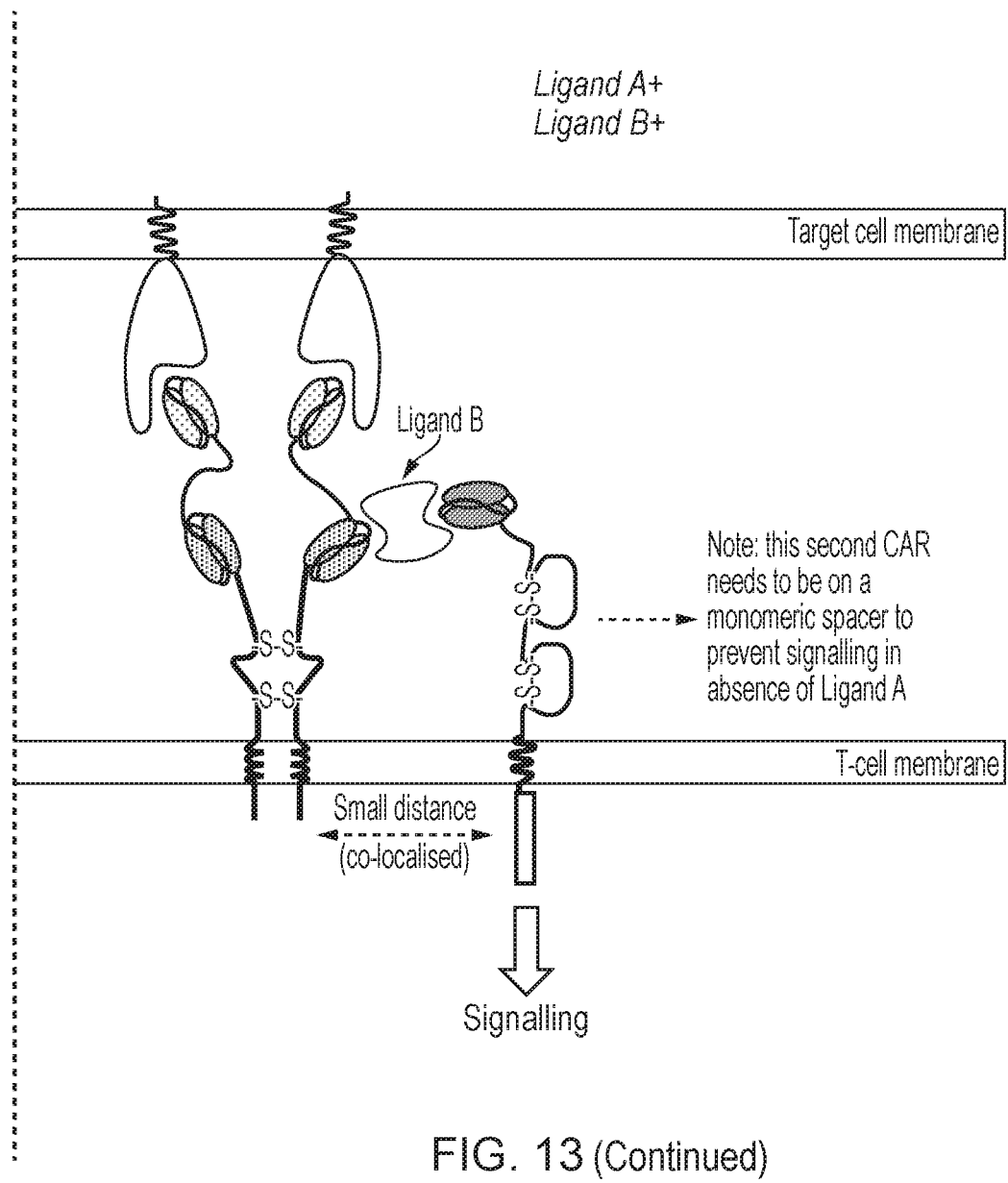

In a fourth embodiment of the invention, the third CAR, which binds a cell-surface antigen, comprises an activating endodomain, and the first and/or second CAR(s) comprise(s) a "ligation-off" inhibitory endodomain (see FIG. 12).

This embodiment is based on the kinetic segregation model (KS) of T-cell activation. This is a functional model, backed by experimental data, which explains how antigen recognition by a T-cell receptor is converted into downstream activation signals. Briefly: at the ground state, the signalling components on the T-cell membrane are in dynamic homeostasis whereby dephosphorylated ITAMs are favoured over phosphorylated ITAMs. This is due to greater activity of the transmembrane CD45/CD148 phosphatases over membrane-tethered kinases such as lck. When a T-cell engages a target cell through a T-cell receptor (or CAR) recognition of cognate antigen, tight immunological synapses form. This close juxtapositioning of the T-cell and target membranes excludes CD45/CD148 due to their large ectodomains which cannot fit into the synapse. Segregation of a high concentration of T-cell receptor associated ITAMs and kinases in the synapse, in the absence of phosphatases, leads to a state whereby phosphorylated ITAMs are favoured. ZAP70 recognizes a threshold of phosphorylated ITAMs and propagates a T-cell activation signal. This advanced understanding of T-cell activation is exploited by the present invention. In particular, the invention is based on this understanding of how ectodomains of different length and/or bulk and/or charge and/or configuration and/or glycosylation result in differential segregation upon synapse formation.

In the aggregation-based AND gate of the invention embodiment, the third CAR which binds the cell-surface antigen comprises an activating endodomain and the first and/or second CAR(s) which bind the soluble ligand comprise an inhibitory endodomain. The inhibitory CAR constitutively inhibits the third CAR, but upon binding the soluble ligand releases its inhibition of the activating CAR. In this manner, a T-cell can be engineered to trigger only in the presence of the cell-surface antigen (Ligand A in FIG. 12) and the soluble antigen (Ligand B in FIG. 12). This behaviour is achieved by the third CAR comprising an activating endodomain containing ITAM domains for example the endodomain of CD3 Zeta, and the inhibitory CAR comprising the endodomain from a phosphatase able to dephosphorylate an ITAM (e.g. CD45 or CD148). When only the third CAR is ligated, the first and/or second CAR with the inhibitory endodomain is in solution on the T-cell surface and can diffuse in and out of the synapse inhibiting the activating CAR. When the first and second CAR bind the soluble ligand, they aggregate causing segregation from the third CAR allowing the third CAR to trigger T-cell activation.

Colocalisation-Based and Gate

In a fifth embodiment of the invention, the first CAR comprises two antigen binding domains: one which binds the soluble ligand; and one which binds a cell-surface antigen. This tandem arrangement of binding domains (TanCAR system) is similar to the third embodiment of the invention described above.

In this co-localisation-based AND gate, the first CAR lacks a functional endodomain. It may comprise an inert or truncated endodomain. The endodomain may lack any or a sufficient number of ITAMs to transmit an activation signal to the T cell after antigen is bound.

The second CAR comprises a functional endodomain which comprises one or more ITAMs capable of triggering T-cell signalling. Binding of the soluble ligand causes co-localisation of the first and second CARs and enables T-cell signalling to occur when the first CAR binds the cell surface antigen. The second CAR may, for example, comprise the CD3 zeta endodomain.

The second CAR may be monomeric to avoid signalling in the absence of Ligand A. This may be achieved by the second CAR comprising a monomeric spacer.

A truncated version of CD22 which comprises one or more Ig domains, may be used as a monomeric spacer.

Vector

The present invention also provides a vector, or kit of vectors, which comprises one or more nucleic acid sequence(s) encoding a first and a second CAR according to the first aspect of the invention. Such a vector may be used to introduce the nucleic acid sequence(s) into a host cell so that it expresses a first and a second CAR according to the first aspect of the invention.

The vector may, for example, be a plasmid or a viral vector, such as a retroviral vector or a lentiviral vector, or a transposon based vector or synthetic mRNA.

The vector may be capable of transfecting or transducing a T cell or a NK cell.

Cell

The present invention provides a cell which comprises a first chimeric antigen receptor (CAR) and a second CAR, the first and second CARs binding different epitopes on the same ligand.

The cell may comprise a nucleic acid or a vector of the present invention.

The cell may be a cytolytic immune cell such as a T cell or an NK cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+ FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR cells of the invention may be any of the cell types mentioned above.

T or NK cells according to the first aspect of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells according to the first aspect of the invention may be derived from ex vivo differentiation of inducible progenitor cells or embryonic progenitor cells to T or NK cells. Alternatively, an immortalized T-cell line which retains its lytic function and could act as a therapeutic may be used.

In all these embodiments, CAR cells are generated by introducing DNA or RNA coding for first and second CARs by one of many means including transduction with a viral vector, transfection with DNA or RNA.

The CAR cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding the molecules providing the CAR according to the first aspect of the invention or a component(s) of the CAR signalling system according to the second aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with one or more a nucleic acid sequence(s) encoding first and second CARs.

The T or NK cells may then by purified, for example, selected on the basis of expression of the antigen-binding domain of the antigen-binding polypeptide.

Pharmaceutical Composition

The present invention also relates to a pharmaceutical composition containing a plurality of cells according to the first aspect of the invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering the cells of the present invention (for example in a pharmaceutical composition as described above) to a subject.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a T or NK cell-containing sample;
(ii) transducing or transfecting such cells with a nucleic acid sequence or vector provided by the present invention;
(iii) administering the cells from (ii) to a subject.

The T or NK cell-containing sample may be isolated from a subject or from other sources, for example as described above. The T or NK cells may be isolated from a subject's own peripheral blood (1st party), or in the setting of a haematopoietic stem cell transplant from donor peripheral blood (2nd party), or peripheral blood from an unconnected donor (3rd party).

The present invention provides a CAR cell of the present invention for use in treating and/or preventing a disease.

The invention also relates to the use of a CAR cell of the present invention in the manufacture of a medicament for the treatment and/or prevention of a disease.

The disease to be treated and/or prevented by the methods of the present invention may be a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

Where the soluble ligand is PSA, the cancer may be prostate cancer.

The CAR cells of the present invention may be capable of killing target cells, such as cancer cells. The target cell may be characterised by the presence of a soluble ligand in the vicinity of the target cell. The target cell may be characterised by the presence of a soluble ligand together with the expression of a tumour-associated antigen (TAA) at the target cell surface.

The CAR cells of the present invention may be capable of killing target cells, such as cancer cells, which express a low density of the TAA. Examples of TAAs which are known to be expressed at low densities in certain cancers include, but are not limited to, ROR1 in CLL, Typr-1 in melanoma and BCMA in myeloma.

The CAR cells and pharmaceutical compositions of present invention may be for use in the treatment and/or prevention of the diseases described above.

The CAR cells and pharmaceutical compositions of present invention may be for use in any of the methods described above.

The invention will now be further described by way of Examples, which are meant to serve to assist one of ordinary skill in the art in carrying out the invention and are not intended in any way to limit the scope of the invention.

EXAMPLES

Example 1—Triggering T-Cell Activation with a Soluble Ligand

Normally a CAR will not be activated with monomeric soluble ligand because the ligand just binds to the receptor without causing segregation of the engaged receptor (FIG.

Figure 2:
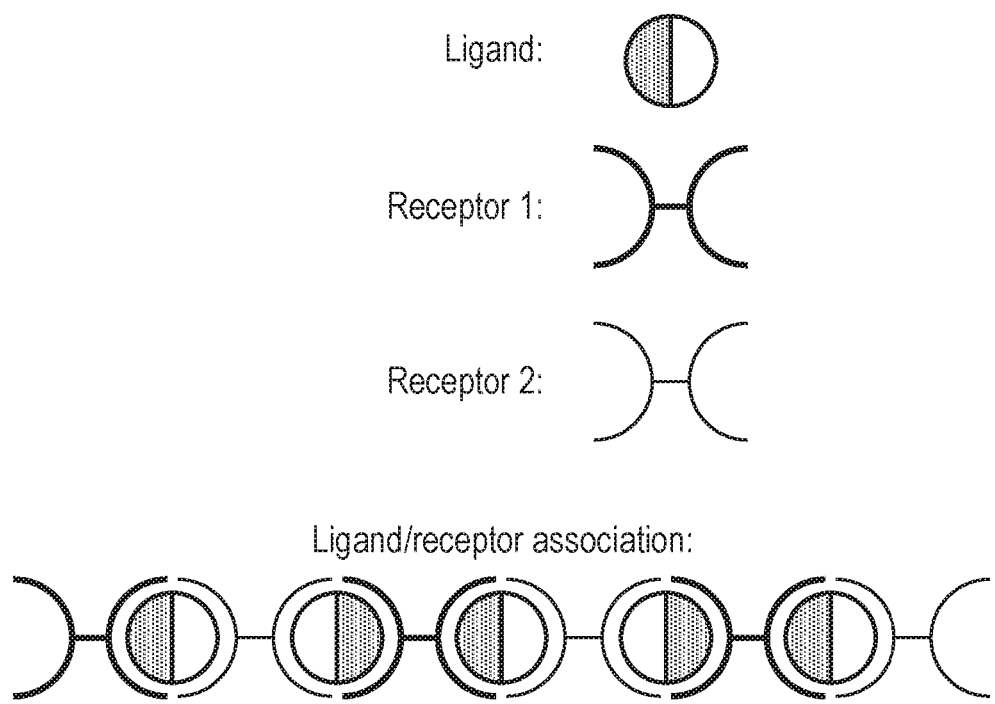
FIG. 2: A schematic diagram illustrating the predicted aggregation with soluble ligand with a dual CAR platform where both CARs recognise the same ligand.
Figure 3:
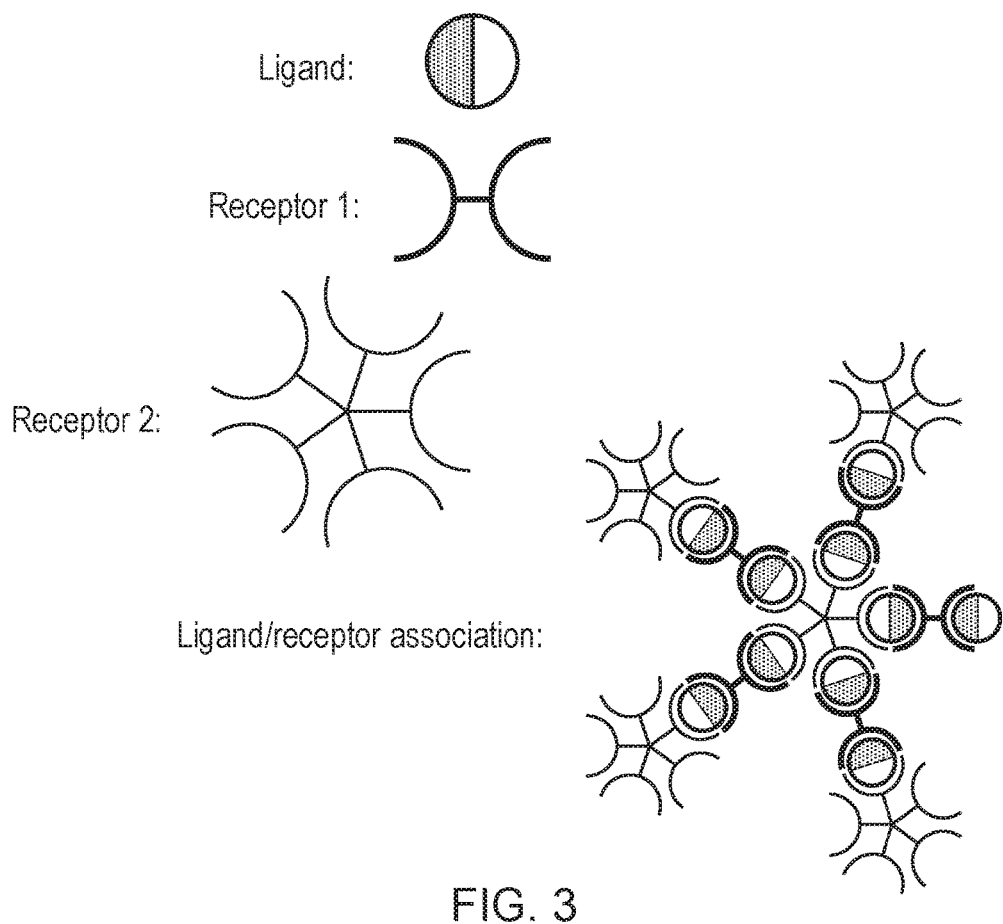
FIG. 3: A schematic diagram illustrating the predicted aggregation with soluble ligand with a dual CAR platform where both CARs recognise the same ligand and where one CAR is multivalent.

1). In order to aggregate receptors to a soluble ligand it is necessary to have at least two CARs that bind to two non-competitive epitopes (FIG. 2). CARs are typically homodimers, but trimeric or multivalent receptors may show improved performance (FIG. 3).

Figure 4:
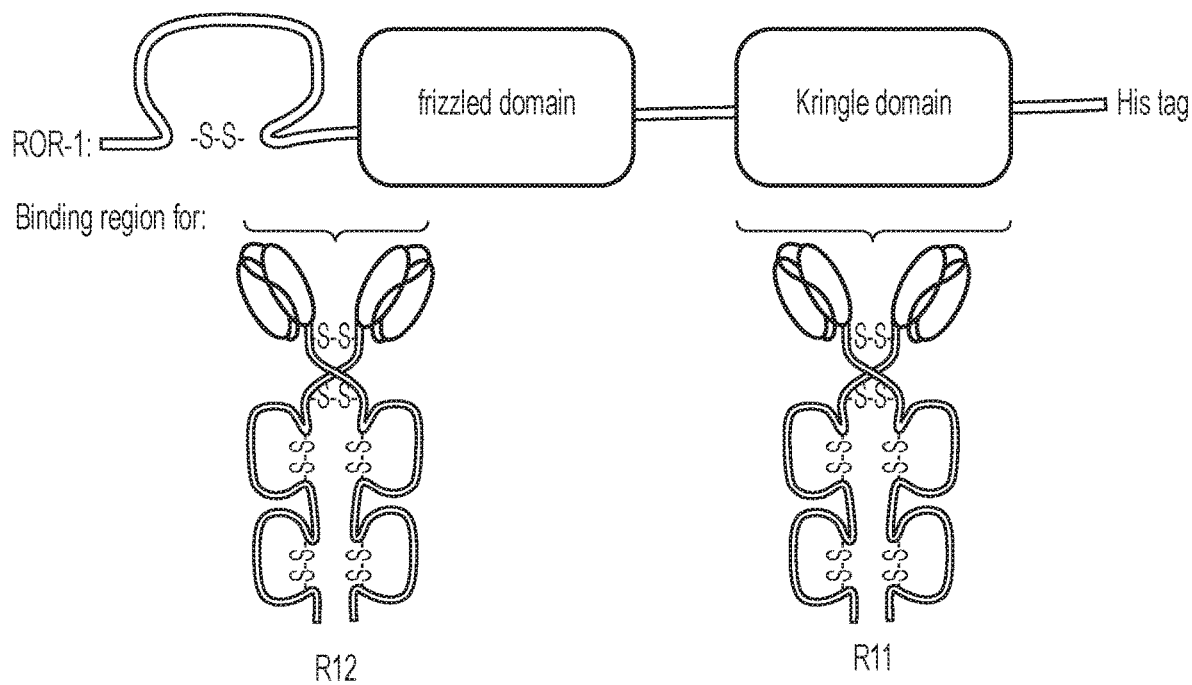
FIG. 4: A schematic diagram illustrating the model used to show proof-of-concept. The ligand used was ROR-1 and the first and second receptors were R12 and R11 respectively.
Figure 5:
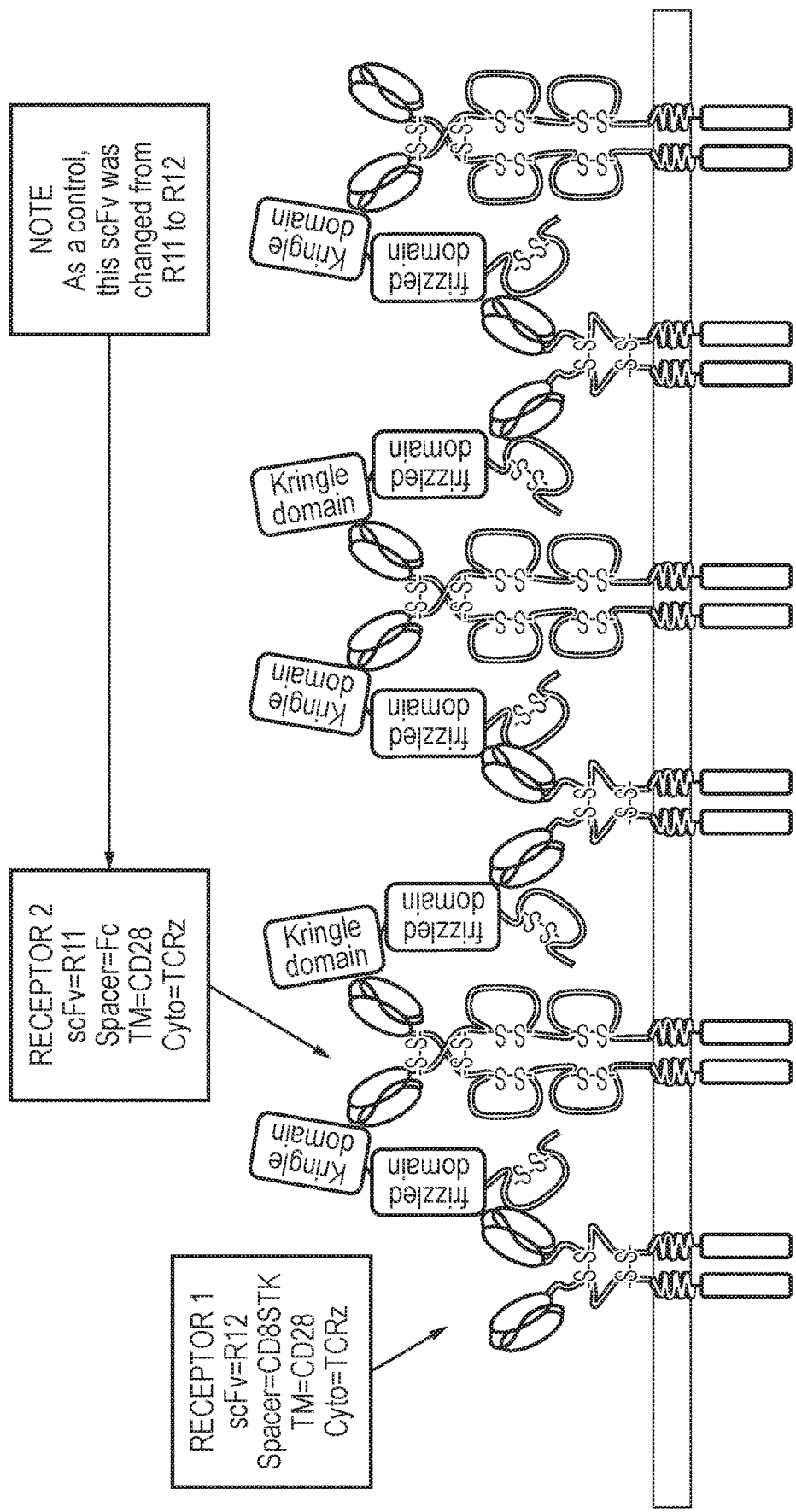
FIG. 5: A schematic diagram illustrating the predicted aggregation with ROR-1 using the model system tested in the Examples.

As a proof-of-concept, soluble monomeric ROR-1 was used as the ligand (FIG. 4). Two CARs were used which bind to mutually exclusive epitopes on the ROR-1 ligand named R12 and R11. Following the aggregation model, it was predicted that T-cell expressing either R11 or R12 will not activate with soluble ligand, but T-cell expressing both R12 and R11 will activate in the presence of soluble ligand. In order to stop the R12 and R11 CAR from cross binding to each other (causing a heterodimer) the R12 was placed on a CD8STK spacer and the R11 on an Fc spacer (FIG. 5). As a control a dual CAR expressing T-cell was used where both CARs contain the R12 scFv (one on a CD8STK and the other on an Fc spacer). In order to investigate the effect of having one of the CARs as a multivalent CAR, in one system the R12 CAR was placed on a CD8STK spacer and the R11 on a COMP spacer (FIG. 6).

Figure 7:
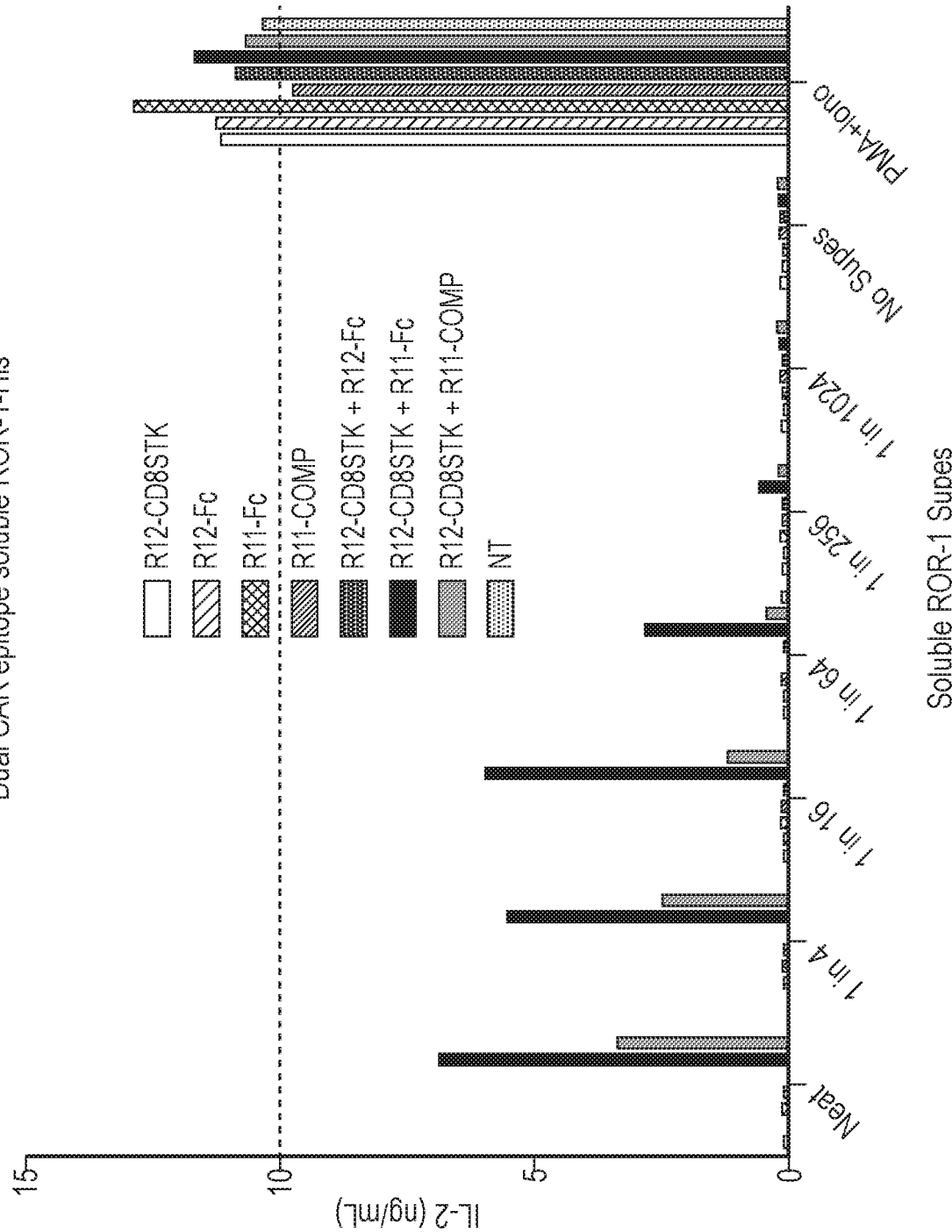
FIG. 7: A graph showing IL-2 secretion in the presence of soluble ligand (ROR-1). BW5 T-cells were transduced with either a single CAR (R11 or R12 with either an Fc or CD8STK or COMP spacer) or with two CARs. These T-cells were co-cultured with soluble ROR-1 ligand and IL-2 was detected after 24 h.

A mouse T-cell line (BW5 cells) was transduced with either a single CAR that contained an R12 scFv on a CD8STK or Fc spacer or a single CAR that contained an R11 scFv on a Fc or COMP spacer. In addition BW5 cells that were positive for R12-CD8STK were transduced to express a second CAR that was either R11-Fc, R11-COMP or, as a control, R12-Fc. All CARs used in this experiment had an intracellular TCRz domain (1st generation). These cells were stimulated with supernatant containing soluble ROR-1 (His tagged) and the IL-2 was measured after 24 h (FIG. 7).

In was found that only T-cells that expressed both the R11 and R12 CAR were able to stimulate in the presence of soluble ligand. Importantly the T-cell expressing two copies of R12 was not able to stimulate with soluble ligand.

Figure 8:
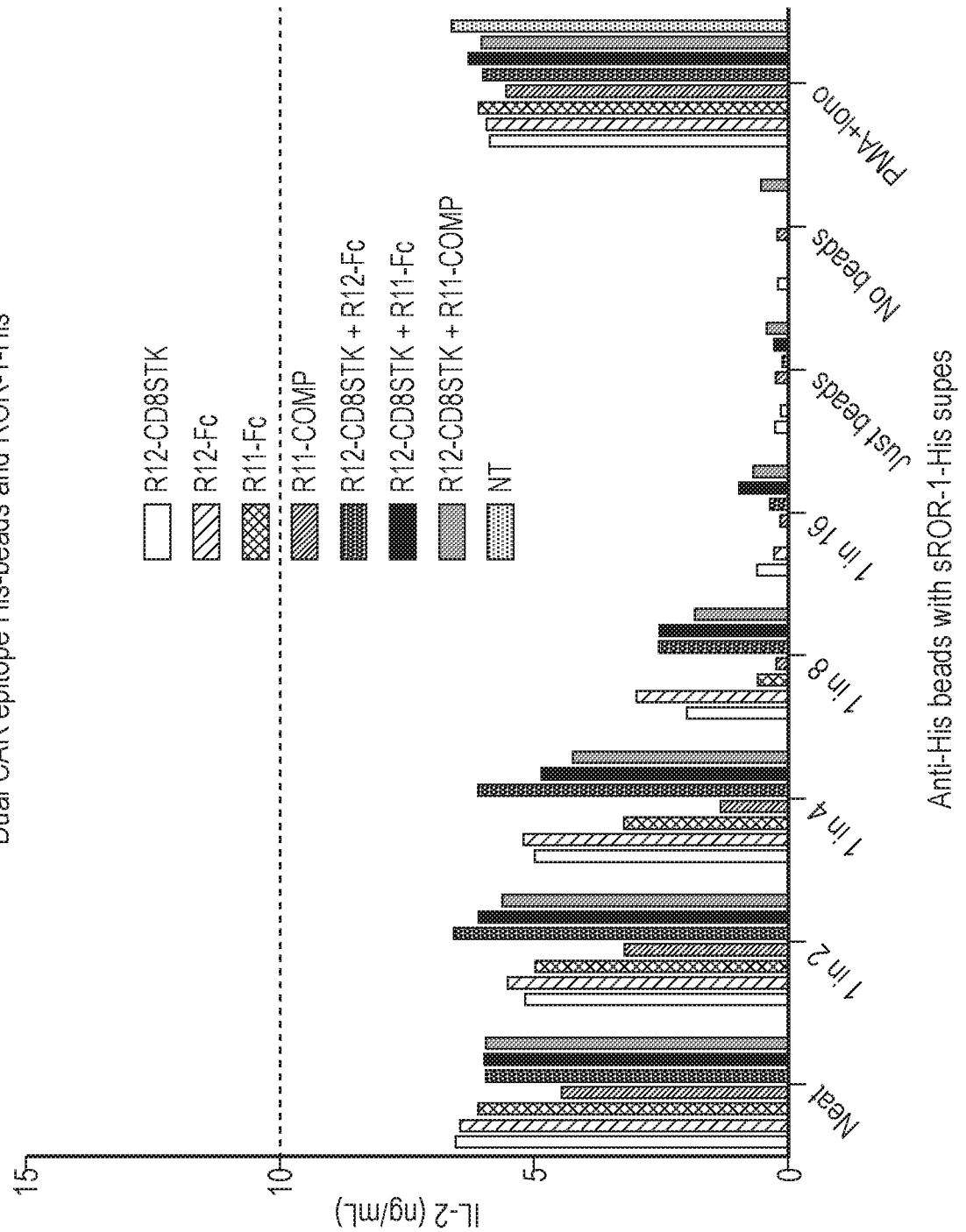
FIG. 8: A graph showing IL-2 secretion in the presence of an immobilized ligand. BW5 T-cells were transduced with either a single CAR (R11 or R12 with either an Fc or CD8STK or COMP spacer) or with two CARs. These T-cells were co-cultured with anti-His beads that were pre-coated with soluble His tagged ROR-1 ligand and IL-2 was detected after 24 h.

As a further control to test that these T-cells were able to be stimulated with immobilised ligand, these T-cells were stimulated with anti-His beads that were pre-coated with different concentrations of the soluble ROR-1 his tag (FIG. 8). This figure shows that all T-cells were able to be stimulated with immobilised ligand, indicating that all the T-cells used in this experiment were capable of transmitting a signal however only a dual CAR to two mutually exclusive epitopes was able to be stimulated with soluble ligand.

Example 2—The Use of Aggregation-Based AND Gate to Trigger T-Cell Activation in the Presence of Both a Membrane-Bound Ligand and a Soluble Ligand In order to demonstrate the feasibility of a "Split" CAR system BW5 cells were transduced with a vector expressing either:
  i) aCD19-CD8STK-TCRz-2A-R12-IgGFc-CD148 or
  ii) aCD19-CD8STK-TCRz-2A-R12-IgGFc-CD148 and R11-IgMFc-CD148 and exposed to either non-transfected SupT1 target cells or SupT1 target cells expressing CD19. A co-culture was carried out with a 4:1 target to effector ratio with different concentrations of soluble ROR-1 supernatants.

Figure 14:
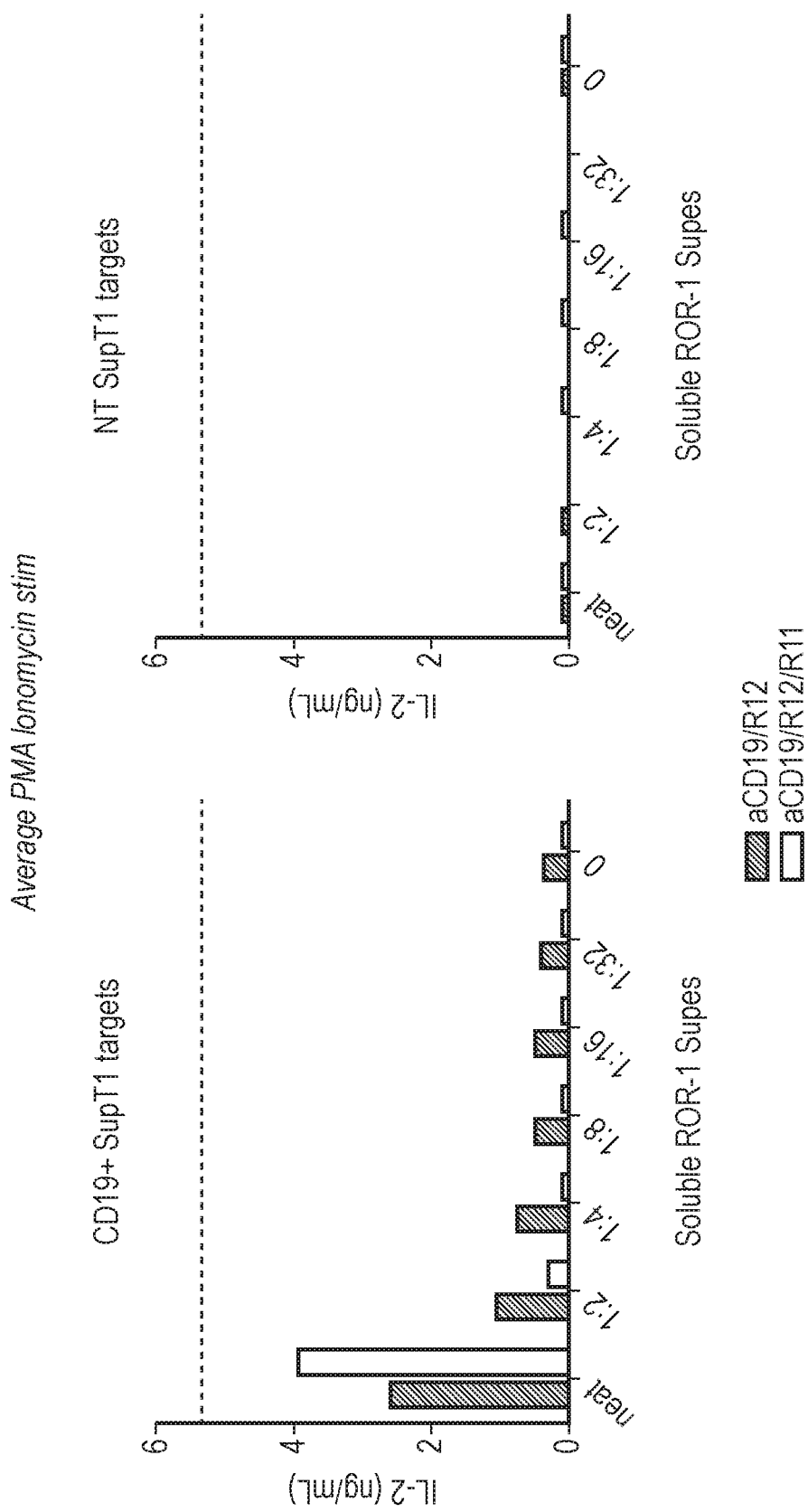
FIG. 14: An aggregation-based AND gate only signals in the presence of membrane-bound antigen (CD19) and soluble ligand (ROR1).

The results are shown in FIG. 14. T cell activation is maximal in the presence of both the membrane-bound antigen (CD19) and the soluble ligand (ROR1). Targets which did not express the membrane-bound antigen (NT) did not give T-cell stimulation.

Example 3—Induced Aggregation with Subsequent T Cell Activation Occurs with the Soluble Ligand PSA, Using a Two-CAR System Based on the PSA-Binding mAbs (5D5A5 and 5D5D11)

Figure 15:
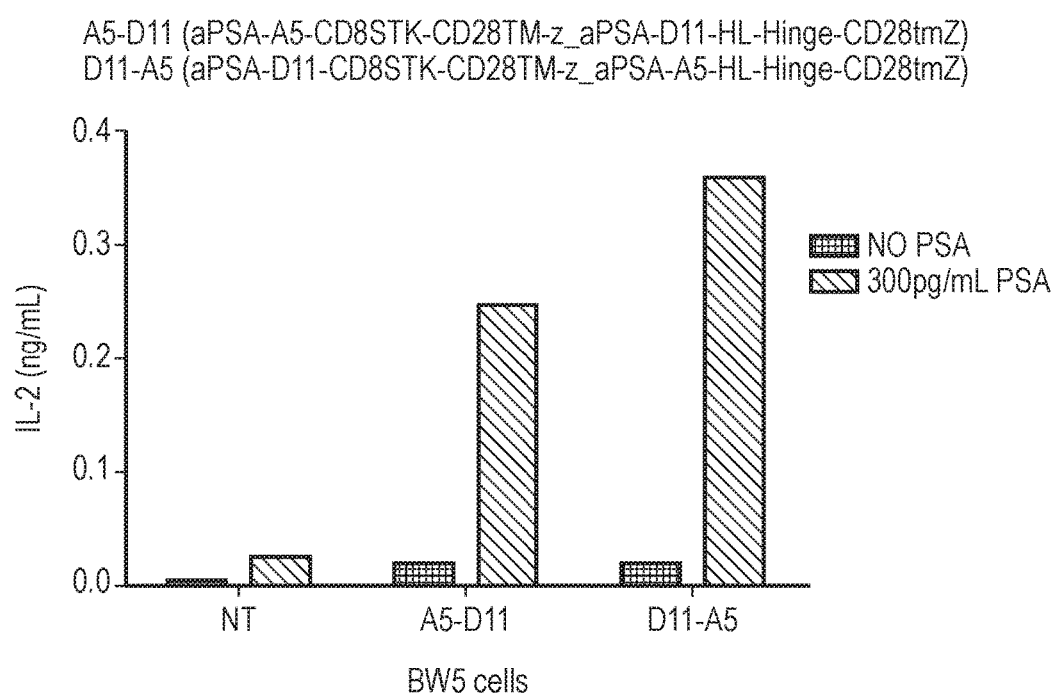
FIG. 15: A graph to show IL-2 secretion in the presence of the soluble ligand PSA. BW5 T-cells were transduced with a vector expressing two CARs, which bind different epitopes of PSA. One CAR had an antigen binding domain based on 5A5A5 and one CAR having an antigen binding domain based on 5D3D11 (aPSA-A5-CD8STK-CD28TM-z_aPSA-D11-HL-Hinge-CD28tmZ or aPSA-D11-CD8STK-CD28TM-z_aPSA-A5-HL-Hinge-CD28tmZ). These T-cells were co-cultured with soluble PSA ligand and IL-2 was detected after 24 h.

BW5 T-cells were transduced with a vector expressing;
  i) A5-D11 (aPSA-A5-CD8STK-CD28TM-z_aPSA-D11-HL-Hinge-CD28tmZ), or
  ii) D11-A5 (aPSA-D11-CD8STK-CD28TM-z_aPSA-A5-HL-Hinge-CD28tmZ)

and then incubated in the presence of 300 pg/mL PSA, to determine whether the PSA antigen binding domains in the construct of the two CAR system induces aggregation with subsequent CAR activation. The graph (FIG. 15) shows that both A5-D11 and D11-A5 constructs resulted in the BW5 T-cells secreting significant levels of IL-2, indicating T-cell activation.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A cell which comprises a first chimeric antigen receptor (CAR) and a second CAR, wherein the first and second CARs bind different epitopes on the same ligand, wherein the ligand is a cytokine, a chemokine, a tumor-associated antigen, or a soluble ligand secreted by tumor cells.

2. A cell according to claim 1, wherein the ligand is a soluble ligand.

3. A cell according to claim 2, wherein the ligand is a cytokine, chemokine or metabolite.

4. A cell according to claim 1 which comprises a third CAR which binds a cell surface antigen.

5. A cell according to claim 4, wherein the first and/or second and third CARs each comprise:
   (i) an antigen-binding domain;
   (ii) a trans-membrane domain; and
   (iii) an endodomain
   wherein the endodomains of the third CAR and the first and/or second CAR(s) are complementary, such that cell activation occurs when the ligand is bound by the first and second CARs and the cell surface antigen is bound by the third CAR.

6. A cell according to claim 5, wherein the third CAR comprises a CD3 zeta endodomain, and the first and/or second CAR(s) comprise a CD28 endodomain and a OX40 or 41BB endodomain.

7. A cell according to claim 4 wherein the third CAR binds prostate-specific membrane antigen (PSMA) and the first and second CARs bind prostate-specific antigen (PSA).

8. A nucleic acid construct which comprises a first nucleic acid sequence encoding a first CAR; and a second nucleic acid sequence encoding a second CAR, wherein the first and second CARs bind different epitopes on the same ligand, wherein the ligand is a cytokine, a chemokine, a tumor-associated antigen, or a soluble ligand secreted by tumor cells.

9. A nucleic acid construct according to claim 8, which has the following structure:

AgB1-spacer1-TM1-endo1-coexpr-AbB2-spacer2-TM2-endo2 in which
   AgB1 is a nucleic acid sequence encoding the antigen-binding domain of the first CAR;
   spacer 1 is a nucleic acid sequence encoding the spacer of the first CAR;
   TM1 is a nucleic acid sequence encoding the transmembrane domain of the first CAR;
   endo 1 is a nucleic acid sequence encoding the endodomain of the first CAR;
   coexpr is a nucleic acid sequence encoding a cleavage site enabling co-expression of both CARs;
   AgB2 is a nucleic acid sequence encoding the antigen-binding domain of the second CAR;
   spacer 2 is a nucleic acid sequence encoding the spacer of the second CAR;
   TM2 is a nucleic acid sequence encoding the transmembrane domain of the second CAR;
   endo 2 is a nucleic acid sequence encoding the endodomain of the second CAR;
   which nucleic acid construct, when expressed in a T cell, encodes a polypeptide which is cleaved at the cleavage site such that the first and second CARs are co-expressed at the T cell surface.

10. A nucleic acid construct according to claim 8, which also comprises a nucleic acid sequence encoding a third CAR which binds a cell surface antigen.

11. A vector comprising a nucleic acid construct according to claim 8.

12. A retroviral vector or a lentiviral vector or a transposon according to claim 11.

13. A kit which comprises:
   i) a vector comprising a nucleic acid sequence encoding a first; and
   ii) a vector comprising a nucleic acid sequence encoding a second CAR, wherein the first and seconded CARs bind different epitopes on the same ligand, wherein the ligand is a cytokine, a chemokine, a tumor-associated antigen, or a soluble ligand secreted by tumor cells.

14. A kit according to claim 13 which also comprises a vector comprising a nucleic acid sequence encoding a third CAR which binds a cell surface antigen.

15. A method for making a cell, which comprises the step of introducing: a nucleic acid construct according to claim 8, into a cell.

16. A method according to claim 15, wherein the cell is from a sample isolated from a subject.

17. A pharmaceutical composition comprising a plurality of cells according to claim 1.

18. A method for treating cancer, which comprises the step of administering a pharmaceutical composition according to claim 17 to a subject.

19. A method according to claim 18, which comprises the following steps:
   (i) isolation of a cell-containing sample from a subject;
   (ii) transduction or transfection of the cells with: a nucleic acid construct according to any of claim 8; and
   (iii) administering the cells from (ii) to a the subject.

* * * * *

UNITED STATES PATENT AND TRADEMARK OFFICE
CERTIFICATE OF CORRECTION

PATENT NO. : 11,365,262 B2  
APPLICATION NO. : 15/753505  
DATED : June 21, 2022  
INVENTOR(S) : Martin Pulé et al.

Page 1 of 1

It is certified that error appears in the above-identified patent and that said Letters Patent is hereby corrected as shown below:

In the Claims

At Column 81, Line 28, "endodomain" should be -- endodomain, --.

At Column 82, Line 37, "seconded" should be -- second --.

At Column 82, Line 58, "to any of" should be -- to --.

At Column 82, Line 59, "a the" should be -- a --.

Signed and Sealed this  
Twenty-seventh Day of December, 2022

Katherine Kelly Vidal  
*Director of the United States Patent and Trademark Office*

SEQUENCE LISTING

<160> NUMBER OF SEQ ID NOS: 64

<210> SEQ ID NO 1
<211> LENGTH: 118
<212> TYPE: PRT
<213> ORGANISM: Artificial Sequence
<220> FEATURE:
<223> OTHER INFORMATION: sequence of 5D3D11 VH

<400> SEQUENCE: 1

Gln Val Gln Leu Gln Gln Ser Gly Pro Glu Leu Val Lys Pro Gly Ala
1               5                   10                  15

Ser Val Lys Ile Ser Cys Lys Val Ser Gly Tyr Ala Ile Ser Ser Ser
            20                  25                  30

Trp Met Asn Trp Val Lys Gln Arg Pro Gly Gln Gly Leu Glu Trp Ile
            35                  40                  45

Gly Arg Ile Tyr Pro Gly Asp Gly Asp Thr Lys Tyr Asn Gly Lys Phe
 50                  55                  60

Lys Asp Lys Ala Thr Leu Thr Val Asp Lys Ser Ser Thr Ala Tyr
65                  70                  75                  80

Met Gln Leu Ser Ser Leu Thr Ser Val Asp Ser Ala Val Tyr Phe Cys
            85                  90                  95

Ala Arg Asp Gly Tyr Arg Tyr Tyr Phe Asp Tyr Trp Gly Gln Gly Thr
                100                 105                 110

Ser Val Thr Val Ser Ser
            115

<210> SEQ ID NO 2
<211> LENGTH: 112
<212> TYPE: PRT
<213> ORGANISM: Artificial Sequence
<220> FEATURE:
<223> OTHER INFORMATION: sequence of 5D3D11 VL

<400> SEQUENCE: 2

Asp Ile Val Met Thr Gln Thr Ala Pro Ser Val Phe Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
 50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Met Gln His
            85                  90                  95

Leu Glu Tyr Pro Val Thr Phe Gly Ala Gly Thr Lys Val Glu Ile Lys
                100                 105                 110

<210> SEQ ID NO 3
<211> LENGTH: 117
<212> TYPE: PRT
<213> ORGANISM: Artificial Sequence
<220> FEATURE:
<223> OTHER INFORMATION: sequence of 5D5A5 VH

<400> SEQUENCE: 3

Gln Val Gln Leu Gln Gln Ser Gly Ala Glu Leu Ala Lys Pro Gly Ala
1               5                   10                  15

Ser Val Lys Met Ser Cys Lys Thr Ser Gly Tyr Ser Phe Ser Ser Tyr
            20                  25                  30

Trp Met His Trp Val Lys Gln Arg Pro Gly Gln Gly Leu Glu Trp Ile
            35                  40                  45

Gly Tyr Ile Asn Pro Ser Thr Gly Tyr Thr Glu Asn Asn Gln Lys Phe
 50                  55                  60

Lys Asp Lys Val Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
            85                  90                  95

Ala Arg Ser Gly Arg Leu Tyr Phe Asp Val Trp Gly Ala Gly Thr Thr
                100                 105                 110

```
Val Thr Val Ser Ser
        115

<210> SEQ ID NO 4
<211> LENGTH: 111
<212> TYPE: PRT
<213> ORGANISM: Artificial Sequence
<220> FEATURE:
<223> OTHER INFORMATION: sequence of 5D5A5 VL

<400> SEQUENCE: 4

Asp Ile Val Leu Thr Gln Ser Pro Ser Leu Ala Val Ser Leu Gly
1               5                   10                  15

Gln Arg Ala Thr Ile Ser Cys Arg Ala Ser Glu Ser Ile Asp Leu Tyr
            20                  25                  30

Gly Phe Thr Phe Met His Trp Tyr Gln Gln Lys Pro Gly Gln Pro Pro
        35                  40                  45

Lys Ile Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Thr His
                85                  90                  95

Glu Asp Pro Tyr Thr Phe Gly Gly Gly Thr Lys Leu Glu Ile Lys
            100                 105                 110

<210> SEQ ID NO 5
<211> LENGTH: 234
<212> TYPE: PRT
<213> ORGANISM: Artificial Sequence
<220> FEATURE:
<223> OTHER INFORMATION: hinge-CH2CH3 of human IgG1

<400> SEQUENCE: 5

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230

<210> SEQ ID NO 6
<211> LENGTH: 46
<212> TYPE: PRT
<213> ORGANISM: Artificial Sequence
<220> FEATURE:
<223> OTHER INFORMATION: human CD8 stalk

<400> SEQUENCE: 6

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45

<210> SEQ ID NO 7
<211> LENGTH: 20
<212> TYPE: PRT
<213> ORGANISM: Artificial Sequence
<220> FEATURE:
<223> OTHER INFORMATION: human IgG1 hinge

<400> SEQUENCE: 7

Ala Glu Pro Lys Ser Pro Asp Lys Thr His Thr Cys Pro Pro Cys Pro
1               5                   10                  15

Lys Asp Pro Lys
            20

<210> SEQ ID NO 8
<211> LENGTH: 57
<212> TYPE: PRT
<213> ORGANISM: Artificial Sequence
<220> FEATURE:
<223> OTHER INFORMATION: sequence of coiled coil domain (Kinesin motor
      protein: parallel homodimer)

<400> SEQUENCE: 8

Met His Ala Ala Leu Ser Thr Glu Val Val His Leu Arg Gln Arg Thr
1               5                   10                  15

Glu Glu Leu Leu Arg Cys Asn Glu Gln Gln Ala Ala Glu Leu Glu Thr
            20                  25                  30

Cys Lys Glu Gln Leu Phe Gln Ser Asn Met Glu Arg Lys Glu Leu His
        35                  40                  45

Asn Thr Val Met Asp Leu Arg Gly Asn
    50                  55

<210> SEQ ID NO 9
<211> LENGTH: 50
<212> TYPE: PRT
<213> ORGANISM: Artificial Sequence
<220> FEATURE:
<223> OTHER INFORMATION: sequence of coiled coil domain (Hepatitis D
      delta antigen: parallel homodimer)
```

<400> SEQUENCE: 9

```
Gly Arg Glu Asp Ile Leu Glu Gln Trp Val Ser Gly Arg Lys Lys Leu
1               5                   10                  15

Glu Glu Leu Glu Arg Asp Leu Arg Lys Leu Lys Lys Lys Ile Lys Lys
            20                  25                  30

Leu Glu Glu Asp Asn Pro Trp Leu Gly Asn Ile Lys Gly Ile Ile Gly
        35                  40                  45

Lys Tyr
    50
```

<210> SEQ ID NO 10
<211> LENGTH: 61
<212> TYPE: PRT
<213> ORGANISM: Artificial Sequence
<220> FEATURE:
<223> OTHER INFORMATION: sequence of coiled coil domain (Archaeal box
      C/D sRNP core protein: anti-parallel heterodimer)

<400> SEQUENCE: 10

```
Arg Tyr Val Val Ala Leu Val Lys Ala Leu Glu Glu Ile Asp Glu Ser
1               5                   10                  15

Ile Asn Met Leu Asn Glu Lys Leu Glu Asp Ile Arg Ala Val Lys Glu
            20                  25                  30

Ser Glu Ile Thr Glu Lys Phe Glu Lys Lys Ile Arg Glu Leu Arg Glu
        35                  40                  45

Leu Arg Arg Asp Val Glu Arg Glu Ile Glu Glu Val Met
    50                  55                  60
```

<210> SEQ ID NO 11
<211> LENGTH: 31
<212> TYPE: PRT
<213> ORGANISM: Artificial Sequence
<220> FEATURE:
<223> OTHER INFORMATION: sequence of coiled coil domain (Mannose-binding
      protein A: parallel homotrimer)

<400> SEQUENCE: 11

```
Ala Ile Glu Val Lys Leu Ala Asn Met Glu Ala Glu Ile Asn Thr Leu
1               5                   10                  15

Lys Ser Lys Leu Glu Leu Thr Asn Lys Leu His Ala Phe Ser Met
            20                  25                  30
```

<210> SEQ ID NO 12
<211> LENGTH: 29
<212> TYPE: PRT
<213> ORGANISM: Artificial Sequence
<220> FEATURE:
<223> OTHER INFORMATION: sequence of coiled coil domain (Coiled-coil
      serine-rich protein 1: parallel homotrimer)

<400> SEQUENCE: 12

```
Glu Trp Glu Ala Leu Glu Lys Lys Leu Ala Ala Leu Glu Ser Lys Leu
1               5                   10                  15

Gln Ala Leu Glu Lys Lys Leu Glu Ala Leu Glu His Gly
            20                  25
```

<210> SEQ ID NO 13
<211> LENGTH: 24
<212> TYPE: PRT
<213> ORGANISM: Artificial Sequence

```
<220> FEATURE:
<223> OTHER INFORMATION: sequence of coiled coil domain (Polypeptide
      release factor 2: anti-parallel heterotrimer Chain A)

<400> SEQUENCE: 13

Ile Asn Pro Val Asn Asn Arg Ile Gln Asp Leu Thr Glu Arg Ser Asp
1               5                   10                  15

Val Leu Arg Gly Tyr Leu Asp Tyr
            20

<210> SEQ ID NO 14
<211> LENGTH: 51
<212> TYPE: PRT
<213> ORGANISM: Artificial Sequence
<220> FEATURE:
<223> OTHER INFORMATION: sequence of coiled coil domain (Polypeptide
      release factor 2: anti-parallel heterotrimer Chain B)

<400> SEQUENCE: 14

Val Val Asp Thr Leu Asp Gln Met Lys Gln Gly Leu Glu Asp Val Ser
1               5                   10                  15

Gly Leu Leu Glu Leu Ala Val Glu Ala Asp Asp Glu Glu Thr Phe Asn
            20                  25                  30

Glu Ala Val Ala Glu Leu Asp Ala Leu Glu Glu Lys Leu Ala Gln Leu
        35                  40                  45

Glu Phe Arg
    50

<210> SEQ ID NO 15
<211> LENGTH: 51
<212> TYPE: PRT
<213> ORGANISM: Artificial Sequence
<220> FEATURE:
<223> OTHER INFORMATION: sequence of coiled coil domain (SNAP-25 and
      SNARE: parallel heterotetramer Chain A)

<400> SEQUENCE: 15

Ile Glu Thr Arg His Ser Glu Ile Ile Lys Leu Glu Asn Ser Ile Arg
1               5                   10                  15

Glu Leu His Asp Met Phe Met Asp Met Ala Met Leu Val Glu Ser Gln
            20                  25                  30

Gly Glu Met Ile Asp Arg Ile Glu Tyr Asn Val Glu His Ala Val Asp
        35                  40                  45

Tyr Val Glu
    50

<210> SEQ ID NO 16
<211> LENGTH: 67
<212> TYPE: PRT
<213> ORGANISM: Artificial Sequence
<220> FEATURE:
<223> OTHER INFORMATION: sequence of coiled coil domain (SNAP-25 and
      SNARE: parallel heterotetramer Chain B)

<400> SEQUENCE: 16

Ala Leu Ser Glu Ile Glu Thr Arg His Ser Glu Ile Ile Lys Leu Glu
1               5                   10                  15

Asn Ser Ile Arg Glu Leu His Asp Met Phe Met Asp Met Ala Met Leu
            20                  25                  30

Val Glu Ser Gln Gly Glu Met Ile Asp Arg Ile Glu Tyr Asn Val Glu
        35                  40                  45
```

His Ala Val Asp Tyr Val Glu Arg Ala Val Ser Asp Thr Lys Lys Ala
            50                  55                  60

Val Lys Tyr
 65

<210> SEQ ID NO 17
<211> LENGTH: 69
<212> TYPE: PRT
<213> ORGANISM: Artificial Sequence
<220> FEATURE:
<223> OTHER INFORMATION: sequence of coiled coil domain (Chain C)

<400> SEQUENCE: 17

Glu Leu Glu Glu Met Gln Arg Arg Ala Asp Gln Leu Ala Asp Glu Ser
 1               5                  10                  15

Leu Glu Ser Thr Arg Arg Met Leu Gln Leu Val Glu Glu Ser Lys Asp
            20                  25                  30

Ala Gly Ile Arg Thr Leu Val Met Leu Asp Glu Gln Gly Glu Gln Leu
        35                  40                  45

Glu Arg Ile Glu Glu Gly Met Asp Gln Ile Asn Lys Asp Met Lys Glu
    50                  55                  60

Ala Glu Lys Asn Leu
 65

<210> SEQ ID NO 18
<211> LENGTH: 51
<212> TYPE: PRT
<213> ORGANISM: Artificial Sequence
<220> FEATURE:
<223> OTHER INFORMATION: sequence of coiled coil domain (SNAP-25 and
      SNARE: parallel heterotetramer Chain D)

<400> SEQUENCE: 18

Ile Glu Thr Arg His Ser Glu Ile Ile Lys Leu Glu Asn Ser Ile Arg
 1               5                  10                  15

Glu Leu His Asp Met Phe Met Asp Met Ala Met Leu Val Glu Ser Gln
            20                  25                  30

Gly Glu Met Ile Asp Arg Ile Glu Tyr Asn Val Glu His Ala Val Asp
        35                  40                  45

Tyr Val Glu
    50

<210> SEQ ID NO 19
<211> LENGTH: 20
<212> TYPE: PRT
<213> ORGANISM: Artificial Sequence
<220> FEATURE:
<223> OTHER INFORMATION: sequence of coiled coil domain (Lac repressor:
      parallel homotetramer)

<400> SEQUENCE: 19

Ser Pro Arg Ala Leu Ala Asp Ser Leu Met Gln Leu Ala Arg Gln Val
 1               5                  10                  15

Ser Arg Leu Glu
            20

<210> SEQ ID NO 20
<211> LENGTH: 136
<212> TYPE: PRT
<213> ORGANISM: Artificial Sequence
<220> FEATURE:

<223> OTHER INFORMATION: sequence of coiled coil domain (Apolipoprotein
      E: anti-parallel heterotetramer)

<400> SEQUENCE: 20

Ser Gly Gln Arg Trp Glu Leu Ala Leu Gly Arg Phe Trp Asp Tyr Leu
1               5                   10                  15

Arg Trp Val Gln Thr Leu Ser Glu Gln Val Gln Glu Glu Leu Leu Ser
            20                  25                  30

Ser Gln Val Thr Gln Glu Leu Arg Ala Leu Met Asp Glu Thr Met Lys
        35                  40                  45

Glu Leu Lys Ala Tyr Lys Ser Glu Leu Glu Glu Gln Leu Thr Ala Arg
    50                  55                  60

Leu Ser Lys Glu Leu Gln Ala Ala Gln Ala Arg Leu Gly Ala Asp Met
65                  70                  75                  80

Glu Asp Val Cys Gly Arg Leu Val Gln Tyr Arg Gly Glu Val Gln Ala
                85                  90                  95

Met Leu Gly Gln Ser Thr Glu Glu Leu Arg Val Arg Leu Ala Ser His
            100                 105                 110

Leu Arg Lys Leu Arg Lys Arg Leu Leu Arg Asp Ala Asp Asp Leu Gln
        115                 120                 125

Lys Arg Leu Ala Val Tyr Gln Ala
    130                 135

<210> SEQ ID NO 21
<211> LENGTH: 45
<212> TYPE: PRT
<213> ORGANISM: Artificial Sequence
<220> FEATURE:
<223> OTHER INFORMATION: COMP coiled-coil domain

<400> SEQUENCE: 21

Asp Leu Gly Pro Gln Met Leu Arg Glu Leu Gln Glu Thr Asn Ala Ala
1               5                   10                  15

Leu Gln Asp Val Arg Glu Leu Leu Arg Gln Gln Val Arg Glu Ile Thr
            20                  25                  30

Phe Leu Lys Asn Thr Val Met Glu Cys Asp Ala Cys Gly
        35                  40                  45

<210> SEQ ID NO 22
<211> LENGTH: 21
<212> TYPE: PRT
<213> ORGANISM: Artificial Sequence
<220> FEATURE:
<223> OTHER INFORMATION: signal peptide derived from TCR beta chain

<400> SEQUENCE: 22

Met Gly Thr Ser Leu Leu Cys Trp Met Ala Leu Cys Leu Leu Gly Ala
1               5                   10                  15

Asp His Ala Asp Gly
            20

<210> SEQ ID NO 23
<211> LENGTH: 21
<212> TYPE: PRT
<213> ORGANISM: Artificial Sequence
<220> FEATURE:
<223> OTHER INFORMATION: signal peptide derived from IgG1

<400> SEQUENCE: 23

Met Ser Leu Pro Val Thr Ala Leu Leu Leu Pro Leu Ala Leu Leu Leu
1               5                   10                  15

His Ala Ala Arg Pro
            20

<210> SEQ ID NO 24
<211> LENGTH: 20
<212> TYPE: PRT
<213> ORGANISM: Artificial Sequence
<220> FEATURE:
<223> OTHER INFORMATION: signal peptide derived from CD8a

<400> SEQUENCE: 24

Met Ala Val Pro Thr Gln Val Leu Gly Leu Leu Leu Leu Trp Leu Thr
1               5                   10                  15

Asp Ala Arg Cys
            20

<210> SEQ ID NO 25
<211> LENGTH: 112
<212> TYPE: PRT
<213> ORGANISM: Artificial Sequence
<220> FEATURE:
<223> OTHER INFORMATION: CD3 Z endodomain

<400> SEQUENCE: 25

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 26
<211> LENGTH: 152
<212> TYPE: PRT
<213> ORGANISM: Artificial Sequence
<220> FEATURE:
<223> OTHER INFORMATION: CD28 and CD3 Zeta endodomains

<400> SEQUENCE: 26

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Val Lys Phe Ser Arg Ser Ala
        35                  40                  45

Asp Ala Pro Ala Tyr Gln Gln Gly Gln Asn Gln Leu Tyr Asn Glu Leu
    50                  55                  60

Asn Leu Gly Arg Arg Glu Glu Tyr Asp Val Leu Asp Lys Arg Gly
65                  70                  75                  80

Arg Asp Pro Glu Met Gly Gly Lys Pro Arg Arg Lys Asn Pro Gln Glu
                85                  90                  95

```
Gly Leu Tyr Asn Glu Leu Gln Lys Asp Lys Met Ala Glu Ala Tyr Ser
                100                 105                 110
Glu Ile Gly Met Lys Gly Glu Arg Arg Arg Gly Lys Gly His Asp Gly
            115                 120                 125
Leu Tyr Gln Gly Leu Ser Thr Ala Thr Lys Asp Thr Tyr Asp Ala Leu
        130                 135                 140
His Met Gln Ala Leu Pro Pro Arg
145                 150

<210> SEQ ID NO 27
<211> LENGTH: 188
<212> TYPE: PRT
<213> ORGANISM: Artificial Sequence
<220> FEATURE:
<223> OTHER INFORMATION: CD28, OX40 and CD3 Zeta endodomains

<400> SEQUENCE: 27

Ser Lys Arg Ser Arg Leu Leu His Ser Asp Tyr Met Asn Met Thr Pro
1               5                   10                  15
Arg Arg Pro Gly Pro Thr Arg Lys His Tyr Gln Pro Tyr Ala Pro Pro
            20                  25                  30
Arg Asp Phe Ala Ala Tyr Arg Ser Arg Asp Gln Arg Leu Pro Pro Asp
        35                  40                  45
Ala His Lys Pro Pro Gly Gly Gly Ser Phe Arg Thr Pro Ile Gln Glu
    50                  55                  60
Glu Gln Ala Asp Ala His Ser Thr Leu Ala Lys Ile Arg Val Lys Phe
65                  70                  75                  80
Ser Arg Ser Ala Asp Ala Pro Ala Tyr Gln Gln Gly Gln Asn Gln Leu
                85                  90                  95
Tyr Asn Glu Leu Asn Leu Gly Arg Arg Glu Glu Tyr Asp Val Leu Asp
                100                 105                 110
Lys Arg Arg Gly Arg Asp Pro Glu Met Gly Gly Lys Pro Arg Arg Lys
            115                 120                 125
Asn Pro Gln Glu Gly Leu Tyr Asn Glu Leu Gln Lys Asp Lys Met Ala
        130                 135                 140
Glu Ala Tyr Ser Glu Ile Gly Met Lys Gly Glu Arg Arg Arg Gly Lys
145                 150                 155                 160
Gly His Asp Gly Leu Tyr Gln Gly Leu Ser Thr Ala Thr Lys Asp Thr
                165                 170                 175
Tyr Asp Ala Leu His Met Gln Ala Leu Pro Pro Arg
                180                 185

<210> SEQ ID NO 28
<211> LENGTH: 38
<212> TYPE: PRT
<213> ORGANISM: Artificial Sequence
<220> FEATURE:
<223> OTHER INFORMATION: ICOS endodomain

<400> SEQUENCE: 28

Cys Trp Leu Thr Lys Lys Lys Tyr Ser Ser Val His Asp Pro Asn
1               5                   10                  15
Gly Glu Tyr Met Phe Met Arg Ala Val Asn Thr Ala Lys Lys Ser Arg
            20                  25                  30
Leu Thr Asp Val Thr Leu
        35

<210> SEQ ID NO 29
```

<211> LENGTH: 48
<212> TYPE: PRT
<213> ORGANISM: Artificial Sequence
<220> FEATURE:
<223> OTHER INFORMATION: CD27 endodomain

<400> SEQUENCE: 29

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 30
<211> LENGTH: 111
<212> TYPE: PRT
<213> ORGANISM: Artificial Sequence
<220> FEATURE:
<223> OTHER INFORMATION: BTLA endodomain

<400> SEQUENCE: 30

Arg Arg His Gln Gly Lys Gln Asn Glu Leu Ser Asp Thr Ala Gly Arg
1               5                   10                  15

Glu Ile Asn Leu Val Asp Ala His Leu Lys Ser Glu Gln Thr Glu Ala
            20                  25                  30

Ser Thr Arg Gln Asn Ser Gln Val Leu Leu Ser Glu Thr Gly Ile Tyr
        35                  40                  45

Asp Asn Asp Pro Asp Leu Cys Phe Arg Met Gln Glu Gly Ser Glu Val
    50                  55                  60

Tyr Ser Asn Pro Cys Leu Glu Glu Asn Lys Pro Gly Ile Val Tyr Ala
65                  70                  75                  80

Ser Leu Asn His Ser Val Ile Gly Pro Asn Ser Arg Leu Ala Arg Asn
                85                  90                  95

Val Lys Glu Ala Pro Thr Glu Tyr Ala Ser Ile Cys Val Arg Ser
            100                 105                 110

<210> SEQ ID NO 31
<211> LENGTH: 188
<212> TYPE: PRT
<213> ORGANISM: Artificial Sequence
<220> FEATURE:
<223> OTHER INFORMATION: CD30 endodomain

<400> SEQUENCE: 31

His Arg Arg Ala Cys Arg Lys Arg Ile Arg Gln Lys Leu His Leu Cys
1               5                   10                  15

Tyr Pro Val Gln Thr Ser Gln Pro Lys Leu Glu Leu Val Asp Ser Arg
            20                  25                  30

Pro Arg Arg Ser Ser Thr Gln Leu Arg Ser Gly Ala Ser Val Thr Glu
        35                  40                  45

Pro Val Ala Glu Glu Arg Gly Leu Met Ser Gln Pro Leu Met Glu Thr
    50                  55                  60

Cys His Ser Val Gly Ala Ala Tyr Leu Glu Ser Leu Pro Leu Gln Asp
65                  70                  75                  80

Ala Ser Pro Ala Gly Gly Pro Ser Ser Pro Arg Asp Leu Pro Glu Pro
                85                  90                  95

Arg Val Ser Thr Glu His Thr Asn Asn Lys Ile Glu Lys Ile Tyr Ile
            100                 105                 110

```
Met Lys Ala Asp Thr Val Ile Val Gly Thr Val Lys Ala Glu Leu Pro
            115                 120                 125

Glu Gly Arg Gly Leu Ala Gly Pro Ala Glu Pro Glu Leu Glu Glu Glu
        130                 135                 140

Leu Glu Ala Asp His Thr Pro His Tyr Pro Glu Gln Glu Thr Glu Pro
145                 150                 155                 160

Pro Leu Gly Ser Cys Ser Asp Val Met Leu Ser Val Glu Glu Glu Gly
                165                 170                 175

Lys Glu Asp Pro Leu Pro Thr Ala Ala Ser Gly Lys
            180                 185

<210> SEQ ID NO 32
<211> LENGTH: 58
<212> TYPE: PRT
<213> ORGANISM: Artificial Sequence
<220> FEATURE:
<223> OTHER INFORMATION: GITR endodomain

<400> SEQUENCE: 32

Gln Leu Gly Leu His Ile Trp Gln Leu Arg Ser Gln Cys Met Trp Pro
1               5                   10                  15

Arg Glu Thr Gln Leu Leu Leu Glu Val Pro Pro Ser Thr Glu Asp Ala
            20                  25                  30

Arg Ser Cys Gln Phe Pro Glu Glu Glu Arg Gly Glu Arg Ser Ala Glu
        35                  40                  45

Glu Lys Gly Arg Leu Gly Asp Leu Trp Val
    50                  55

<210> SEQ ID NO 33
<211> LENGTH: 60
<212> TYPE: PRT
<213> ORGANISM: Artificial Sequence
<220> FEATURE:
<223> OTHER INFORMATION: HVEM endodomain

<400> SEQUENCE: 33

Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60

<210> SEQ ID NO 34
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 34

Tyr His Ala Asp Tyr Tyr Lys Gln Arg Leu Ile His Asp Val Glu Met
1               5                   10                  15

Asn Pro Gly Pro
            20

<210> SEQ ID NO 35
<211> LENGTH: 20
<212> TYPE: PRT
```

```
<213> ORGANISM: Artificial Sequence
<220> FEATURE:
<223> OTHER INFORMATION: cleavage site, 2A-like sequence

<400> SEQUENCE: 35

His Tyr Ala Gly Tyr Phe Ala Asp Leu Leu Ile His Asp Ile Glu Thr
1               5                   10                  15

Asn Pro Gly Pro
            20

<210> SEQ ID NO 36
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 36

Gln Cys Thr Asn Tyr Ala Leu Leu Lys Leu Ala Gly Asp Val Glu Ser
1               5                   10                  15

Asn Pro Gly Pro
            20

<210> SEQ ID NO 37
<211> LENGTH: 19
<212> TYPE: PRT
<213> ORGANISM: Artificial Sequence
<220> FEATURE:
<223> OTHER INFORMATION: cleavage site, 2A-like sequence

<400> SEQUENCE: 37

Ala Thr Asn Phe Ser Leu Leu Lys Gln Ala Gly Asp Val Glu Glu Asn
1               5                   10                  15

Pro Gly Pro

<210> SEQ ID NO 38
<211> LENGTH: 19
<212> TYPE: PRT
<213> ORGANISM: Artificial Sequence
<220> FEATURE:
<223> OTHER INFORMATION: cleavage site, 2A-like sequence

<400> SEQUENCE: 38

Ala Ala Arg Gln Met Leu Leu Leu Leu Ser Gly Asp Val Glu Thr Asn
1               5                   10                  15

Pro Gly Pro

<210> SEQ ID NO 39
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 39

Arg Ala Glu Gly Arg Gly Ser Leu Leu Thr Cys Gly Asp Val Glu Glu
1               5                   10                  15

Asn Pro Gly Pro
            20

<210> SEQ ID NO 40
<211> LENGTH: 20
<212> TYPE: PRT
<213> ORGANISM: Artificial Sequence
```

```
<220> FEATURE:
<223> OTHER INFORMATION: cleavage site, 2A-like sequence

<400> SEQUENCE: 40

Thr Arg Ala Glu Ile Glu Asp Glu Leu Ile Arg Ala Gly Ile Glu Ser
1               5                   10                  15

Asn Pro Gly Pro
            20

<210> SEQ ID NO 41
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 41

Thr Arg Ala Glu Ile Glu Asp Glu Leu Ile Arg Ala Asp Ile Glu Ser
1               5                   10                  15

Asn Pro Gly Pro
            20

<210> SEQ ID NO 42
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 42

Ala Lys Phe Gln Ile Asp Lys Ile Leu Ile Ser Gly Asp Val Glu Leu
1               5                   10                  15

Asn Pro Gly Pro
            20

<210> SEQ ID NO 43
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 43

Ser Ser Ile Ile Arg Thr Lys Met Leu Val Ser Gly Asp Val Glu Glu
1               5                   10                  15

Asn Pro Gly Pro
            20

<210> SEQ ID NO 44
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 44

Cys Asp Ala Gln Arg Gln Lys Leu Leu Leu Ser Gly Asp Ile Glu Gln
1               5                   10                  15

Asn Pro Gly Pro
            20

<210> SEQ ID NO 45
<211> LENGTH: 20
<212> TYPE: PRT
```

<213> ORGANISM: Artificial Sequence
<220> FEATURE:
<223> OTHER INFORMATION: cleavage site, 2A-like sequence

<400> SEQUENCE: 45

Tyr Pro Ile Asp Phe Gly Gly Phe Leu Val Lys Ala Asp Ser Glu Phe
1               5                   10                  15

Asn Pro Gly Pro
            20

<210> SEQ ID NO 46
<211> LENGTH: 595
<212> TYPE: PRT
<213> ORGANISM: Artificial Sequence
<220> FEATURE:
<223> OTHER INFORMATION: inhibitor domain, PTPN6

<400> SEQUENCE: 46

Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
                20                  25                  30

Arg Lys Asn Gln Gly Asp Phe Ser Leu Ser Val Arg Val Gly Asp Gln
            35                  40                  45

Val Thr His Ile Arg Ile Gln Asn Ser Gly Asp Phe Tyr Asp Leu Tyr
        50                  55                  60

Gly Gly Glu Lys Phe Ala Thr Leu Thr Glu Leu Val Glu Tyr Tyr Thr
65                  70                  75                  80

Gln Gln Gln Gly Val Leu Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Glu Asn Lys Gly
            260                 265                 270

Lys Asn Arg Tyr Lys Asn Ile Leu Pro Phe Asp His Ser Arg Val Ile
        275                 280                 285

Leu Gln Gly Arg Asp Ser Asn Ile Pro Gly Ser Asp Tyr Ile Asn Ala
    290                 295                 300

```
Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
            325                 330                 335

Gln Met Ala Trp Gln Glu Asn Ser Arg Val Ile Val Met Thr Thr Arg
        340                 345                 350

Glu Val Glu Lys Gly Arg Asn Lys Cys Val Pro Tyr Trp Pro Glu Val
    355                 360                 365

Gly Met Gln Arg Ala Tyr Gly Pro Tyr Ser Val Thr Asn Cys Gly Glu
370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
                405                 410                 415

Trp Pro Asp His Gly Val Pro Ser Glu Pro Gly Gly Val Leu Ser Phe
            420                 425                 430

Leu Asp Gln Ile Asn Gln Arg Gln Glu Ser Leu Pro His Ala Gly Pro
        435                 440                 445

Ile Ile Val His Cys Ser Ala Gly Ile Gly Arg Thr Gly Thr Ile Ile
    450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
                485                 490                 495

Gly Met Val Gln Thr Glu Ala Gln Tyr Lys Phe Ile Tyr Val Ala Ile
            500                 505                 510

Ala Gln Phe Ile Glu Thr Thr Lys Lys Lys Leu Glu Val Leu Gln Ser
        515                 520                 525

Gln Lys Gly Gln Glu Ser Glu Tyr Gly Asn Ile Thr Tyr Pro Pro Ala
    530                 535                 540

Met Lys Asn Ala His Ala Lys Ala Ser Arg Thr Ser Ser Lys His Lys
545                 550                 555                 560

Glu Asp Val Tyr Glu Asn Leu His Thr Lys Asn Lys Arg Glu Glu Lys
                565                 570                 575

Val Lys Lys Gln Arg Ser Ala Asp Lys Glu Lys Ser Lys Gly Ser Leu
            580                 585                 590

Lys Arg Lys
    595

<210> SEQ ID NO 47
<211> LENGTH: 272
<212> TYPE: PRT
<213> ORGANISM: Artificial Sequence
<220> FEATURE:
<223> OTHER INFORMATION: inhibitor domain, phosphatase domain of PTPN6

<400> SEQUENCE: 47

Phe Trp Glu Glu Phe Glu Ser Leu Gln Lys Gln Glu Val Lys Asn Leu
1               5                   10                  15

His Gln Arg Leu Glu Gly Gln Arg Pro Glu Asn Lys Gly Lys Asn Arg
            20                  25                  30

Tyr Lys Asn Ile Leu Pro Phe Asp His Ser Arg Val Ile Leu Gln Gly
        35                  40                  45

Arg Asp Ser Asn Ile Pro Gly Ser Asp Tyr Ile Asn Ala Asn Tyr Ile
    50                  55                  60
```

-continued

```
Lys Asn Gln Leu Leu Gly Pro Asp Glu Asn Ala Lys Thr Tyr Ile Ala
 65                  70                  75                  80

Ser Gln Gly Cys Leu Glu Ala Thr Val Asn Asp Phe Trp Gln Met Ala
                 85                  90                  95

Trp Gln Glu Asn Ser Arg Val Ile Val Met Thr Thr Arg Glu Val Glu
            100                 105                 110

Lys Gly Arg Asn Lys Cys Val Pro Tyr Trp Pro Glu Val Gly Met Gln
        115                 120                 125

Arg Ala Tyr Gly Pro Tyr Ser Val Thr Asn Cys Gly Glu His Asp Thr
    130                 135                 140

Thr Glu Tyr Lys Leu Arg Thr Leu Gln Val Ser Pro Leu Asp Asn Gly
145                 150                 155                 160

Asp Leu Ile Arg Glu Ile Trp His Tyr Gln Tyr Leu Ser Trp Pro Asp
                165                 170                 175

His Gly Val Pro Ser Glu Pro Gly Gly Val Leu Ser Phe Leu Asp Gln
            180                 185                 190

Ile Asn Gln Arg Gln Glu Ser Leu Pro His Ala Gly Pro Ile Ile Val
        195                 200                 205

His Cys Ser Ala Gly Ile Gly Arg Thr Gly Thr Ile Ile Val Ile Asp
    210                 215                 220

Met Leu Met Glu Asn Ile Ser Thr Lys Gly Leu Asp Cys Asp Ile Asp
225                 230                 235                 240

Ile Gln Lys Thr Ile Gln Met Val Arg Ala Gln Arg Ser Gly Met Val
                245                 250                 255

Gln Thr Glu Ala Gln Tyr Lys Phe Ile Tyr Val Ala Ile Ala Gln Phe
            260                 265                 270
```

<210> SEQ ID NO 48
<211> LENGTH: 97
<212> TYPE: PRT
<213> ORGANISM: Artificial Sequence
<220> FEATURE:
<223> OTHER INFORMATION: PDCD1 endodomain

<400> SEQUENCE: 48

```
Cys Ser Arg Ala Ala Arg Gly Thr Ile Gly Ala Arg Arg Thr Gly Gln
  1               5                  10                  15

Pro Leu Lys Glu Asp Pro Ser Ala Val Pro Val Phe Ser Val Asp Tyr
                 20                  25                  30

Gly Glu Leu Asp Phe Gln Trp Arg Glu Lys Thr Pro Glu Pro Pro Val
             35                  40                  45

Pro Cys Val Pro Glu Gln Thr Glu Tyr Ala Thr Ile Val Phe Pro Ser
     50                  55                  60

Gly Met Gly Thr Ser Ser Pro Ala Arg Arg Gly Ser Ala Asp Gly Pro
 65                  70                  75                  80

Arg Ser Ala Gln Pro Leu Arg Pro Glu Asp Gly His Cys Ser Trp Pro
                 85                  90                  95

Leu
```

<210> SEQ ID NO 49
<211> LENGTH: 141
<212> TYPE: PRT
<213> ORGANISM: Artificial Sequence
<220> FEATURE:
<223> OTHER INFORMATION: BTLA4 endodomain

<400> SEQUENCE: 49

| Lys | Leu | Gln | Arg | Arg | Trp | Lys | Arg | Thr | Gln | Ser | Gln | Gln | Gly | Leu | Gln |
| 1 | | | | 5 | | | | | 10 | | | | | 15 | |
| Glu | Asn | Ser | Ser | Gly | Gln | Ser | Phe | Phe | Val | Arg | Asn | Lys | Lys | Val | Arg |
| | | | 20 | | | | | 25 | | | | | 30 | | |
| Arg | Ala | Pro | Leu | Ser | Glu | Gly | Pro | His | Ser | Leu | Gly | Cys | Tyr | Asn | Pro |
| | | | 35 | | | | | 40 | | | | | 45 | | |
| Met | Met | Glu | Asp | Gly | Ile | Ser | Tyr | Thr | Thr | Leu | Arg | Phe | Pro | Glu | Met |
| | 50 | | | | | 55 | | | | | 60 | | | | |
| Asn | Ile | Pro | Arg | Thr | Gly | Asp | Ala | Glu | Ser | Ser | Glu | Met | Gln | Arg | Pro |
| 65 | | | | | 70 | | | | | 75 | | | | | 80 |
| Pro | Pro | Asp | Cys | Asp | Asp | Thr | Val | Thr | Tyr | Ser | Ala | Leu | His | Lys | Arg |
| | | | | 85 | | | | | 90 | | | | | 95 | |
| Gln | Val | Gly | Asp | Tyr | Glu | Asn | Val | Ile | Pro | Asp | Phe | Pro | Glu | Asp | Glu |
| | | | | 100 | | | | | 105 | | | | | 110 | |
| Gly | Ile | His | Tyr | Ser | Glu | Leu | Ile | Gln | Phe | Gly | Val | Gly | Glu | Arg | Pro |
| | | | | 115 | | | | | 120 | | | | | 125 | |
| Gln | Ala | Gln | Glu | Asn | Val | Asp | Tyr | Val | Ile | Leu | Lys | His |
| | | 130 | | | | | 135 | | | | | 140 |

<210> SEQ ID NO 50
<211> LENGTH: 168
<212> TYPE: PRT
<213> ORGANISM: Artificial Sequence
<220> FEATURE:
<223> OTHER INFORMATION: LILRB1 endodomain

<400> SEQUENCE: 50

| Leu | Arg | His | Arg | Arg | Gln | Gly | Lys | His | Trp | Thr | Ser | Thr | Gln | Arg | Lys |
| 1 | | | | 5 | | | | | 10 | | | | | 15 | |
| Ala | Asp | Phe | Gln | His | Pro | Ala | Gly | Ala | Val | Gly | Pro | Glu | Pro | Thr | Asp |
| | | | 20 | | | | | 25 | | | | | 30 | | |
| Arg | Gly | Leu | Gln | Trp | Arg | Ser | Ser | Pro | Ala | Ala | Asp | Ala | Gln | Glu | Glu |
| | | | 35 | | | | | 40 | | | | | 45 | | |
| Asn | Leu | Tyr | Ala | Ala | Val | Lys | His | Thr | Gln | Pro | Glu | Asp | Gly | Val | Glu |
| | 50 | | | | | 55 | | | | | 60 | | | | |
| Met | Asp | Thr | Arg | Ser | Pro | His | Asp | Glu | Asp | Pro | Gln | Ala | Val | Thr | Tyr |
| 65 | | | | | 70 | | | | | 75 | | | | | 80 |
| Ala | Glu | Val | Lys | His | Ser | Arg | Pro | Arg | Arg | Glu | Met | Ala | Ser | Pro | Pro |
| | | | | 85 | | | | | 90 | | | | | 95 | |
| Ser | Pro | Leu | Ser | Gly | Glu | Phe | Leu | Asp | Thr | Lys | Asp | Arg | Gln | Ala | Glu |
| | | | | 100 | | | | | 105 | | | | | 110 | |
| Glu | Asp | Arg | Gln | Met | Asp | Thr | Glu | Ala | Ala | Ser | Glu | Ala | Pro | Gln |
| | | | 115 | | | | | 120 | | | | | 125 | |
| Asp | Val | Thr | Tyr | Ala | Gln | Leu | His | Ser | Leu | Thr | Leu | Arg | Arg | Glu | Ala |
| | | 130 | | | | | 135 | | | | | 140 | | | |
| Thr | Glu | Pro | Pro | Pro | Ser | Gln | Glu | Gly | Pro | Ser | Pro | Ala | Val | Pro | Ser |
| 145 | | | | | 150 | | | | | 155 | | | | | 160 |
| Ile | Tyr | Ala | Thr | Leu | Ala | Ile | His |
| | | | | 165 | | | |

<210> SEQ ID NO 51
<211> LENGTH: 101
<212> TYPE: PRT
<213> ORGANISM: Artificial Sequence
<220> FEATURE:

<223> OTHER INFORMATION: LAIR1 endodomain

<400> SEQUENCE: 51

His Arg Gln Asn Gln Ile Lys Gln Gly Pro Pro Arg Ser Lys Asp Glu
1               5                   10                  15

Glu Gln Lys Pro Gln Gln Arg Pro Asp Leu Ala Val Asp Val Leu Glu
            20                  25                  30

Arg Thr Ala Asp Lys Ala Thr Val Asn Gly Leu Pro Glu Lys Asp Arg
        35                  40                  45

Glu Thr Asp Thr Ser Ala Leu Ala Ala Gly Ser Ser Gln Glu Val Thr
    50                  55                  60

Tyr Ala Gln Leu Asp His Trp Ala Leu Thr Gln Arg Thr Ala Arg Ala
65                  70                  75                  80

Val Ser Pro Gln Ser Thr Lys Pro Met Ala Glu Ser Ile Thr Tyr Ala
                85                  90                  95

Ala Val Ala Arg His
            100

<210> SEQ ID NO 52
<211> LENGTH: 62
<212> TYPE: PRT
<213> ORGANISM: Artificial Sequence
<220> FEATURE:
<223> OTHER INFORMATION: CTLA4 endodomain

<400> SEQUENCE: 52

Phe Leu Leu Trp Ile Leu Ala Ala Val Ser Ser Gly Leu Phe Phe Tyr
1               5                   10                  15

Ser Phe Leu Leu Thr Ala Val Ser Leu Ser Lys Met Leu Lys Lys Arg
            20                  25                  30

Ser Pro Leu Thr Thr Gly Val Tyr Val Lys Met Pro Pro Thr Glu Pro
        35                  40                  45

Glu Cys Glu Lys Gln Phe Gln Pro Tyr Phe Ile Pro Ile Asn
    50                  55                  60

<210> SEQ ID NO 53
<211> LENGTH: 111
<212> TYPE: PRT
<213> ORGANISM: Artificial Sequence
<220> FEATURE:
<223> OTHER INFORMATION: KIR2DL1 endodomain

<400> SEQUENCE: 53

Gly Asn Ser Arg His Leu His Val Leu Ile Gly Thr Ser Val Val Ile
1               5                   10                  15

Ile Pro Phe Ala Ile Leu Leu Phe Phe Leu Leu His Arg Trp Cys Ala
            20                  25                  30

Asn Lys Lys Asn Ala Val Val Met Asp Gln Glu Pro Ala Gly Asn Arg
        35                  40                  45

Thr Val Asn Arg Glu Asp Ser Asp Glu Gln Asp Pro Gln Glu Val Thr
    50                  55                  60

Tyr Thr Gln Leu Asn His Cys Val Phe Thr Gln Arg Lys Ile Thr Arg
65                  70                  75                  80

Pro Ser Gln Arg Pro Lys Thr Pro Pro Thr Asp Ile Ile Val Tyr Thr
                85                  90                  95

Glu Leu Pro Asn Ala Glu Ser Arg Ser Lys Val Val Ser Cys Pro
            100                 105                 110

```
<210> SEQ ID NO 54
<211> LENGTH: 143
<212> TYPE: PRT
<213> ORGANISM: Artificial Sequence
<220> FEATURE:
<223> OTHER INFORMATION: KIR2DL4 endodomain

<400> SEQUENCE: 54

Gly Ile Ala Arg His Leu His Ala Val Ile Arg Tyr Ser Val Ala Ile
1               5                   10                  15

Ile Leu Phe Thr Ile Leu Pro Phe Phe Leu Leu His Arg Trp Cys Ser
            20                  25                  30

Lys Lys Lys Glu Asn Ala Ala Val Met Asn Gln Glu Pro Ala Gly His
        35                  40                  45

Arg Thr Val Asn Arg Glu Asp Ser Asp Glu Gln Asp Pro Gln Glu Val
    50                  55                  60

Thr Tyr Ala Gln Leu Asp His Cys Ile Phe Thr Gln Arg Lys Ile Thr
65                  70                  75                  80

Gly Pro Ser Gln Arg Ser Lys Arg Pro Ser Thr Asp Thr Ser Val Cys
                85                  90                  95

Ile Glu Leu Pro Asn Ala Glu Pro Arg Ala Leu Ser Pro Ala His Glu
            100                 105                 110

His His Ser Gln Ala Leu Met Gly Ser Ser Arg Glu Thr Thr Ala Leu
        115                 120                 125

Ser Gln Thr Gln Leu Ala Ser Ser Asn Val Pro Ala Ala Gly Ile
    130                 135                 140

<210> SEQ ID NO 55
<211> LENGTH: 143
<212> TYPE: PRT
<213> ORGANISM: Artificial Sequence
<220> FEATURE:
<223> OTHER INFORMATION: KIR2DL5 endodomain

<400> SEQUENCE: 55

Thr Gly Ile Arg Arg His Leu His Ile Leu Ile Gly Thr Ser Val Ala
1               5                   10                  15

Ile Ile Leu Phe Ile Ile Leu Phe Phe Phe Leu Leu His Cys Cys Cys
            20                  25                  30

Ser Asn Lys Lys Asn Ala Ala Val Met Asp Gln Glu Pro Ala Gly Asp
        35                  40                  45

Arg Thr Val Asn Arg Glu Asp Ser Asp Gln Asp Pro Gln Glu Val
    50                  55                  60

Thr Tyr Ala Gln Leu Asp His Cys Val Phe Thr Gln Thr Lys Ile Thr
65                  70                  75                  80

Ser Pro Ser Gln Arg Pro Lys Thr Pro Pro Thr Asp Thr Thr Met Tyr
                85                  90                  95

Met Glu Leu Pro Asn Ala Lys Pro Arg Ser Leu Ser Pro Ala His Lys
            100                 105                 110

His His Ser Gln Ala Leu Arg Gly Ser Ser Arg Glu Thr Thr Ala Leu
        115                 120                 125

Ser Gln Asn Arg Val Ala Ser Ser His Val Pro Ala Ala Gly Ile
    130                 135                 140

<210> SEQ ID NO 56
<211> LENGTH: 111
<212> TYPE: PRT
<213> ORGANISM: Artificial Sequence
<220> FEATURE:
```

<223> OTHER INFORMATION: KIR3DL1 endodomain

<400> SEQUENCE: 56

Lys Asp Pro Arg His Leu His Ile Leu Ile Gly Thr Ser Val Val Ile
1               5                   10                  15

Ile Leu Phe Ile Leu Leu Leu Phe Phe Leu Leu His Leu Trp Cys Ser
            20                  25                  30

Asn Lys Lys Asn Ala Ala Val Met Asp Gln Glu Pro Ala Gly Asn Arg
        35                  40                  45

Thr Ala Asn Ser Glu Asp Ser Asp Glu Gln Asp Pro Glu Glu Val Thr
    50                  55                  60

Tyr Ala Gln Leu Asp His Cys Val Phe Thr Gln Arg Lys Ile Thr Arg
65                  70                  75                  80

Pro Ser Gln Arg Pro Lys Thr Pro Pro Thr Asp Thr Ile Leu Tyr Thr
                85                  90                  95

Glu Leu Pro Asn Ala Lys Pro Arg Ser Lys Val Val Ser Cys Pro
            100                 105                 110

<210> SEQ ID NO 57
<211> LENGTH: 97
<212> TYPE: PRT
<213> ORGANISM: Artificial Sequence
<220> FEATURE:
<223> OTHER INFORMATION: KIR3DL3 endodomain

<400> SEQUENCE: 57

Lys Asp Pro Gly Asn Ser Arg His Leu His Val Leu Ile Gly Thr Ser
1               5                   10                  15

Val Val Ile Ile Pro Phe Ala Ile Leu Leu Phe Phe Leu Leu His Arg
            20                  25                  30

Trp Cys Ala Asn Lys Lys Asn Ala Val Val Met Asp Gln Glu Pro Ala
        35                  40                  45

Gly Asn Arg Thr Val Asn Arg Glu Asp Ser Asp Glu Gln Asp Pro Gln
    50                  55                  60

Glu Val Thr Tyr Ala Gln Leu Asn His Cys Val Phe Thr Gln Arg Lys
65                  70                  75                  80

Ile Thr Arg Pro Ser Gln Arg Pro Lys Thr Pro Pro Thr Asp Thr Ser
                85                  90                  95

Val

<210> SEQ ID NO 58
<211> LENGTH: 807
<212> TYPE: PRT
<213> ORGANISM: Artificial Sequence
<220> FEATURE:
<223> OTHER INFORMATION: PTPN6-CD45 fusion protein

<400> SEQUENCE: 58

Trp Tyr His Gly His Met Ser Gly Gly Gln Ala Glu Thr Leu Leu Gln
1               5                   10                  15

Ala Lys Gly Glu Pro Trp Thr Phe Leu Val Arg Glu Ser Leu Ser Gln
            20                  25                  30

Pro Gly Asp Phe Val Leu Ser Val Leu Ser Asp Gln Pro Lys Ala Gly
        35                  40                  45

Pro Gly Ser Pro Leu Arg Val Thr His Ile Lys Val Met Cys Glu Gly
    50                  55                  60

Gly Arg Tyr Thr Val Gly Gly Leu Glu Thr Phe Asp Ser Leu Thr Asp
65                  70                  75                  80

-continued

```
Leu Val Glu His Phe Lys Lys Thr Gly Ile Glu Ala Ser Gly Ala
             85                  90                  95
Phe Val Tyr Leu Arg Gln Pro Tyr Lys Ile Tyr Asp Leu His Lys Lys
            100                 105                 110
Arg Ser Cys Asn Leu Asp Glu Gln Gln Glu Leu Val Glu Arg Asp Asp
        115                 120                 125
Glu Lys Gln Leu Met Asn Val Glu Pro Ile His Ala Asp Ile Leu Leu
    130                 135                 140
Glu Thr Tyr Lys Arg Lys Ile Ala Asp Glu Gly Arg Leu Phe Leu Ala
145                 150                 155                 160
Glu Phe Gln Ser Ile Pro Arg Val Phe Ser Lys Phe Pro Ile Lys Glu
                165                 170                 175
Ala Arg Lys Pro Phe Asn Gln Asn Lys Asn Arg Tyr Val Asp Ile Leu
            180                 185                 190
Pro Tyr Asp Tyr Asn Arg Val Glu Leu Ser Glu Ile Asn Gly Asp Ala
        195                 200                 205
Gly Ser Asn Tyr Ile Asn Ala Ser Tyr Ile Asp Gly Phe Lys Glu Pro
    210                 215                 220
Arg Lys Tyr Ile Ala Ala Gln Gly Pro Arg Asp Glu Thr Val Asp Asp
225                 230                 235                 240
Phe Trp Arg Met Ile Trp Glu Gln Lys Ala Thr Val Ile Val Met Val
                245                 250                 255
Thr Arg Cys Glu Glu Gly Asn Arg Asn Lys Cys Ala Glu Tyr Trp Pro
            260                 265                 270
Ser Met Glu Glu Gly Thr Arg Ala Phe Gly Asp Val Val Lys Ile
        275                 280                 285
Asn Gln His Lys Arg Cys Pro Asp Tyr Ile Ile Gln Lys Leu Asn Ile
    290                 295                 300
Val Asn Lys Lys Glu Lys Ala Thr Gly Arg Glu Val Thr His Ile Gln
305                 310                 315                 320
Phe Thr Ser Trp Pro Asp His Gly Val Pro Glu Asp Pro His Leu Leu
                325                 330                 335
Leu Lys Leu Arg Arg Arg Val Asn Ala Phe Ser Asn Phe Phe Ser Gly
            340                 345                 350
Pro Ile Val Val His Cys Ser Ala Gly Val Gly Arg Thr Gly Thr Tyr
        355                 360                 365
Ile Gly Ile Asp Ala Met Leu Glu Gly Leu Glu Ala Glu Asn Lys Val
    370                 375                 380
Asp Val Tyr Gly Tyr Val Val Lys Leu Arg Arg Gln Arg Cys Leu Met
385                 390                 395                 400
Val Gln Val Glu Ala Gln Tyr Ile Leu Ile His Gln Ala Leu Val Glu
                405                 410                 415
Tyr Asn Gln Phe Gly Glu Thr Glu Val Asn Leu Ser Glu Leu His Pro
            420                 425                 430
Tyr Leu His Asn Met Lys Lys Arg Asp Pro Pro Ser Glu Pro Ser Pro
        435                 440                 445
Leu Glu Ala Glu Phe Gln Arg Leu Pro Ser Tyr Arg Ser Trp Arg Thr
    450                 455                 460
Gln His Ile Gly Asn Gln Glu Glu Asn Lys Ser Lys Asn Arg Asn Ser
465                 470                 475                 480
Asn Val Ile Pro Tyr Asp Tyr Asn Arg Val Leu Lys His Glu Leu Glu
                485                 490                 495
```

```
Met Ser Lys Glu Ser Glu His Asp Ser Asp Glu Ser Asp Asp Asp
            500                 505                 510

Ser Asp Ser Glu Glu Pro Ser Lys Tyr Ile Asn Ala Ser Phe Ile Met
            515                 520                 525

Ser Tyr Trp Lys Pro Glu Val Met Ile Ala Ala Gln Gly Pro Leu Lys
        530                 535                 540

Glu Thr Ile Gly Asp Phe Met Ile Gln Arg Lys Val Lys Val Ile Val
545                 550                 555                 560

Met Leu Thr Glu Leu Lys His Gly Asp Gln Glu Ile Cys Ala Gln Tyr
                565                 570                 575

Trp Gly Glu Gly Lys Gln Thr Tyr Gly Asp Ile Glu Val Asp Leu Lys
            580                 585                 590

Asp Thr Asp Lys Ser Ser Thr Tyr Thr Leu Arg Val Phe Glu Leu Arg
            595                 600                 605

His Ser Lys Arg Lys Asp Ser Arg Thr Val Tyr Gln Tyr Gln Tyr Thr
            610                 615                 620

Asn Trp Ser Val Glu Gln Leu Pro Ala Glu Pro Lys Glu Leu Ile Ser
625                 630                 635                 640

Met Ile Gln Val Val Lys Gln Lys Leu Pro Gln Lys Asn Ser Ser Glu
                645                 650                 655

Gly Asn Lys His His Lys Ser Thr Pro Leu Leu Ile His Cys Arg Asp
                660                 665                 670

Gly Ser Gln Gln Thr Gly Ile Phe Cys Ala Leu Leu Asn Leu Leu Glu
            675                 680                 685

Ser Ala Glu Thr Glu Val Val Asp Ile Phe Gln Val Val Lys Ala
            690                 695                 700

Leu Arg Lys Ala Arg Pro Gly Met Val Ser Thr Phe Glu Gln Tyr Gln
705                 710                 715                 720

Phe Leu Tyr Asp Val Ile Ala Ser Thr Tyr Pro Ala Gln Asn Gly Gln
                725                 730                 735

Val Lys Lys Asn Asn His Gln Glu Asp Lys Ile Glu Phe Asp Asn Glu
            740                 745                 750

Val Asp Lys Val Lys Gln Asp Ala Asn Cys Val Asn Pro Leu Gly Ala
            755                 760                 765

Pro Glu Lys Leu Pro Glu Ala Lys Glu Gln Ala Glu Gly Ser Glu Pro
        770                 775                 780

Thr Ser Gly Thr Glu Gly Pro Glu His Ser Val Asn Gly Pro Ala Ser
785                 790                 795                 800

Pro Ala Leu Asn Gln Gly Ser
                805

<210> SEQ ID NO 59
<211> LENGTH: 434
<212> TYPE: PRT
<213> ORGANISM: Artificial Sequence
<220> FEATURE:
<223> OTHER INFORMATION: PTPN6-CD148 fusion

<400> SEQUENCE: 59

Glu Thr Leu Leu Gln Ala Lys Gly Glu Pro Trp Thr Phe Leu Val Arg
1               5                   10                  15

Glu Ser Leu Ser Gln Pro Gly Asp Phe Val Leu Ser Val Leu Ser Asp
            20                  25                  30

Gln Pro Lys Ala Gly Pro Gly Ser Pro Leu Arg Val Thr His Ile Lys
        35                  40                  45
```

```
Val Met Cys Glu Gly Gly Arg Tyr Thr Val Gly Gly Leu Glu Thr Phe
 50                  55                  60

Asp Ser Leu Thr Asp Leu Val Glu His Phe Lys Lys Thr Gly Ile Glu
 65                  70                  75                  80

Glu Ala Ser Gly Ala Phe Val Tyr Leu Arg Gln Pro Tyr Arg Lys Lys
                 85                  90                  95

Arg Lys Asp Ala Lys Asn Asn Glu Val Ser Phe Ser Gln Ile Lys Pro
                100                 105                 110

Lys Lys Ser Lys Leu Ile Arg Val Glu Asn Phe Glu Ala Tyr Phe Lys
            115                 120                 125

Lys Gln Gln Ala Asp Ser Asn Cys Gly Phe Ala Glu Glu Tyr Glu Asp
130                 135                 140

Leu Lys Leu Val Gly Ile Ser Gln Pro Lys Tyr Ala Ala Glu Leu Ala
145                 150                 155                 160

Glu Asn Arg Gly Lys Asn Arg Tyr Asn Asn Val Leu Pro Tyr Asp Ile
                165                 170                 175

Ser Arg Val Lys Leu Ser Val Gln Thr His Ser Thr Asp Asp Tyr Ile
            180                 185                 190

Asn Ala Asn Tyr Met Pro Gly Tyr His Ser Lys Lys Asp Phe Ile Ala
            195                 200                 205

Thr Gln Gly Pro Leu Pro Asn Thr Leu Lys Asp Phe Trp Arg Met Val
210                 215                 220

Trp Glu Lys Asn Val Tyr Ala Ile Ile Met Leu Thr Lys Cys Val Glu
225                 230                 235                 240

Gln Gly Arg Thr Lys Cys Glu Glu Tyr Trp Pro Ser Lys Gln Ala Gln
                245                 250                 255

Asp Tyr Gly Asp Ile Thr Val Ala Met Thr Ser Glu Ile Val Leu Pro
            260                 265                 270

Glu Trp Thr Ile Arg Asp Phe Thr Val Lys Asn Ile Gln Thr Ser Glu
            275                 280                 285

Ser His Pro Leu Arg Gln Phe His Phe Thr Ser Trp Pro Asp His Gly
290                 295                 300

Val Pro Asp Thr Thr Asp Leu Leu Ile Asn Phe Arg Tyr Leu Val Arg
305                 310                 315                 320

Asp Tyr Met Lys Gln Ser Pro Pro Glu Ser Pro Ile Leu Val His Cys
                325                 330                 335

Ser Ala Gly Val Gly Arg Thr Gly Thr Phe Ile Ala Ile Asp Arg Leu
            340                 345                 350

Ile Tyr Gln Ile Glu Asn Glu Asn Thr Val Asp Val Tyr Gly Ile Val
            355                 360                 365

Tyr Asp Leu Arg Met His Arg Pro Leu Met Val Gln Thr Glu Asp Gln
370                 375                 380

Tyr Val Phe Leu Asn Gln Cys Val Leu Asp Ile Val Arg Ser Gln Lys
385                 390                 395                 400

Asp Ser Lys Val Asp Leu Ile Tyr Gln Asn Thr Thr Ala Met Thr Ile
                405                 410                 415

Tyr Glu Asn Leu Ala Pro Val Thr Thr Phe Gly Lys Thr Asn Gly Tyr
            420                 425                 430

Ile Ala

<210> SEQ ID NO 60
<211> LENGTH: 5
<212> TYPE: PRT
<213> ORGANISM: Artificial Sequence
```

```
<220> FEATURE:
<223> OTHER INFORMATION: truncated COMP coiled-coil domain

<400> SEQUENCE: 60

Cys Asp Ala Cys Gly
1               5

<210> SEQ ID NO 61
<211> LENGTH: 20
<212> TYPE: PRT
<213> ORGANISM: Artificial Sequence
<220> FEATURE:
<223> OTHER INFORMATION: truncated COMP coiled-coil domain

<400> SEQUENCE: 61

Gln Gln Val Arg Glu Ile Thr Phe Leu Lys Asn Thr Val Met Glu Cys
1               5                   10                  15

Asp Ala Cys Gly
            20

<210> SEQ ID NO 62
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be Arg or Lys

<400> SEQUENCE: 62

Arg Xaa Xaa Arg
1

<210> SEQ ID NO 63
<211> LENGTH: 7
<212> TYPE: PRT
<213> ORGANISM: Artificial Sequence
<220> FEATURE:
<223> OTHER INFORMATION: consensus Tobacco Etch Virus (TEV) cleavage
      site

<400> SEQUENCE: 63

Glu Asn Leu Tyr Phe Gln Ser
1               5

<210> SEQ ID NO 64
<211> LENGTH: 6
<212> TYPE: PRT
<213> ORGANISM: Artificial Sequence
<220> FEATURE:
<223> OTHER INFORMATION: ITIM conserved sequence
<220> FEATURE:
<221> NAME/KEY: MISC_FEATURE
<222> LOCATION: (1)..(1)
<223> OTHER INFORMATION: Xaa may be Ser, Ile, Val or Leu
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
```

```
<221> NAME/KEY: MISC_FEATURE
<222> LOCATION: (6)..(6)
<223> OTHER INFORMATION: Xaa may be Ile, Val or Leu

<400> SEQUENCE: 64

Xaa Xaa Tyr Xaa Xaa Xaa
1               5
```